United States Patent
Schada Von Borzyskowski et al.

(10) Patent No.: US 12,378,570 B2
(45) Date of Patent: Aug. 5, 2025

(54) METHOD FOR THE PRODUCTION OF PLANTS WITH ALTERED PHOTORESPIRATION AND IMPROVED CO₂ FIXATION

(71) Applicants: Max-Planck-Gesellschaft zur Förderung der Wissenschaften e.V., Munich (DE); Heinrich-Heine-Universität Düsseldorf, Düsseldorf (DE)

(72) Inventors: Lennart Schada Von Borzyskowski, Marburg (DE); Tobias Jürgen Erb, Marburg (DE); Andreas Paul Michael Weber, Düsseldorf (DE); Marc-Sven Roll, Düsseldorf (DE)

(73) Assignees: Max-Planck-Gesellschaft zur Förderung der Wissenschaften e.V., Munich (DE); Heinrich-Heine-Universitat Dusseldorf, Dusseldorf (DE)

( * ) Notice: Subject to any disclaimer, the term of this patent is extended or adjusted under 35 U.S.C. 154(b) by 397 days.

(21) Appl. No.: 17/632,867

(22) PCT Filed: Aug. 5, 2020

(86) PCT No.: PCT/EP2020/072071
§ 371 (c)(1),
(2) Date: Feb. 4, 2022

(87) PCT Pub. No.: WO2021/023801
PCT Pub. Date: Feb. 11, 2021

(65) Prior Publication Data
US 2022/0315942 A1    Oct. 6, 2022

(30) Foreign Application Priority Data
Aug. 6, 2019   (EP) .................... 19190404

(51) Int. Cl.
*C12N 15/82* (2006.01)
*C12N 9/88* (2006.01)

(52) U.S. Cl.
CPC ........... *C12N 15/8269* (2013.01); *C12N 9/88* (2013.01); *C12N 15/8245* (2013.01)

(58) Field of Classification Search
None
See application file for complete search history.

(56) References Cited

U.S. PATENT DOCUMENTS

2006/0095981 A1   5/2006  Hain et al.
2012/0301947 A1   11/2012 Milo et al.

OTHER PUBLICATIONS

Nokhal and Schlegel. Int J Systematic Bacteriology.33(1): 26-37. (Year: 1983).*
Kornberg and Morris. "βHydroxyaspartate Pathway: A New Route for Biosyntheses from Glyoxylate," Nature. 197:456-457. (Year: 1963).*
Schwander. "The design and realization of synthetic pathways for the fixation of carbon dioxide in vitro." Dissertation. Philipps-Universität Marburg. (Year: 2017).*
Gibbs. "The enzymology of the B-hydroxyaspartate pathway". Dissertation. University of Leicester. (Year: 1966).*
GenBank Accession WP_011750151.1. (Year: 2018).*
Borzyskowski, et al. Nature. 575:500-504. (Year: 2019).*
International Search Report and Written Opinion for International Patent Application No. PCT/EP2020/072071 dated Sep. 22, 2020, 11 pages.
H. L Kornberg et al: "[beta]Hydroxyaspartate Pathway: A New Route for Biosyntheses from Glyoxylate", Nature, Feb. 2, 1963 (Feb. 2, 1963), pp. 456-457, XP055648258,EnglandDOI: 10.1038/197456a0Retrieved from the Internet:URL:https://www.nature.com/articles/197456 a0.pdfthe whole document.
Thomas Schwander: "The design and realization of synthetic pathways for the fixation of carbon dioxide in vitro", Jan. 1, 2018 (Jan. 1, 2018), XP055648354, Retrieved from the Internet: URL:http://archiv.ub.uni-marburg.de/diss/z2018/0066/pdf/dts.pdf p. 85, "6.1. Synthetic CO2 fixation cycles", especially last two sentences.
Bar-Even Arren et al: "Design and analysis of synthetic carbon fixation pathways", Proceedings of the National Academy of Sciences, National Academy of Sciences, vol. 107, No. 19, May 11, 2010 (May 11, 2010) , pp. 8889-8894, XP002638327, ISSN: 0027-8424, DOI: 10.1073/PNAS.0907176107 [retrieved on Apr. 21, 2010] abstract.

* cited by examiner

*Primary Examiner* — Mykola V. Kovalenko
*Assistant Examiner* — David R Byrnes
(74) *Attorney, Agent, or Firm* — Amin, Turocy & Watson, LLP

(57) ABSTRACT

The present invention relates to transgenic plants with altered photorespiration and improved CO₂ fixation as well as a method of producing said transgenic plants. Particularly, the transgenic plants show an improved growth rate, productivity and energy conversion efficiency. This method can be successfully applied to many agricultural crop plants with nutritional and medicinal uses.

11 Claims, 20 Drawing Sheets
Specification includes a Sequence Listing.

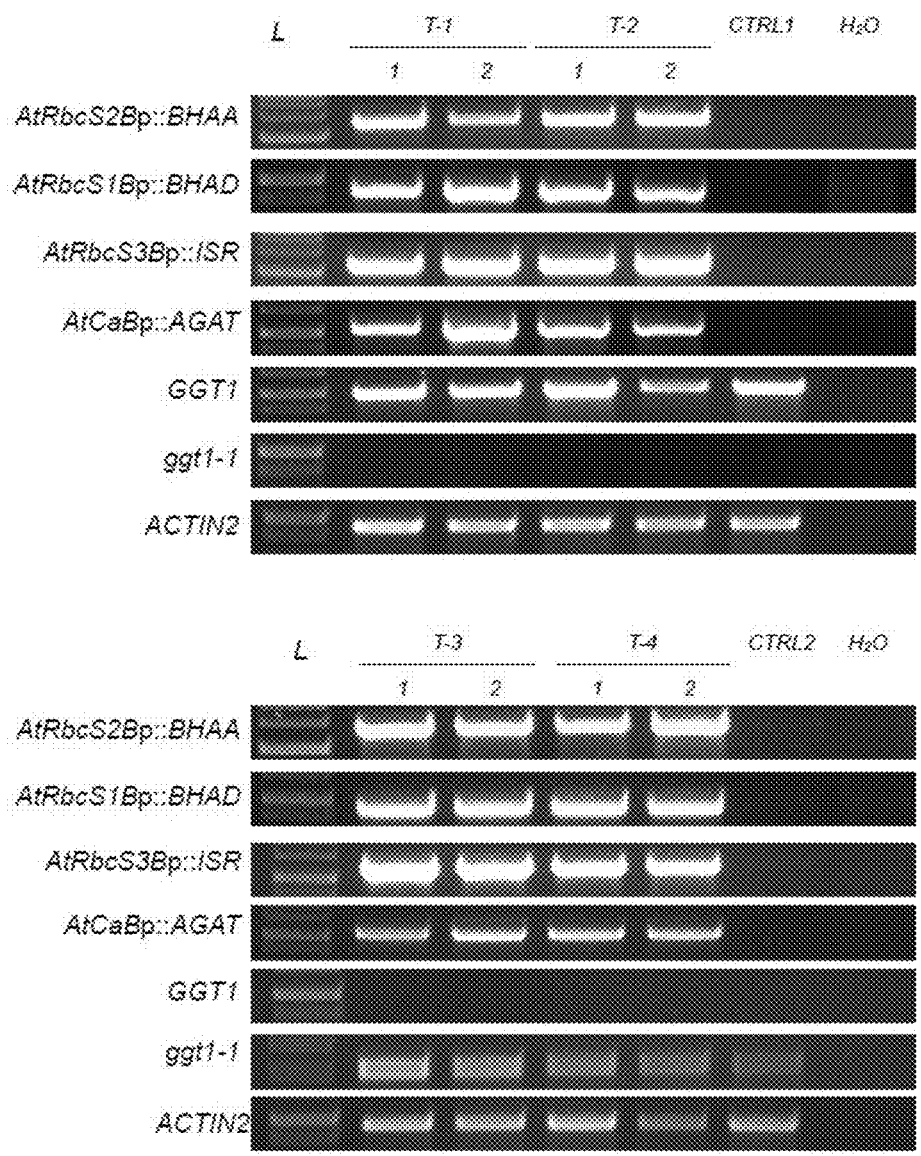
Figure 16 (*continue*)

Figure 17 (*continue*)
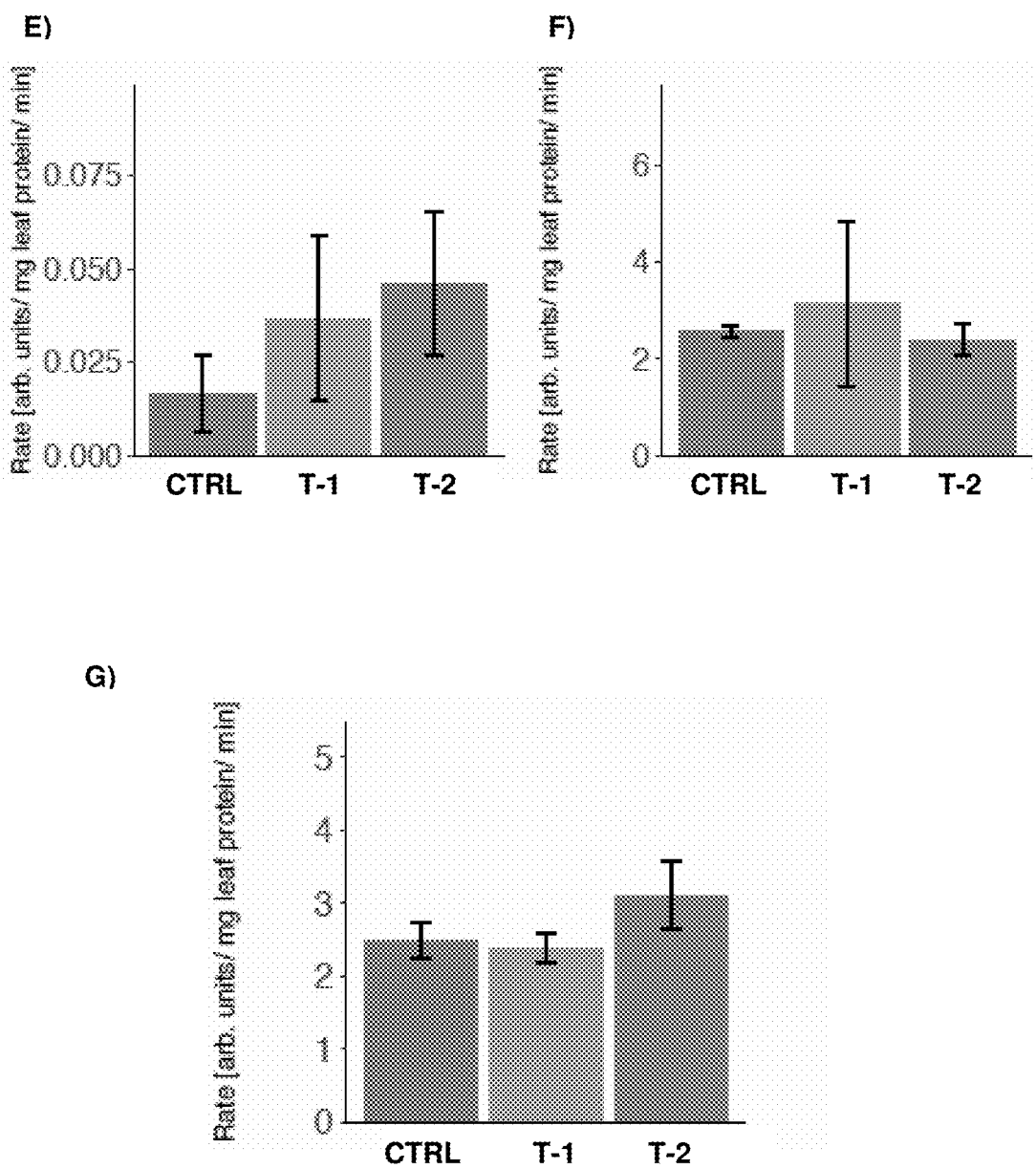

METHOD FOR THE PRODUCTION OF PLANTS WITH ALTERED PHOTORESPIRATION AND IMPROVED CO$_2$ FIXATION

FIELD OF THE INVENTION

The present invention relates to transgenic plants with altered photorespiration and improved CO$_2$ fixation as well as a method of producing said transgenic plants. Particularly, the transgenic plants show an improved growth rate, productivity and energy conversion efficiency.

BACKGROUND OF THE INVENTION

The invention relates to a method for the production of plants with altered photorespiration and improved CO$_2$ fixation. Indeed, biological fixation of CO$_2$ is an important process carried out by plants and a number of microorganisms, which can be harnessed to improve growth, productivity, and/or yield for agricultural crop plants. Many efforts have recently been made to improve growth and resistance of crop plants. Some of the most important crop plants, e.g. rice, wheat, barley, potato, belong to the so-called C3 plants. Only a few important crop plants, like corn and sugar cane, are C4 plants.

CO$_2$ fixation in C3 plants is primarily catalyzed by the enzyme ribulose-1,5-bisphosphate carboxylase (RUBISCO) which is located inside the chloroplasts. The enzyme RUBISCO catalyzes two reactions: carboxylation and oxygenation of ribulose-1,5-bisphosphate. The product of the first reaction are two molecules of 3-phosphoglycerate which enter the Calvin cycle to form starch and ribulose-1, 5-bisphosphate. The products of the oxygenase reaction are each one molecule of 3-phosphoglycerate and phosphoglycolate. The latter is converted to 3-phosphoglycerate in a biosynthetic pathway named photorespiration. In the course of this complex sequence of reactions one molecule of CO$_2$ is released and lost for the plant. This loss of CO$_2$ reduces the formation of sugars and polysaccharides in the plant and thus reduces their productivity. Furthermore, NH$_3$ is released which has to be refixed. High amounts of phosphoglycolate are produced that enter the photorespiratory cycle. It has been estimated that plants loose approximately 25% of the already fixed carbon due to photorespiration. However, this cycle is absolutely intrinsic to all C3 plants because of the oxygenase activity of RUBISCO.

The importance of the photorespiration for plant growth and yield has been shown by experiments where the enhanced CO$_2$ supply indicated that a suppression of photorespiration indeed resulted in higher growth and more yield (Peterhansel and Maurino, *Plant Physiology* 2011).

However, despite several attempts to improve CO$_2$ fixation and reduce photorespiration until now, no suitable method has been provided that leads to an improvement of growth, productivity, and/or yield for agricultural crop plants.

WO2003/100066A1 discloses the re-use of 2-phosphoglycolate produced in photorespiration in a pathway that converts 2-phosphoglycolate into 3-phosphoglycerate. Further, WO2009/103782A1 describes the conversion of glycolate into malate. However, similar to other alternative photorespiration routes, also the pathways disclosed in WO2003/100066A1 and WO2009/103782A1 result in the release of CO$_2$ and therefore do not remedy the major deficit of natural photorespiration. WO2016/207219A1 reports on the conversion of 2-phosphoglycolate into an intermediate compound of the Calvin-Benson-Bassham Cycle. WO 2015/120343 A2 discloses methods and compositions for introduction of a synthetic pathway based on the 3-hydroxypropionate (3OHP) bicycle into host organisms such as cyanobacteria, plants or algae. The heterologous expressed pathway acts as a photorespiratory bypass as well as an additional carbon fixation cycle orthogonal to the endogenous Calvin-Benson cycle (CBC).

The patent application WO 2011/099006 A2 discloses a system for carbon fixation with enzymes which catalyze reactions of a carbon fixation pathway, where at least one of the reactions of the carbon fixation pathway is a carboxylation reaction, where products of the reactions of the carbon fixation pathway comprise oxaloacetate and malonyl-CoA, where an enzyme which performs the carboxylation reaction is selected from the group consisting of phophoenolpyruvate (PEP) carboxylase, pyruvate carboxylase and acetyl-CoA carboxylase, and where an additional export product of the carbon fixation pathway is glyoxylate. In another embodiment, pyruvate is the export product. The system is expressed in bacteria cells, algae cells, and higher plant cells.

Kornberg and Morris (Nature, 1963, 197: 456-457) is a scientific publication disclosing a potential reaction route of *Micrococcus Denitrificans*, partially supported by experimental data, in which two molar units of glyoxylate are converted to one molar unit of oxaloacetic acid. In the reaction route, the authors suppose the transfer of an amino group from β-hydroxyaspartate to glyoxylic acid to yield glycine. To notice, Komber and Morris do not disclose the reactions between β-hydroxyaspartate and oxaloacetic acid. Moreover, Komber and Morris do not disclose which enzymes or genes are involved in the presented reaction route.

The doctoral thesis of T. Schwander "The design and realization of synthetic pathways for the fixation of carbon dioxide in vitro" (2018), discloses the design of synthetic CO$_2$ fixation pathways combining enzymes from different organisms.

Bar-Even et al. (Proceedings of the National Academy of Sciences, 2010, 107, 8889-8894) discloses novel synthetic cycles combining existing metabolic building blocks from various organisms.

EP 1 367 127 A1 is directed to a method for the production of plants with suppressed photorespiration and improved CO$_2$ fixation. In particular, the invention relates to a re-use of phosphoglycolate produced in photorespiration, by installing a glycolate oxidizing pathway inside the chloroplast. This is accomplished by introducing into the plant genome, one or more nucleic acids encoding enzymes of glycolate utilizing pathways, such as (i) glycolate oxidase or glycolate dehydrogenase, (ii) glyoxylate carboligase, and (iii) tatronic semialdehyde reductase. However, data about the transformation efficiency in target plants and the phenotype of transformed plants are not disclosed.

Therefore, it is the objective of the present invention to provide transgenic plants with altered photorespiration and improved CO$_2$ fixation as well as a method of producing said transgenic plants, thereby increasing the growth rate, productivity and energy conversion efficiency of plants.

The objective of the present invention is solved by the teaching of the independent claims. Further advantageous features, aspects and details of the invention are evident from the dependent claims, the description, the figures, and the examples of the present application.

BRIEF DESCRIPTION OF THE INVENTION

The present invention is directed to a method for the production of a transgenic plant with altered photorespiration and improved CO₂ fixation, comprising introducing into a cell or tissue of said plant one or more nucleic acids encoding at least four polypeptides having the enzymatic activities of
(a) erythro-β-hydroxyaspartate aldolase belonging to the EC class 4.1.3.14,
(b) erythro-β-hydroxyaspartate dehydratase belonging to the EC class 4.3.1.20,
(c) iminosuccinate reductase and
(d) aspartate-glyoxylate transaminase,
wherein the introduction of said nucleic acid(s) results in a de novo expression of the at least four polypeptides having the enzymatic activities of
(a) erythro-β-hydroxyaspartate aldolase belonging to the EC class 4.1.3.14,
(b) erythro-β-hydroxyaspartate dehydratase belonging to the EC class 4.3.1.20,
(c) iminosuccinate reductase and
(d) aspartate-glyoxylate transaminase.

The method of the present invention relates to the bypass of the naturally-occurring photorespiration pathways in plants with the β-hydroxyaspartate pathway (BHAP), which was elucidated by the inventors in proteobacteria, such as in *Paracoccus denitrificans*.

Based on the sequence of a putative β-hydroxyaspartate aldolase gene (dhaa; GenBank Accession No. AB075600) from *Paracoccus denitrificans* IFO 1330123, the inventors have identified a homolog in the genome of *P. denitrificans* DSM413 (BLT64_RS06500), which is part of a gene cluster, consisting of four structural genes and a putative transcriptional regulator. Besides the BHA aldolase (Pden_3919; annotated as alanine racemase), the operon comprises ORFs annotated as coding for serine-glyoxylate aminotransferase (Pden_3921), serine/threonine dehydratase (Pden_3920) and ornithine cyclodeaminase (Pden_3918). The putative transcriptional regulator (Pden_3922; annotated as IclR-family regulator) is in opposite orientation to the four structural genes of the presumed BHAP operon. To verify that these genes indeed encode for the enzymes of the BHAP, the ORFs were cloned and separately overexpressed in *Escherichia coli* BL21. The purified enzymes were tested in spectrophotometric assays to elucidate their function and confirm their role in the BHAP. The inventors could confirm that Pden_3919 encodes for the key enzyme of the BHAP, BHA aldolase, which catalyzes the condensation of glyoxylate and glycine into β-hydroxyaspartate. Furthermore, while Pden_3921 is correctly annotated as a PLP-dependent aminotransferase, the inventors could show that its preferred substrates are aspartate and glyoxylate, which are converted into oxaloacetate and glycine, therefore this enzyme has been here named as aspartate-glyoxylate aminotransferase. The function of Pden_3920 as BHA dehydratase, which had previously been purified from cell-free extracts of *P. denitrificans* (Gibbs and Morris 1965), could be confirmed. Moreover the inventors could show that Pden_3918 encodes for a polypeptide having enzymatic activity of iminosuccinate reductase (and not ornithine cyclodeaminase), which reduces iminosuccinate to L-aspartate, thereby regenerating the amino group donor in the first step of the BHAP. The inventors could further show by phylogenetic analysis that the BHAP is widespread in α- and γ-proteobacteria, in terrestrial as well as marine habitats. There is no prior art document disclosing or suggesting the complete BHAP pathway comprising the enzymes β-hydroxyaspartate aldolase (BHAA), β-hydroxyaspartate dehydratase (BHAD), iminosuccinate reductase (ISRed), and aspartate-glyoxylate transaminase (ASGAT), or disclosing genes coding for any of the BHAP pathway enzymes.

The kinetic parameters of all enzymes of the BHAP are reported in Table 6. The complete reaction sequence of the pathway is shown in FIG. 1. Overall, the β-hydroxyaspartate pathway comprises the conversion of two units of glyoxylate (C2) to one unit oxaloacetate (C4), which can be further metabolized in the tricarboxylic acid (TCA) cycle, under consumption of one unit of the cofactor NADH. In contrast to the natural photorespiration pathways as listed in Table 1 below, no CO₂ is released, no ATP and only 1 equivalent of NADH is required. The BHAP represents a CO₂ neutral photorespiration bypass pathway with the least amount of required reducing equivalents and the regeneration of the catalytic amino donor, which makes it the most efficient glyoxylate assimilation pathway described to date. Thus, the BHAP may lead to an increased growth rate, productivity and energy conversion efficiency of the transgenic plants.

TABLE 1

Comparison of previously published natural photorespiration pathways with the BHAP regarding their substrates, products, and energy requirements. Note that the BHAP compares favorably to all other pathways both in carbon balance and in required energy input.

| Pathway | Substrate(s) | Product(s) | Required ATP | Required reducing equivalents |
|---|---|---|---|---|
| Glycerate pathway | 2 glyoxylate | phosphoglycerate + CO₂ | 1 | 1 |
| Glycine cleavage pathway | 2 glyoxylate + glutamate | phosphoglycerate + CO₂ + 2-oxoglutarate + NH₃ | 1 | 1 |
| Glyoxylate oxidation | 2 glyoxylate | 4 CO₂ | — | 2 |
| BHAP | 2 glyoxylate | oxaloacetate | — | 1 |

In the BHAP (FIG. 1), the enzyme (a) β-hydroxyaspartate aldolase (BHAA) catalyzes the condensation of glycine and glyoxylate to (2R,3S)-β-hydroxyaspartate and the enzyme (b) β-hydroxyaspartate dehydratase (BHAD) catalyzes the subsequent dehydration to iminosuccinate. The iminosuccinate is reduced to aspartate by the (c) iminosuccinate reductase (ISRed) in the presence of the cofactor NADH and the formed aspartate is finally converted with glyoxylate to oxaloacetate and glycine in the presence of the enzyme (d) aspartate-glyoxylate transaminase (AsGAT). Oxaloacetate formed in the BHAP can directly enter the tricarboxylic acid cycle or the gluconeogenesis in the cytosol.

The inventors have successfully integrated the four genes of the BHAP from *Paracoccus denitrificans* DSM413 and from other microorganisms in plant peroxisomes, where a high concentration of photorespiration-derived glyoxylate is expected. To this aim, the four required genes of the BHAP were codon-optimized for expression in *Arabidopsis thaliana* by gene synthesis; moreover four enzymes were targeted to plant peroxisomes by synthetic fusion with peroxisomal targeting sequences. The inventors were able to demonstrate the correct localization of BHAP enzymes in plant peroxisomes (FIG. 3), by means of co-localization studies with peroxisomal organellar markers.

Moreover, the inventors were able to demonstrate activity of each of the BHAP enzymes in *N. benthamiana* leaf extracts (FIGS. 4-7). In order to differentiate the activity of IsRed from malate dehydrogenase activity, the formation of aspartate (via IsRed) and malate (via malate dehydrogenase) was quantified via LC-MS. As shown, both aspartate and malate were formed in the respective enzyme assay (FIG. 8), with the ratio of malate:aspartate being approximately 100 towards the end of the assay (FIG. 9).

Finally, the inventors constructed a multigene T-DNA nucleic acid construct for implementation of the BHAP in plants (FIG. 10). Functionality of this nucleic acid construct, regarding expression of all four enzymes was verified by transient expression in *N. benthamiana* followed by immunoblot analysis (FIG. 11-12). Although constitutive expression of multiple transgenes is a predominant approach in plants and might be of interest for future studies, the inventors use a fine-tuned approach of BHAP expression in plants. Within the multigene nucleic acid construct each BHAP enzyme is expressed under its own photosynthetically regulated promoter, restricting BHAP expression to photosynthetic tissue and coupling BHAP expression to light and high photorespiratory metabolic flux.

The inventors have successfully integrated the four genes of the BHAP at two different neutral sites of the chromosome of *S. elongatus* PCC7942 (see Example 11). This was done both in the wild type strain and in a deletion strain that lacks the genes necessary for the formation of carboxysomes (ccmK-O), and therefore requires elevated atmospheric $CO_2$ concentrations for growth (this strain is henceforth referred to as ΔK-O). As shown in FIG. 13, the activity of each single enzyme in the ΔK-O strain was at least 300 mU/mg, while the reaction sequence from glycine and glyoxylate to aspartate (via BHA aldolase, BHA dehydratase and iminosuccinate reductase) was measured at an activity of ~100 mU/mg, notably without any additional coupling enzymes, thereby verifying the successful expression of the pathway enzymes as well as the maintenance of the enzyme activity. The expression level of the BHAP enzymes is high enough to sustain photorespiratory flux in *S. elongatus* PCC7942 ΔK-O. In addition, the inventors could show in growth experiments that the implantation of the BHAP in microorganisms permits a more than 20% faster growth of the microorganism at 30° C. and 37° C. (see Table 9 and FIGS. 14 and 15) compared to the ΔK-O control strain. Therefore, it was successfully demonstrated that the bypass of the naturally-occurring photorespiration pathways in autotrophic microorganisms with the β-hydroxyaspartate pathway (BHAP) by the inventive method results in a faster growth of the autotrophic microorganisms.

Of relevance, the inventor successfully stably integrated the BHAP synthetic pathway in *Arabidopsis thaliana* wild-type plants (Col-0) and in ggt-1 mutant (FIG. 16). The established transgenic lines with the BHAP in WT and ggt1 mutant background were analyzed for phenotype (Example 8), enzymatic activity of all four BHAP enzymes (Example 7), and metabolomic profile (Example 9). Results showed that the transgenic plants engineered with the BHAP performed markedly better than the ggt1 mutant background (FIGS. 18-20), and expressed the functional enzymes in active form of the BHAP (FIGS. 17 and 23).

Therefore, it can be concluded that implementation of the β-hydroxyaspartate pathway (BHAP) in plants results in an increased growth, productivity, and/or yield for agricultural crop plants.

DESCRIPTION OF THE INVENTION

Definitions

Throughout this specification amino acid residues will be denoted by the three-letter abbreviation or single-letter code as follows:

| Amino Acid | Three-letter abbreviation | One-letter Symbol |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The term "plants" as used herein includes, unless indicated otherwise, plant bodies, plant organs, plant tissues, plant cells, and seeds. An example of a plant cell includes callus. An example of a plant organ includes a root, a leaf, a flower and the like, In contrast, microscopic organism, i.e. microorganisms, which may exist in its single-celled form or in a colony of cells and which is not visible to the naked eye as individual, are not considered as plants herein.

The term "C3 plants" refers to plants which fix $CO_2$ in a C3 pathway of photosynthesis, including monocotyledonous plants such as rice, wheat, and barley, as well as dicotyledonous plants such as soybeans, potatoes, and sweet potatoes.

The term "C4 plants" refers to plants which fix $CO_2$ in the C4 pathway of photosynthesis, including monocotyledonous plants such as maize, sugarcane, and sorghum, as well as dicotyledonous plants such as *Flaveria*, and *Amaranthus*.

"Iminosuccinate reductase" as used herein refers to a polypeptide having an iminosuccinate reductase activity, i.e. an iminosuccinate reductase catalyzes the reaction of iminosuccinate (or iminoaspartate) to aspartate in the presence of a cofactor such as NADH. It is to be understood that iminosuccinate reductases are not limited to polypeptide variants derived from the naturally occurring iminosuccinate reductases from various bacteria, such as *Paracoccus denitrificans*, but may include other enzymes having iminosuccinate reductase activity, or recombinant variants of the naturally occurring iminosuccinate reductases, including but not limiting enzymes comprising an amino acid sequence selected from proteobacteria SEQ ID NO: 1-299, such as *Paracoccus denitrificans* (SEQ ID NO: 135).

As used herein, "erythro-β-hydroxyaspartate aldolase" (or synonymously L-erythro-3-hydroxyaspartate aldolase) refers to a polypeptide having a β-hydroxyaspartate aldolase activity, i.e. a polypeptide that catalyzes the reaction of glyoxylate and glycine to erythro-β-hydroxyaspartate. The β-hydroxyaspartate aldolase belongs to the EC class 4.1.3.14. This enzyme is closely related to D-threonine aldolases and differs in the active site by three amino acids A160, A195 and S313, which may provide a signature sequence for this enzyme family (data not shown).

As used herein, "erythro-β-hydroxyaspartate dehydratase" (or synonymously erythro-3-hydroxy-L-aspartate ammonia-lyase) refers to a polypeptide having a β-hydroxyaspartate dehydratase activity, i.e. a polypeptide that catalyzes the reaction of erythro-β-hydroxyaspartate to iminosuccinate. The β-hydroxyaspartate dehydratase belongs to the EC class 4.3.1.20 or former EC class 4.2.1.38.

"aspartate-glyoxylate transaminase" as used herein refers to a polypeptide having an aspartate-glyoxylate transaminase activity, i.e. an aspartate-glyoxylate transaminase catalyzes the reaction of aspartate and glyoxylate to oxaloacetate and glycine. It is to be understood that aspartate-glyoxylate transaminases are not limited to polypeptide variants derived from the naturally occurring aspartate-glyoxylate transaminases from various bacteria, such as *Paracoccus denitrificans*, but may include other enzymes having aspartate-glyoxylate transaminase activity, or recombinant variants of the naturally occurring aspartate-glyoxylate transaminases, including but not limiting enzymes comprising an amino acid sequence selected from proteobacteria SEQ ID NO: 300-599, such as *Paracoccus denitrificans* (SEQ ID NO: 433).

"Percentage of sequence identity" and "percentage homology" are used interchangeably herein to refer to comparisons among nucleic acids and polypeptides, and are determined by comparing two optimally aligned sequences over a comparison window, wherein the portion of the nucleic acids or polypeptide sequence in the comparison window may comprise additions or deletions (i.e. gaps) as compared to the reference sequence for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences.

"Reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two nucleic acids or polypeptides may each (1) comprise a sequence (i.e., a portion of the complete sequence) that is similar between the two sequences, and (2) may further comprise a sequence that is divergent between the two sequences, sequence comparisons between two (or more) nucleic acids or polypeptide are typically performed by comparing sequences of the two nucleic acids or polypeptides over a "comparison window" to identify and compare local regions of sequence similarity. In some embodiments, a "reference sequence" can be based on a primary amino acid sequence, where the reference sequence is a sequence that can have one or more changes in the primary sequence.

"Substantial identity" refers to a nucleic acid or polypeptide sequence that has at least 80 percent sequence identity, at least 85 percent identity and 89 to 95 percent sequence identity, more usually at least 99 percent sequence identity as compared to a reference sequence over a comparison window of at least 20 residue positions, frequently over a window of at least 30-50 residues, wherein the percentage of sequence identity is calculated by comparing the reference sequence to a sequence that includes deletions or additions which total 20 percent or less of the reference sequence over the window of comparison. In specific embodiments applied to polypeptides, the term "substantial identity" means that two polypeptide sequences, when optimally aligned, share at least 80 percent sequence identity, preferably at least 89 percent sequence identity, at least 95 percent sequence identity or more (e.g., 99 percent sequence identity). Preferably, residue positions which are not identical differ by conservative amino acid substitutions.

"Deletion" refers to modification to the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the reference enzyme while retaining enzymatic activity and/or retaining the improved properties of an engineered imine reductase enzyme. Deletions can be directed to the internal portions and/or terminal portions of the polypeptide. In various embodiments, the deletion can comprise a continuous segment or can be discontinuous.

"Insertion" refers to modification to the polypeptide by addition of one or more amino acids from the reference polypeptide. In some embodiments, the improved engineered imine reductase enzymes comprise insertions of one or more amino acids to the naturally occurring polypeptide having imine reductase activity as well as insertions of one or more amino acids to other improved imine reductase polypeptides. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

"Synthetic nucleotide sequence" as used herein means a nucleotide sequence comprising structural characters that are not present in the natural sequence. For example, an artificial sequence that resembles more closely the G+C content and the normal codon distribution of dicot and/or monocot genes is said to be synthetic. A regulatory DNA sequence is said to be "operably linked to" or "associated with" a DNA sequence that codes for an RNA or a protein if the two sequences are situated such that the regulatory DNA sequence affects expression of the coding DNA sequence.

The term "promoter" or "promoter region" refers to a nucleic acid sequence, usually found upstream (5') to a coding sequence that controls expression of the coding sequence by controlling production of messenger RNA (mRNA) by providing the recognition site for RNA polymerase and/or other factors necessary for start of transcription at the correct site. As contemplated herein, a promoter or promoter region includes variations of promoters derived by means of ligation to various regulatory sequences, random or controlled mutagenesis, and addition or duplication of enhancer sequences. The promoter region disclosed herein, and biologically functional equivalents thereof, are responsible for driving the transcription of coding sequences under their control when introduced into a host as part of a suitable recombinant vector, as demonstrated by its ability to produce mRNA. The promoter region may also include elements that act as regulators of gene expression such as activators, enhancers, and/or repressors.

The term "terminator" region refers to a sequence of DNA that causes RNA polymerase to terminate transcription. Suitable terminator sequences contemplated herein are: *Agrobacterium tumefaciens* octopine synthase terminator (AtuOCSt), *Agrobacterium tumefaciens* nopaline synthase terminator (AtuNOSt), 35S terminator derived from the Cauliflower Mosaic Virus (35St), *Solanum lycopersicum* RubisCO small subunit 3C terminator (SIRbcS3Ct).

As used herein, the term "selection marker" gene or nucleic acid includes any gene which confers a phenotype on a cell in which it is expressed to facilitate the identification and/or selection of cells which are transfected or transformed with a genetic construct of the invention or a derivative thereof.

Suitable "selection marker" genes or nucleic acids contemplated herein include the ampicillin-resistance, tetracycline-resistance gene, kanamycin-resistance gene (KanR), zeocin resistance gene, the AURI-C gene conferring resistance to the antibiotic aureobasidin A, phosphinothricin-resistance gene, neomycin phosphotransferase gene (nptII), hygromycin-resistance gene, glucuronidase gene, chloramphenicol acetyltransferase (CAT) gene, green fluorescent protein (GFP) encoding gene or the luciferase encoding gene, amongst others.

Preferably, the selectable marker gene is the kanamycin resistance (KanR) encoding gene.

"Heterologous" as used herein means "of different natural or of synthetic origin" or represent a nonnatural state. For example, if a host cell or microorganism is transformed with a nucleic sequence derived from another organism, particularly from another microorganism, that gene is heterologous with respect to that host cell or microorganism and also with respect to descendants of the host cell which carry that gene. The transforming nucleic acid may comprise a heterologous promoter, heterologous coding sequence, or heterologous termination sequence. Alternatively, the transforming nucleic acid may be completely heterologous or may comprise any possible combination of heterologous and endogenous nucleic acid sequences.

"Transformation" refers to a process of introducing an exogenous nucleic acid sequence (e.g., a vector, recombinant nucleic acid molecule) into a cell or protoplast in which that exogenous nucleic acid is incorporated into a chromosome or is capable of autonomous replication.

A "transformed cell" is a cell whose nucleic acid has been altered by the introduction of an exogenous nucleic acid molecule into that cell.

A "transformed plant" or "transgenic plant" is a plant whose nucleic acid has been altered by the introduction of an exogenous nucleic acid molecule into that plant, or by the introduction of an exogenous nucleic acid molecule into a plant cell from which the plant was regenerated or derived. As disclosed herein, a transgenic plant comprises one or more nucleic acids encoding four polypeptides having the enzymatic activities of a) erythro-β-hydroxyaspartate aldolase, (b) erythro-β-hydroxyaspartate dehydratase, (c) iminosuccinate reductase, and (d) aspartate-glyoxylate transaminase, and wherein BHAP can be implemented in cytosol or peroxisomes. If the BHAP is implemented in the mitochondria, the transgenic plant according to the present invention comprises one or more nucleic acids encoding five polypeptides having the enzymatic activities of a) erythro-β-hydroxyaspartate aldolase, (b) erythro-β-hydroxyaspartate dehydratase, (c) iminosuccinate reductase, (d) aspartate-glyoxylate transaminase, and (e) glycolate dehydrogenase. If the BHAP is implemented in the chloroplasts, the transgenic plant according to the present invention comprises one or more nucleic acids encoding six polypeptides having the enzymatic activities of a) erythro-β-hydroxyaspartate aldolase, (b) erythro-β-hydroxyaspartate dehydratase, (c) iminosuccinate reductase, (d) aspartate-glyoxylate transaminase, (e) glycolate dehydrogenase, and (f) phosphoenolpyruvate carboxykinase.

The nucleic acid constructs as described herein includes at least one promoter, the coding regions of multiple genes encoding one or more proteins, selection marker genes, and sequences transcription termination. The constructs may also include sequences encoding targeting sequences, such as sequences encoding plastid targeting sequences, or tissue specific sequences, such as peptides specific targeting seed. These constructs are made using the MoClo kit. The transfer DNA (abbreviated T-DNA) is the transferred DNA of the tumor-inducing (Ti) plasmid of some species of bacteria such as *Agrobacterium tumefaciens*. The T-DNA is transferred from bacterium into the host plant's nuclear DNA genome. The capability of this specialized tumor-inducing (Ti) plasmid is attributed to two essential regions required for DNA transfer to the host cell. *Agrobacterium*-mediated T-DNA transfer is widely used as a tool in biotechnology for introducing genes into plants for basic research as well as for commercial production of transgenic crops. In genetic engineering, the tumor-promoting and opine-synthesis genes are removed from the T-DNA and replaced with a gene of interest and/or a selection marker, which is required to establish which plants have been successfully transformed. Examples of selection markers include kanamycin, neomycin phosphotransferase, hygromycin B phosphotransferase, and phosphinothricin acetyltransferase. *Agrobacterium* is then used as a vector to transfer the engineered T-DNA into the plant cells where it integrates into the plant genome. This method can be used to generate transgenic plants carrying a foreign gene. *Agrobacterium tumefaciens* is capable of transferring foreign DNA to both monocotyledons and dicotyledonous plants efficiently while taking care of critically important factors like the genotype of plants, types and ages of tissues inoculated, kind of vectors, strains of *Agrobacterium*, selection marker genes and selective agents, and various tissue culture conditions.

The present invention is directed to a method for the production of a transgenic plant with altered photorespiration and improved $CO_2$ fixation, comprising introducing into a cell or tissue of said plant one or more nucleic acids encoding at least four polypeptides having the enzymatic activities of
- (a) erythro-β-hydroxyaspartate aldolase belonging to the EC class 4.1.3.14,
- (b) erythro-β-hydroxyaspartate dehydratase belonging to the EC class 4.3.1.20,
- (c) iminosuccinate reductase and
- (d) aspartate-glyoxylate transaminase, wherein the introduction of said nucleic acid(s) results in a de novo expression of the at least four polypeptides having the enzymatic activities of
- (a) erythro-β-hydroxyaspartate aldolase belonging to the EC class 4.1.3.14,
- (b) erythro-β-hydroxyaspartate dehydratase belonging to the EC class 4.3.1.20,
- (c) iminosuccinate reductase and
- (d) aspartate-glyoxylate transaminase.

It is to be understood that all four enzymes of the BHAP must be expressed in the transgenic plant in order to alter the photorespiration and to improve the $CO_2$ fixation in said plants. Therefore, the step introducing into a cell or tissue of said plant one or more nucleic acids encoding polypeptides having the enzymatic activities (a)-(d) refers to (i) a single nucleotide encoding all four polypeptides having the enzymatic activities (a)-(d), or (ii) the implementation of multiple nucleic acids which encode together the polypeptides having the enzymatic activities (a)-(d). For example, the BHAP may be implemented in a transgenic plant according to the present invention by using 4 nucleic acids, each encoding a different polypeptide having the enzymatic activities (a)-(d).

In other words, the present invention is directed to a method for the production of a transgenic plant with altered photorespiration and improved $CO_2$ fixation, comprising introducing into a cell or tissue of said plant one or more nucleic acids encoding at least four polypeptides having the enzymatic activities of
- (a) erythro-β-hydroxyaspartate aldolase belonging to the EC class 4.1.3.14,
- (b) erythro-β-hydroxyaspartate dehydratase belonging to the EC class 4.3.1.20,
- (c) iminosuccinate reductase and
- (d) aspartate-glyoxylate transaminase, wherein the introduction of all said nucleic acid(s) results in a de novo expression of the at least four polypeptides having the enzymatic activities of
- (a) erythro-β-hydroxyaspartate aldolase belonging to the EC class 4.1.3.14,
- (b) erythro-β-hydroxyaspartate dehydratase belonging to the EC class 4.3.1.20,
- (c) iminosuccinate reductase and
- (d) aspartate-glyoxylate transaminase.

Reworded, the present invention is directed to a method for the production of a transgenic plant with altered photorespiration and improved $CO_2$ fixation, comprising introducing into a cell or tissue of said plant one or more nucleic acids encoding polypeptides comprising Pden 3919 (GenBank: ABL71985), Pden 3920 (GenBank: ABL71986), Pden 3918 (GenBank: ABL71984) and Pden_3921 (GenBank: ABL71987) or homologs or variants thereof, wherein the introduction of said nucleic acid(s) results in a de novo expression of the polypeptides Pden_3919, Pden_3920, Pden_3918 and Pden_392, wherein Pden_3919 has the enzymatic activity of an (a) erythro-β-hydroxyaspartate Pden_3920 has the enzymatic activity of an (b) erythro-β-hydroxyaspartate dehydratase, Pden_3918 has the enzymatic activity of an (c) iminosuccinate reductase, and Pden_3921 has the enzymatic activity of an (d) aspartate-glyoxylate transaminase.

Thus, in one embodiment the method for the production of a transgenic plant with altered photorespiration and improved $CO_2$ fixation, comprises introducing into a cell or tissue of said plant one nucleic acid encoding at least four polypeptides having the enzymatic activities of
- (a) erythro-β-hydroxyaspartate aldolase belonging to the EC class 4.1.3.14,
- (b) erythro-β-hydroxyaspartate dehydratase belonging to the EC class 4.3.1.20,
- (c) iminosuccinate reductase and
- (d) aspartate-glyoxylate transaminase, wherein the introduction of said nucleic acid results in a de novo expression of the at least four polypeptides having the enzymatic activities of
- (a) erythro-β-hydroxyaspartate aldolase belonging to the EC class 4.1.3.14,
- (b) erythro-β-hydroxyaspartate dehydratase belonging to the EC class 4.3.1.20,
- (c) iminosuccinate reductase and
- (d) aspartate-glyoxylate transaminase.

By phylogenetic analysis the inventors have revealed that the BHAP is widely distributed among proteobacteria, particularly alpha- and gamma-proteobacteria, such as *Aestuariivita boseongensis, Agrobacterium* sp., *Ahrensia* sp., *Aminobacter aminovorans, Amphritea atlantica, Antarctobacter heliothermus, Aquisalimonas asiatica, Aurantimonas altamirensis, Aureimonas altamirensis, Brevirhabdus pacifica, Citreicella marina, Citreicella* sp., *Citreicella thiooxidans, Citreimonas salinaria, Colwellia piezophila, Colwellia psychrerythraea, Colwellia* sp, *Cribrihabitans marinus, Defluviimonas indica, Defluviimonas* sp., *Dinoroseobacter shibae, Ensifer fredii, Ensifer meliloti, Ensifer* sp., *Glaciecola* sp., *Granulosicoccus antarcticus, Halocynthiibacter* sp., *Hasllibacter halocynthiae, Hyphomicrobium sulfonivorans, Jannaschia pohangensis, Jannaschia rubra, Jannaschia* sp., *Labrenzia aggregata, Labrenzia alba, Labrenzia alexandrii, Labrenzia* sp., *Leisingera aquaemixtae, Leisingera nanhaiensis, Leisingera* sp., *Litoreibacter ascidiaceicola, Litoreibacter halocynthiae, Litoreibacter janthinus, Litoreibacter meonggei, Litoreibacter ponti, Loktanella koreensis, Loktanella litorea, Loktanella maricola, Loktanella rosea, Loktanella sediminilitoris, Loktanella sediminum, Loktanella* sp., *Loktanella vestfoldensis, Mameliella alba, Maribius* sp., *Marinobacter psychrophilus, Marinobacter* sp., *Marinobacterium lutimaris, Marinobacterium mangrovicola, Marinobacterium* sp., *Marinomonas* sp., *Marinovum algicola, Maritimibacter* sp., *Marivita geojedonensis, Marivita hallyeonensis, Mesorhizobium* sp., *Mesorhizobium* sp., *Methylobacterium komagatae, Methylobacterium mesophilicum, Methylobacterium radiotolerans, Methylobacterium* sp., *Methylobacterium* sp., *Methylopila* sp., *Neptunomonas antarctica, Nitratireductor* sp., *Oceanicola flagellatus, Oceanicola nitratireducens, Oceanicola* sp., *Oceaniovalibus guishaninsula, Octadecabacter antarcticus, Octadecabacter arcticus, Octadecabacter temperatus, Palleronia marisminoris, Leisingera aquimarina, Paracoccus alcaliphilus, Paracoccus alkenifer, Paracoccus aminophilus, Paracoccus aminovorans, Paracoccus denitrificans, Paracoccus halophilus, Paracoccus homiensis, Paracoccus isoporae, Paracoccus pantotrophus, Paracoccus saliphilus, Paracoccus sediminis, Paracoccus* sp., *Paracoccus thiocyanatus, Paracoccus versutus, Paracoccus yeei, Pararhodobacter aggregans, Phaeobacter caeruleus, Phaeobacter daeponensis, Pelagibaca bermudensis, Pelagicola*

*litoralis, Pelagimonas varians, Phaeobacter gallaeciensis, Phaeobacter inhibens, Planktotalea frisia, L. methylohalidivorans, Ponticoccus litoralis, Ponticoccus* sp., *Poseidonocella pacifica, Pseudomonas stutzeri, Pseudopelagicola gijangensis, Pseudorhodobacter antarcticus, Pseudoruegeria haliotis, Pseudoruegeria marinistellae, Psychrobacter arcticus, Psychrobacter cryohalolentis, Psychrobacter* sp., *Psychrobacter urativorans, Puniceibacterium sediminis, Rhizobium etli, Rhizobium etli, Rhizobium etli, Rhizobium leguminosarum, Rhizobium lusitanum, Rhizobium rhizogenes, Rhizobium* sp., *Rhizobium taibaishanense, Rhizobium tropici, Rhizobium yanglingense, Rhodobaca barguzinensis, Rhodobacteraceae bacterium, Rhodobacteraceae* sp., *Rhodobacterales bacterium, Rhodovibrio salinarum, Rhodovulum kholense, Rhodovulum* sp., *Rhodovulum sulfidophilum, Roseinatronobacter thiooxidans, Roseivivax halodurans, Roseivivax isoporae, Roseivivax lentus, Roseivivax sediminis, Roseobacter denitrificans, Roseobacter litoralis, Roseobacter* sp., *Roseovarius azorensis, Roseovarius indicus, Roseovarius litoreus, Roseovarius lutimaris, Roseovarius marisflavi, Roseovarius mucosus, Roseovarius nubinhibens, Roseovarius sediminilitoris, Roseovarius* sp., *Roseovarius tolerans, Rubellimicrobium mesophilum, Rubrimonas cliftonensis, Ruegeria atlantica, Ruegeria conchae, Ruegeria faecimaris, Ruegeria halocynthiae, Ruegeria marina, Ruegeria mobilis, Ruegeria scottomollicae, Ruegeria* sp., *Sagittula stellata, Salinihabitans flavidus, Shimia haliotis, Shimia sagamensis, Silicibacter* sp., *Sinorhizobium americanum, Sinorhizobium fredii, Sinorhizobium terangae, Solemya velum, Sphingomonas* sp., *Stappia aggregata, Starkeya novella, Sulfitobacter pseudonitzschiae, Sulfitobacter* sp., *Tateyamaria omphalii, Tateyamaria* sp., *Thalassobacter* sp., *Thalassobacter stenotrophicus, Thalassobius abyssi, Thalassobius aestuarii, Thalassobius mediterraneus, Thalassotalea* sp., *uncultured Rhodobacteriaceae, Yangia pacifica, Yangia pacifica, Yangia* sp., *Paracoccus sulfuroxidans, AP Rhodobacteraceae bacterium* and *Silicibacter pomeroyi*.

Therefore, the inventive method is not restricted to the BHAP enzymes of *P. denitrificans* DSM413, and BHAP enzymes with same activity of other origin, particularly proteobacteria, can be used as well. Thus, the method for the production of a transgenic plant with altered photorespiration and improved $CO_2$ fixation, comprises introducing into a cell or tissue of said plant one or more nucleic acids encoding at least four polypeptides having the enzymatic activities of
(a) erythro-β-hydroxyaspartate aldolase belonging to the EC class 4.1.3.14,
(b) erythro-β-hydroxyaspartate dehydratase belonging to the EC class 4.3.1.20,
(c) iminosuccinate reductase and
(d) aspartate-glyoxylate transaminase,
wherein the introduction of said nucleic acid(s) results in a de novo expression of the at least four polypeptides having the enzymatic activities of
(a) erythro-β-hydroxyaspartate aldolase belonging to the EC class 4.1.3.14,
(b) erythro-β-hydroxyaspartate dehydratase belonging to the EC class 4.3.1.20,
(c) iminosuccinate reductase and
(d) aspartate-glyoxylate transaminase,
wherein the de novo expressed polypeptides having the enzymatic activities (a) erythro-β-hydroxyaspartate aldolase, (b) erythro-β-hydroxyaspartate dehydratase, (c) iminosuccinate reductase and (d) aspartate-glyoxylate transaminase are preferably derived from proteobacteria.

Moreover, in the inventive methods described herein, the de novo expressed polypeptides having the enzymatic activities (a) erythro-β-hydroxyaspartate aldolase, (b) erythro-β-hydroxyaspartate dehydratase, (c) iminosuccinate reductase and (d) aspartate-glyoxylate transaminase are preferably derived from alpha- or gamma-proteobacteria. Also, in the inventive methods described herein, the de novo expressed polypeptides having the enzymatic activities (a) erythro-β-hydroxyaspartate aldolase, (b) erythro-β-hydroxyaspartate dehydratase, (c) iminosuccinate reductase and (d) aspartate-glyoxylate transaminase are preferably derived from proteobacteria which belong to the genus selected from *Aquisalimonas, Poseidonocella, Marinobacter, Litoreibacter, Thalassobacter, Ruegeria, Paracoccus, Roseobacter, Leisingera, Loktanella, Methylobacterium, Sinorhizobium, Rhizobium, Agrobacter, Cribrihabitans, Dinoroseobacter, Octadecabacter, Planktotalea, Psychrobacter, Yangia, Pseudorhodobacter* or *Neptunomonas*. In one embodiment of the inventive method, the de novo expressed polypeptides having the enzymatic activities (a) erythro-β-hydroxyaspartate aldolase, (b) erythro-β-hydroxyaspartate dehydratase, (c) iminosuccinate reductase and (d) aspartate-glyoxylate transaminase are preferably derived from *Paracoccus denitrificans*.

Thus, the method for the production of a transgenic plant with altered photorespiration and improved $CO_2$ fixation, comprises introducing into a cell or tissue of said plant one or more nucleic acids encoding at least four polypeptides having the enzymatic activities of
(a) erythro-β-hydroxyaspartate aldolase belonging to the EC class 4.1.3.14,
(b) erythro-β-hydroxyaspartate dehydratase belonging to the EC class 4.3.1.20,
(c) iminosuccinate reductase and
(d) aspartate-glyoxylate transaminase,
wherein the introduction of said nucleic acid(s) results in a de novo expression of the at least four polypeptides having the enzymatic activities of
(a) erythro-β-hydroxyaspartate aldolase belonging to the EC class 4.1.3.14,
(b) erythro-β-hydroxyaspartate dehydratase belonging to the EC class 4.3.1.20,
(c) iminosuccinate reductase and
(d) aspartate-glyoxylate transaminase,
wherein the polypeptide having the enzymatic activity of (c) iminosuccinate reductase comprises an amino acid sequence selected from SEQ ID NOs: 1-299, or an amino acid sequence having at least 80% sequence identity to a sequence selected from SEQ ID NO: 1-299;
and the polypeptide having the enzymatic activity of (d) aspartate-glyoxylate transaminase comprises an amino acid sequence selected from SEQ ID NOs: 300-599, or an amino acid sequence having at least 80% sequence identity to a sequence selected from SEQ ID NO: 300-599.

The iminosuccinate reductase enzymes of SEQ ID NOs: 1-299 comprise the conserved amino acid sequence of $GX_aKX_aG(X_a)_4(X_c)_2(X_a)_2GX_aKX_aGG(X_a)_2PX_aN(X_a)_3X_c(X_a)_3NHQS(X_a)_3LF(X_a)_4G(X_a)_8N$ $(X_a)_2TAX_aRTAA(X_a)_4S(X_a)_3L(X_a)_8G(X_a)_2GAGX_aQ(X_a)_3Q(X_a)_{15}WN(X_a)_{28}(X_c)_2(X_a)_9S(X_a)_1$ $_5H(X_a)_3MGTDT(X_a)_2KX_aE(X_a)_{13}D(X_a)_3Q(X_a)_4GEX_aQ(X_a)_{16}G(X_a)_9R(X_a)_2X_c(X_a)_3T(X_a)_2D$ $GX_aG(X_a)_3QDX_aA$ (SEQ ID NO: 967), wherein $X_a$ represents independently for each occurrence an amino acid, and wherein $X_c$ represents independently for each occurrence an amino acid or a gap.

The aspartate-glyoxylate transaminase enzymes of SEQ ID NOs: 300-599 comprise the conserved amino acid sequence of $W(X_b)_{12}L(X_b)_2D(X_b)_1(X_c)_2$ $(X_b)_9NETX_bTGVX_bS(X_b)_{20}DX_bVSS(X_b)_5F(X_b)_4W(X_b)_2D$ $(X_b)_4G$ $SQKGX_bM(X_b)_3G(X_b)_{31}(X_c)_4(X_b)_3PX_bTP(X_b)_6G$ $(X_b)_9X_cX_bE(X_b)_7RH(X_b)_3A(X_b)_3R(X_b)_5W$ $(X_b)_5A(X_b)_6S$ $(X_b)_8P(X_b)_{20}GX_bG(X_b)_8FRX_bGHX_bG(X_b)_{14}E(X_b)_{12}GX_bG$ $(X_b)_2AA$ (SEQ ID NO: 968), wherein $X_b$ represents independently for each occurrence an amino acid or a gap, and wherein $X_c$ represents independently for each occurrence an amino acid or a gap.

The conserved amino acid sequences SEQ ID NO 967 of the iminosuccinate reductase enzymes SEQ ID NO 1-299, and SEQ ID NO 968 of the aspartate-glyoxylate transaminase enzymes SEQ ID NOs: 300-599, have been designed with the help of Clustal Omega, which is a multiple sequence alignment program found at www.ebi.ac.uk/Tools/msa/clustalo/, using the "default parameters". The optimal multiple alignment between the input sequences in the comparison window is achieved by inserting deletions or gaps in the aligned sequences by the Clustal omega software. The maximal number of gaps inserted in one sequence to this aim was 4 for the alignment of the SEQ ID NOs 1-299, and 5 for the alignment of the sequences SEQ ID NOs 300-599. The conserved amino acid sequence SEQ ID NO 967 represents the 100% consensus sequence obtained by the multiple alignment of SEQ ID NOs 1-299. The conserved amino acid sequence SEQ ID NO 968 represents the 100% consensus sequence obtained by the multiple alignment of SEQ ID NOs 300-599.

Thus, in one embodiment, the method for the production of a transgenic plant with altered photorespiration and improved $CO_2$ fixation, comprises introducing into a cell or tissue of said plant one or more nucleic acids encoding at least four polypeptides having the enzymatic activities of
  (a) erythro-β-hydroxyaspartate aldolase belonging to the EC class 4.1.3.14,
  (b) erythro-β-hydroxyaspartate dehydratase belonging to the EC class 4.3.1.20,
  (c) iminosuccinate reductase and
  (d) aspartate-glyoxylate transaminase,
wherein the introduction of said nucleic acid(s) results in a de novo expression of the at least four polypeptides having the enzymatic activities of
  (a) erythro-β-hydroxyaspartate aldolase belonging to the EC class 4.1.3.14,
  (b) erythro-β-hydroxyaspartate dehydratase belonging to the EC class 4.3.1.20,
  (c) iminosuccinate reductase and
  (d) aspartate-glyoxylate transaminase,
wherein the polypeptide having the enzymatic activity of (c) iminosuccinate reductase comprises the conserved amino acid sequence of $GX_aKX_aG(X_a)_4(X_c)_2(X_a)_2GX_aKX_aGG$ $(X_a)_2PX_aN(X_a)_3X_c(X_a)_3NHQS(X_a)_3LF(X_a)_4G(X_a)_8N$ $(X_a)_2TAX_aRTAA(X_a)_4S(X_a)_3L(X_a)_8G(X_a)_2GAGX_a$ $Q(X_a)_3Q(X_a)_{15}WN(X_a)_{28}(X_c)_2(X_a)_8S(X_a)_{15}H(X_a)_3$ $MGTDT(X_a)_2KX_aE(X_a)_{13}D(X_a)_3Q(X_a)_4GEX_aQ(X_a)_{16}G$ $(X_a)R(X_a)_2X_c(X_a)_3T(X_a)_2D$ $GX_aG(X_a)_3QDX_aA$ (SEQ ID NO: 967), wherein $X_a$ represents independently for each occurrence an amino acid, wherein $X_c$ represents independently for each occurrence an amino acid or a gap, and wherein said polypeptide having the enzymatic activity of (c) iminosuccinate reductase comprises an amino acid sequence selected from SEQ ID NO: 1-299, or an amino acid sequence having at least 80% sequence identity to a sequence selected from SEQ ID NO: 1-299;
and the polypeptide having the enzymatic activity of (d) aspartate-glyoxylate transaminase comprises the conserved amino acid sequence of $W(X_b)_{12}L(X_b)_2D(X_b)_1(X_c)_2$ $(X_b)_9NETX_bTGVX_bS(X_b)_{20}DX_bVSS(X_b)_5F(X_b)_4W(X_b)_2D$ $(X_b)_4G$ $SQKGX_bM(X_b)_3G(X_b)_{31}(X_c)_4(X_b)_3PX_bTP(X_b)_6G$ $(X_b)_9X_cX_bE(X_b)_7RH(X_b)_3A(X_b)_3R(X_b)_5W$ $(X_b)_5A(X_b)_6S$ $(X_b)_8P(X_b)_{20}GX_bG(X_b)_8FRX_bGHX_bG(X_b)_{14}E(X_b)_{12}GX_bG$ $(X_b)_2AA$ (SEQ ID NO: 968), wherein $X_b$ represents independently for each occurrence an amino acid, wherein $X_c$ represents independently for each occurrence an amino acid or a gap, and said polypeptide having the enzymatic activity of (d) aspartate-glyoxylate transaminase comprises an amino acid sequence selected from SEQ ID NO: 300-599, or an amino acid sequence having at least 80% sequence identity to a sequence selected from SEQ ID NO: 300-599.

In one embodiment, the method for the production of a transgenic plant with altered photorespiration and improved $CO_2$ fixation, comprises introducing into a cell or tissue of said plant one or more nucleic acids encoding at least four polypeptides having the enzymatic activities of
  (a) erythro-β-hydroxyaspartate aldolase belonging to the EC class 4.1.3.14,
  (b) erythro-β-hydroxyaspartate dehydratase belonging to the EC class 4.3.1.20,
  (c) iminosuccinate reductase and
  (d) aspartate-glyoxylate transaminase,
wherein the introduction of said nucleic acid(s) results in a de novo expression of the at least four polypeptides having the enzymatic activities of
  (a) erythro-β-hydroxyaspartate aldolase belonging to the EC class 4.1.3.14,
  (b) erythro-β-hydroxyaspartate dehydratase belonging to the EC class 4.3.1.20,
  (c) iminosuccinate reductase and
  (d) aspartate-glyoxylate transaminase,
wherein the polypeptide having the enzymatic activity of (c) iminosuccinate reductase comprises the conserved amino acid sequence of $GX_aKX_aG(X_a)_4(X_c)_2(X_a)_2GX_aKX_aGG$ $(X_a)_2PX_aN(X_a)_3X_c(X_a)_3NHQS(X_a)_3LF(X_a)_4G(X_a)_8N$ $(X_a)_2TAX_aRTAA(X_a)_4S(X_a)_3L(X_a)_8G(X_a)_2GAGX_a$ $Q(X_a)_3Q(X_a)_{15}WN(X_a)_{28}(X_c)_2(X_a)_9S(X_a)_{15}H(X_a)_3$ $MGTDT(X_a)_2KX_aE(X_a)_{13}D(X_a)_3Q(X_a)_4GEX_aQ(X_a)_{16}G$ $(X_a)_9R(X_a)_2X_c(X_a)_3T(X_a)_2D$ $GX_aG(X_a)_3QDX_aA$ (SEQ ID NO: 967), wherein $X_a$ represents independently for each occurrence an amino acid, wherein $X_c$ represents independently for each occurrence an amino acid or a gap, and wherein said polypeptide having the enzymatic activity of (c) iminosuccinate reductase comprises an amino acid sequence having at least 80% sequence identity to a sequence selected from SEQ ID NO: 1-299;
and the polypeptide having the enzymatic activity of (d) aspartate-glyoxylate transaminase comprises the conserved amino acid sequence of $W(X_b)_{12}L(X_b)_2D(X_b)_1(X_c)_2$ $(X_b)_9NETX_bTGVX_bS(X_b)_{20}DX_bVSS(X_b)_5F(X_b)_4W(X_b)_2D$ $(X_b)_4G$ $SQKGX_bM(X_b)_3G(X_b)_{31}(X_c)_4(X_b)_3PX_bTP(X_b)_6G$ $(X_b)_9X_cX_bE(X_b)_7RH(X_b)_3A(X_b)_3R(X_b)_5W$ $(X_b)_5A(X_b)_6S$ $(X_b)_8P(X_b)_{20}GX_bG(X_b)_8FRX_bGHX_bG(X_b)_{14}E(X_b)_{12}GX_bG$ $(X_b)_2AA$ (SEQ ID NO: 968), wherein $X_b$ represents independently for each occurrence an amino acid, wherein $X_c$ represents independently for each occurrence an amino acid or a gap, and said polypeptide having the enzymatic activity of (d) aspartate-glyoxylate transaminase comprises an amino acid sequence having at least 80% sequence identity to a sequence selected from SEQ ID NO: 300-599.

In one embodiment, the method for the production of a transgenic plant with altered photorespiration and improved $CO_2$ fixation, comprises introducing into a cell or tissue of said plant one or more nucleic acids encoding at least four polypeptides having the enzymatic activities of (a) erythro-β-hydroxyaspartate aldolase belonging to the EC class 4.1.3.14,
(b) erythro-β-hydroxyaspartate dehydratase belonging to the EC class 4.3.1.20,
(c) iminosuccinate reductase and
(d) aspartate-glyoxylate transaminase, wherein the introduction of said nucleic acid(s) results in a de novo expression of the at least four polypeptides having the enzymatic activities of
(a) erythro-β-hydroxyaspartate aldolase belonging to the EC class 4.1.3.14,
(b) erythro-β-hydroxyaspartate dehydratase belonging to the EC class 4.3.1.20,
(c) iminosuccinate reductase and
(d) aspartate-glyoxylate transaminase, wherein the polypeptide having the enzymatic activity of (c) iminosuccinate reductase comprises an amino acid sequence selected from SEQ ID NO: 1-299;

and the polypeptide having the enzymatic activity of (d) aspartate-glyoxylate transaminase comprises an amino acid sequence selected from SEQ ID NO: 300-599.

In one embodiment, the method for the production of a transgenic plant with altered photorespiration and improved $CO_2$ fixation, comprises introducing into a cell or tissue of said plant one or more nucleic acids encoding at least four polypeptides having the enzymatic activities of
(a) erythro-β-hydroxyaspartate aldolase belonging to the EC class 4.1.3.14,
(b) erythro-β-hydroxyaspartate dehydratase belonging to the EC class 4.3.1.20,
(c) iminosuccinate reductase and
(d) aspartate-glyoxylate transaminase, wherein the introduction of said nucleic acid(s) results in a de novo expression of the at least four polypeptides having the enzymatic activities of
(a) erythro-β-hydroxyaspartate aldolase belonging to the EC class 4.1.3.14,
(b) erythro-β-hydroxyaspartate dehydratase belonging to the EC class 4.3.1.20,
(c) iminosuccinate reductase and
(d) aspartate-glyoxylate transaminase, wherein the polypeptide having the enzymatic activity of (c) iminosuccinate reductase comprises an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to a sequence selected from SEQ ID NO: 1-299;

and the polypeptide having the enzymatic activity of (d) aspartate-glyoxylate transaminase comprises an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to a sequence selected from SEQ ID NO: 300-599.

More in particular, the present invention is directed to a method for the production of a transgenic plant with altered photorespiration and improved $CO_2$ fixation, comprising introducing into a cell of said plant one or more nucleic acids encoding at least four polypeptides having the enzymatic activities of
(a) erythro-β-hydroxyaspartate aldolase belonging to the EC class 4.1.3.14,
(b) erythro-β-hydroxyaspartate dehydratase belonging to the EC class 4.3.1.20,
(c) iminosuccinate reductase and
(d) aspartate-glyoxylate transaminase, wherein the introduction of said nucleic acid(s) results in a de novo expression of the at least four polypeptides having the enzymatic activities of
(a) erythro-β-hydroxyaspartate aldolase belonging to the EC class 4.1.3.14,
(b) erythro-β-hydroxyaspartate dehydratase belonging to the EC class 4.3.1.20,
(c) iminosuccinate reductase and
(d) aspartate-glyoxylate transaminase, wherein the polypeptide having the enzymatic activity of (c) iminosuccinate reductase comprises an amino acid sequence selected from SEQ ID NO: 1-299, or an amino acid sequence having at least 80% sequence identity to a sequence selected from SEQ ID NO: 1-299;

and the polypeptide having the enzymatic activity of (d) aspartate-glyoxylate transaminase comprises an amino acid sequence selected from SEQ ID NO: 300-599, or an amino acid sequence having at least 80% sequence identity to a sequence selected from SEQ ID NO: 300-599.

In alternative, the present invention is directed to a method for the production of a transgenic plant with altered photorespiration and improved $CO_2$ fixation, comprising introducing into a tissue of said plant one or more nucleic acids encoding four polypeptides having the enzymatic activities of
(a) erythro-β-hydroxyaspartate aldolase belonging to the EC class 4.1.3.14,
(b) erythro-β-hydroxyaspartate dehydratase belonging to the EC class 4.3.1.20,
(c) iminosuccinate reductase and
(d) aspartate-glyoxylate transaminase, wherein the introduction of said nucleic acid(s) results in a de novo expression of the four polypeptides having the enzymatic activities of
(a) erythro-β-hydroxyaspartate aldolase belonging to the EC class 4.1.3.14,
(b) erythro-β-hydroxyaspartate dehydratase belonging to the EC class 4.3.1.20,
(c) iminosuccinate reductase and
(d) aspartate-glyoxylate transaminase, wherein the polypeptide having the enzymatic activity of (c) iminosuccinate reductase comprises an amino acid sequence selected from SEQ ID NO: 1-299, or an amino acid sequence having at least 80% sequence identity to a sequence selected from SEQ ID NO: 1-299;

and the polypeptide having the enzymatic activity of (d) aspartate-glyoxylate transaminase comprises an amino acid sequence selected from SEQ ID NO: 300-599, or an amino acid sequence having at least 80% sequence identity to a sequence selected from SEQ ID NO: 300-599.

In other words, the present invention is directed to a method for the production of a transgenic plant with altered photorespiration and improved $CO_2$ fixation, comprising introducing into a cell or tissue of said plant:
a nucleic acid sequence encoding a polypeptide having the enzymatic activity of a (a) erythro-β-hydroxyaspartate aldolase belonging to the EC class 4.1.3.14;
a nucleic acid sequence encoding a polypeptide having the enzymatic activity of a (b) erythro-β-hydroxyaspartate dehydratase belonging to the EC class 4.3.1.20;

a nucleic acid sequence encoding a polypeptide having the enzymatic activity of a (c) iminosuccinate reductase; and a nucleic acid sequence encoding a polypeptide having the enzymatic activity of a (d) aspartate-glyoxylate transaminase;

wherein the introduction of said nucleic acids results in a de novo expression of at least four polypeptides having the enzymatic activities of
- (a) erythro-β-hydroxyaspartate aldolase belonging to the EC class 4.1.3.14,
- (b) erythro-β-hydroxyaspartate dehydratase belonging to the EC class 4.3.1.20,
- (c) iminosuccinate reductase and
- (d) aspartate-glyoxylate transaminase, wherein the polypeptide having the enzymatic activity of (c) iminosuccinate reductase comprises an amino acid sequence selected from SEQ ID NO: 1-299, or an amino acid sequence having at least 80% sequence identity to a sequence selected from SEQ ID NO: 1-299;

and the polypeptide having the enzymatic activity of (d) aspartate-glyoxylate transaminase comprises an amino acid sequence selected from SEQ ID NO: 300-599, or an amino acid sequence having at least 80% sequence identity to a sequence selected from SEQ ID NO: 300-599.

In one embodiment, the method for the production of a transgenic plant with altered photorespiration and improved $CO_2$ fixation, comprises introducing into a cell or tissue of said plant one or more nucleic acids encoding at least four polypeptides having the enzymatic activities of
- (a) erythro-β-hydroxyaspartate aldolase belonging to the EC class 4.1.3.14,
- (b) erythro-β-hydroxyaspartate dehydratase belonging to the EC class 4.3.1.20,
- (c) iminosuccinate reductase and
- (d) aspartate-glyoxylate transaminase, wherein the introduction of said nucleic acid(s) results in a de novo expression of the at least four polypeptides having the enzymatic activities of
- (a) erythro-β-hydroxyaspartate aldolase belonging to the EC class 4.1.3.14,
- (b) erythro-β-hydroxyaspartate dehydratase belonging to the EC class 4.3.1.20,
- (c) iminosuccinate reductase and
- (d) aspartate-glyoxylate transaminase, wherein the polypeptide having the enzymatic activity of (c) iminosuccinate reductase comprises an amino acid sequence selected from SEQ ID NO: 1, 7, 22, 25, 26, 39, 47, 58, 75, 123, 135, and 160, or an amino acid sequence having at least 80% sequence identity to a sequence selected from SEQ ID NO: 1, 7, 22, 25, 26, 39, 47, 58, 75, 123, 135, and 160;

and the polypeptide having the enzymatic activity of (d) aspartate-glyoxylate transaminase comprises an amino acid sequence selected from SEQ ID NO: 300-599.

In one embodiment, the method for the production of a transgenic plant with altered photorespiration and improved $CO_2$ fixation, comprises introducing into a cell or tissue of said plant one or more nucleic acids encoding at least four polypeptides having the enzymatic activities of
- (a) erythro-β-hydroxyaspartate aldolase belonging to the EC class 4.1.3.14,
- (b) erythro-β-hydroxyaspartate dehydratase belonging to the EC class 4.3.1.20,
- (c) iminosuccinate reductase and
- (d) aspartate-glyoxylate transaminase, wherein the introduction of said nucleic acid(s) results in a de novo expression of the at least four polypeptides having the enzymatic activities of
- (a) erythro-β-hydroxyaspartate aldolase belonging to the EC class 4.1.3.14,
- (b) erythro-β-hydroxyaspartate dehydratase belonging to the EC class 4.3.1.20,
- (c) iminosuccinate reductase and
- (d) aspartate-glyoxylate transaminase, wherein the polypeptide having the enzymatic activity of (c) iminosuccinate reductase comprises an amino acid sequence selected from SEQ ID NO: 1, 7, 22, 25, 26, 39, 47, 58, 75, 123, 135, and 160, or an amino acid sequence having at least 80% sequence identity to a sequence selected from SEQ ID NO: 1, 7, 22, 25, 26, 39, 47, 58, 75, 123, 135, and 160;

and the polypeptide having the enzymatic activity of (d) aspartate-glyoxylate transaminase comprises an amino acid sequence selected from SEQ ID NO: 300-599.

In one embodiment, the method for the production of a transgenic plant with altered photorespiration and improved $CO_2$ fixation, comprises introducing into a cell or tissue of said plant one or more nucleic acids encoding at least four polypeptides having the enzymatic activities of
- (a) erythro-β-hydroxyaspartate aldolase belonging to the EC class 4.1.3.14,
- (b) erythro-β-hydroxyaspartate dehydratase belonging to the EC class 4.3.1.20,
- (c) iminosuccinate reductase and
- (d) aspartate-glyoxylate transaminase, wherein the introduction of said nucleic acid(s) results in a de novo expression of the at least four polypeptides having the enzymatic activities of
- (a) erythro-β-hydroxyaspartate aldolase belonging to the EC class 4.1.3.14,
- (b) erythro-β-hydroxyaspartate dehydratase belonging to the EC class 4.3.1.20,
- (c) iminosuccinate reductase and
- (d) aspartate-glyoxylate transaminase, wherein the polypeptide having the enzymatic activity of (c) iminosuccinate reductase comprises an amino acid sequence as set forth in SEQ ID NO: 135, or an amino acid sequence having at least 80% sequence identity to said sequence; and the polypeptide having the enzymatic activity of (d) aspartate-glyoxylate transaminase comprises an amino acid sequence as set forth in SEQ ID NO: 433, or an amino acid sequence having at least 80% sequence identity to said sequence.

In one embodiment, the method for the production of a transgenic plant with altered photorespiration and improved $CO_2$ fixation, comprises introducing into a cell or tissue of said plant one or more nucleic acids encoding at least four polypeptides having the enzymatic activities of
- (a) erythro-β-hydroxyaspartate aldolase belonging to the EC class 4.1.3.14,
- (b) erythro-β-hydroxyaspartate dehydratase belonging to the EC class 4.3.1.20,
- (c) iminosuccinate reductase and
- (d) aspartate-glyoxylate transaminase, wherein the introduction of said nucleic acid(s) results in a de novo expression of the at least four polypeptides having the enzymatic activities of
- (a) erythro-β-hydroxyaspartate aldolase belonging to the EC class 4.1.3.14,
- (b) erythro-β-hydroxyaspartate dehydratase belonging to the EC class 4.3.1.20,
- (c) iminosuccinate reductase and
- (d) aspartate-glyoxylate transaminase, wherein the polypeptide having the enzymatic activity of (c) iminosuccinate reductase comprises an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to a sequence as set forth in SEQ ID NO: 135;

and the polypeptide having the enzymatic activity of (d) aspartate-glyoxylate transaminase comprises an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to a sequence as set forth in SEQ ID NO: 433.

Preferably, in the inventive methods described herein, the de novo expressed polypeptide having the enzymatic activity of (a) erythro-β-hydroxyaspartate aldolase comprises an amino acid sequence having at least 80% sequence identity to SEQ ID NO: 953, the de novo expressed polypeptide having the enzymatic activity of (b) erythro-β-hydroxyaspartate dehydratase comprises an amino acid sequence having at least 80% sequence identity to SEQ ID NO: 954, the de novo expressed polypeptide having the enzymatic activity of (c) iminosuccinate reductase comprises an amino acid sequence having at least 80% sequence identity to a sequence selected from SEQ ID NO: 1-299, and the de novo expressed polypeptide having the enzymatic activity of (d) aspartate-glyoxylate transaminase comprises an amino acid sequence having at least 80% sequence identity to a sequence selected from SEQ ID NO: 300-599.

More preferably, in the inventive methods described herein, the de novo expressed polypeptide having the enzymatic activity of (a) erythro-β-hydroxyaspartate aldolase comprises an amino acid sequence having at least 90% sequence identity to SEQ ID NO: 953, the de novo expressed polypeptide having the enzymatic activity of (b) erythro-β-hydroxyaspartate dehydratase comprises an amino acid sequence having at least 90% sequence identity to SEQ ID NO: 954, the de novo expressed polypeptide having the enzymatic activity of (c) iminosuccinate reductase comprises an amino acid sequence having at least 90% sequence identity to a sequence selected from SEQ ID NO: 1-299, and the de novo expressed polypeptide having the enzymatic activity of (d) aspartate-glyoxylate transaminase comprises an amino acid sequence having at least 90% sequence identity to a sequence selected from SEQ ID NO: 300-599.

Even more preferably, in the inventive methods described herein, the de novo expressed polypeptide having the enzymatic activity of (a) erythro-β-hydroxyaspartate aldolase comprises an amino acid sequence having at least 95% sequence identity to SEQ ID NO: 953, the de novo expressed polypeptide having the enzymatic activity of (b) erythro-β-hydroxyaspartate dehydratase comprises an amino acid sequence having at least 95% sequence identity to SEQ ID NO: 954, the de novo expressed polypeptide having the enzymatic activity of (c) iminosuccinate reductase comprises an amino acid sequence having at least 95% sequence identity to a sequence selected from SEQ ID NO: 1-299, and the de novo expressed polypeptide having the enzymatic activity of (d) aspartate-glyoxylate transaminase comprises an amino acid sequence having at least 95% sequence identity to a sequence selected from SEQ ID NO: 300-599.

Even more preferably, in the inventive methods described herein, the de novo expressed polypeptide having the enzymatic activity of (a) erythro-β-hydroxyaspartate aldolase comprises an amino acid sequence having at least 97% sequence identity to SEQ ID NO: 953, the de novo expressed polypeptide having the enzymatic activity of (b) erythro-β-hydroxyaspartate dehydratase comprises an amino acid sequence having at least 97% sequence identity to SEQ ID NO: 954, the de novo expressed polypeptide having the enzymatic activity of (c) iminosuccinate reductase comprises an amino acid sequence having at least 97% sequence identity to a sequence selected from SEQ ID NO: 1-299, and the de novo expressed polypeptide having the enzymatic activity of (d) aspartate-glyoxylate transaminase comprises an amino acid sequence having at least 97% sequence identity to a sequence selected from SEQ ID NO: 300-599.

More preferably, in the inventive methods described herein, the de novo expressed polypeptide having the enzymatic activity of (a) erythro-β-hydroxyaspartate aldolase comprises an amino acid sequence having at least 99% sequence identity to SEQ ID NO: 953, the de novo expressed polypeptide having the enzymatic activity of (b) erythro-β-hydroxyaspartate dehydratase comprises an amino acid sequence having at least 99% sequence identity to SEQ ID NO: 954, the de novo expressed polypeptide having the enzymatic activity of (c) iminosuccinate reductase comprises an amino acid sequence having at least 99% sequence identity to a sequence selected from SEQ ID NO: 1-299, and the de novo expressed polypeptide having the enzymatic activity of (d) aspartate-glyoxylate transaminase comprises an amino acid sequence having at least 99% sequence identity to a sequence selected from SEQ ID NO: 300-599.

More preferably, in the inventive methods described herein, the de novo expressed polypeptide having the enzymatic activity of (a) erythro-β-hydroxyaspartate aldolase comprises the amino acid sequence SEQ ID NO: 953, the de novo expressed polypeptide having the enzymatic activity of (b) erythro-β-hydroxyaspartate dehydratase comprises the amino acid sequence SEQ ID NO: 954, the de novo expressed polypeptide having the enzymatic activity of (c) iminosuccinate reductase comprises the amino acid sequence selected from SEQ ID NO: 1-299, and the de novo expressed polypeptide having the enzymatic activity of (d) aspartate-glyoxylate transaminase comprises the amino acid sequence selected from SEQ ID NO: 300-599.

The β-hydroxyaspartate pathway (BHAP, FIG. 1) from *Paracoccus denitrificans* or other microorganisms can be implemented in different cellular compartments of a plant cell, such as peroxisomes, chloroplast, mitochondria and cytosol.

Therefore, one aspect of the invention is directed to a method for the production of a transgenic plant with altered photorespiration and improved $CO_2$ fixation, comprising introducing into a cell or tissue of said plant one or more nucleic acids encoding at least four polypeptides having the enzymatic activities of
  (a) erythro-β-hydroxyaspartate aldolase belonging to the EC class 4.1.3.14,
  (b) erythro-β-hydroxyaspartate dehydratase belonging to the EC class 4.3.1.20,
  (c) iminosuccinate reductase and
  (d) aspartate-glyoxylate transaminase,
wherein the introduction of said nucleic acid(s) results in a de novo expression of the at least four polypeptides having the enzymatic activities of
  (a) erythro-β-hydroxyaspartate aldolase belonging to the EC class 4.1.3.14,
  (b) erythro-β-hydroxyaspartate dehydratase belonging to the EC class 4.3.1.20,
  (c) iminosuccinate reductase and
  (d) aspartate-glyoxylate transaminase,
wherein the polypeptide having the enzymatic activity of (c) iminosuccinate reductase comprises an amino acid sequence selected from SEQ ID NO: 1-299, or an amino acid sequence having at least 80% sequence identity to a sequence selected from SEQ ID NO: 1-299;
the polypeptide having the enzymatic activity of (d) aspartate-glyoxylate transaminase comprises an amino acid sequence selected from SEQ ID NO: 300-599, or an amino acid sequence having at least 80% sequence identity to a sequence selected from SEQ ID NO: 300-599; and
wherein said polypeptides having the enzymatic activities (a)-(d) are localized in an cell organelle selected from peroxisomes, chloroplast, mitochondria and cytosol.

The BHAP implementation in plant peroxisomes shows some advantages compared to the other organelles. Indeed, photorespiration-derived glyoxylate is present at high concentration in peroxisomes. A second advantage of the BHAP implementation in peroxisomes is that the produced oxaloacetate or malate can thus be exported into the cytosol to enter gluconeogenesis or the TCA cycle anaplerotically without additional implementation of transport proteins. A third advantage is the small overlap between native metabolism in peroxisomes and the BHAP. Indeed, BHAP substrate and intermediate utilization by native peroxisomal metabolism is expected to be low. The before mentioned advantages of peroxisomal BHAP implementation suggests that peroxisomal implementation of the BHAP will have the strongest impact on plant growth.

Therefore, one embodiment of the invention is directed to a method for the production of a transgenic plant with altered photorespiration and improved $CO_2$ fixation, comprising introducing into a cell or tissue of said plant one or more nucleic acids encoding at least four polypeptides having the enzymatic activities of
  (a) erythro-β-hydroxyaspartate aldolase belonging to the EC class 4.1.3.14,
  (b) erythro-β-hydroxyaspartate dehydratase belonging to the EC class 4.3.1.20,
  (c) iminosuccinate reductase and
  (d) aspartate-glyoxylate transaminase,
wherein the introduction of said nucleic acid(s) results in a de novo expression of the at least four polypeptides having the enzymatic activities of
  (a) erythro-β-hydroxyaspartate aldolase belonging to the EC class 4.1.3.14,
  (b) erythro-β-hydroxyaspartate dehydratase belonging to the EC class 4.3.1.20,
  (c) iminosuccinate reductase and
  (d) aspartate-glyoxylate transaminase,
wherein the polypeptide having the enzymatic activity of (c) iminosuccinate reductase comprises an amino acid sequence selected from SEQ ID NO: 1-299, or an amino acid sequence having at least 80% sequence identity to a sequence selected from SEQ ID NO: 1-299;
the polypeptide having the enzymatic activity of (d) aspartate-glyoxylate transaminase comprises an amino acid sequence selected from SEQ ID NO: 300-599, or an amino acid sequence having at least 80% sequence identity to a sequence selected from SEQ ID NO: 300-599; and
wherein said polypeptides having the enzymatic activities (a)-(d) are localized in peroxisomes.

In order to target all four enzymes β-hydroxyaspartate aldolase (BHAA), β-hydroxyaspartate dehydratase (BHAD), iminosuccinate reductase (ISRed), and aspartate-glyoxylate aminotransferase (AsGAT) to plant peroxisomes, synthetic fusions with peroxisomal targeting sequences were generated. AsGAT, BHAD and ISRED were C-terminally fused with the three amino acid peroxisomal targeting signal 1 (PTS1; serine-lysine-leucine/SKL). C-terminal fusion of BHAA with PTS1 inactivated the enzyme and therefore, BHAA was N-terminally fused with the peroxisomal targeting signal 2 (PTS2; SEQ ID NO 951 (nucleic acid) and SEQ ID NO 952 (amino acid)) from *Arabidopsis* peroxisomal citrate synthase 3 (At2g42790). Thus, one embodiment of the invention is directed to a method for the production of a transgenic plant with altered photorespiration and improved $CO_2$ fixation, comprising introducing into a cell or tissue of said plant one or more nucleic acids encoding at least four polypeptides having the enzymatic activities of
  (a) erythro-β-hydroxyaspartate aldolase belonging to the EC class 4.1.3.14,
  (b) erythro-β-hydroxyaspartate dehydratase belonging to the EC class 4.3.1.20,
  (c) iminosuccinate reductase and
  (d) aspartate-glyoxylate transaminase,
wherein the introduction of said nucleic acid(s) results in a de novo expression of the four polypeptides having the enzymatic activities of
  (a) erythro-β-hydroxyaspartate aldolase belonging to the EC class 4.1.3.14,
  (b) erythro-β-hydroxyaspartate dehydratase belonging to the EC class 4.3.1.20,
  (c) iminosuccinate reductase and
  (d) aspartate-glyoxylate transaminase,
wherein the polypeptide having the enzymatic activity of (c) iminosuccinate reductase comprises an amino acid sequence selected from SEQ ID NO: 1-299, or an amino acid sequence having at least 80% sequence identity to a sequence selected from SEQ ID NO: 1-299;
the polypeptide having the enzymatic activity of (d) aspartate-glyoxylate transaminase comprises an amino acid sequence selected from SEQ ID NO: 300-599, or an amino acid sequence having at least 80% sequence identity to a sequence selected from SEQ ID NO: 300-599;
wherein said polypeptides having the enzymatic activities (a)-(d) comprise an amino acid sequence targeting said polypeptides to the peroxisomes,
wherein the (a) erythro-β-hydroxyaspartate aldolase belonging to the EC class 4.1.3.14 is C-terminally fused to a peroxisomal targeting signal 2 of SEQ ID NO: 952 and the polypeptides having the enzymatic activities (b)-(d) are N-terminally fused to a peroxisomal targeting signal 1 of amino acid sequence SKL.

It is to be understood that the de novo expressed polypeptides which were C-terminally or N-terminally fused to a target peptide may bear at the respective C-terminus or N-terminus the fused target peptide or other amino acid sequences, such as tags for immunoblot analysis.

Preferably, the de novo expressed (c) iminosuccinate reductase comprises an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to a sequence selected from SEQ ID NO: 1-299.

More preferably, the polypeptide having the enzymatic activity of (c) iminosuccinate reductase comprises an amino acid sequence selected from SEQ ID NO: 1, 7, 22, 25, 26, 39, 47, 58, 75, 123, 135, and 160, or an amino acid sequence having at least 80% sequence identity to a sequence selected from SEQ ID NO: 1, 7, 22, 25, 26, 39, 47, 58, 75, 123, 135, and 160.

Preferably, the de novo expressed (d) aspartate-glyoxylate transaminase comprises an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to a sequence selected from SEQ ID NO: 300-599.

More preferably, the polypeptide having the enzymatic activity of (c) iminosuccinate reductase comprises an amino acid sequence as set forth in SEQ ID NO: 135, or an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to said sequence; and the polypeptide having the enzymatic activity of (d) aspartate-glyoxylate transaminase comprises an amino acid sequence as set forth in SEQ ID NO: 433, or an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to said sequence.

The BHAP implementation in mitochondria and chloroplast requires additional engineering in comparison to the peroxisomes. As glyoxylate is low in chloroplasts and mitochondria, the establishing of the BHAP in these organelles requires the expression of glycolate dehydrogenase (EC 1.1.99.14) (enzymatic activity (e) for glyoxylate production).

In mitochondria, the oxaloacetate produced by the BHAP is directly metabolized by the TCA cycle, therefore establishing the BHAP in mitochondria requires de novo expression of the four polypeptides having the enzymatic activities of (a) erythro-β-hydroxyaspartate aldolase belonging to the EC class 4.1.3.14, (b) erythro-β-hydroxyaspartate dehydratase belonging to the EC class 4.3.1.20, (c) iminosuccinate reductase, and (d) aspartate-glyoxylate transaminase, and further of one polypeptide having the enzymatic activity of (e) glycolate dehydrogenase belonging to the EC class 1.1.99.14.

Therefore, one embodiment of the present invention is directed to a method for the production of a transgenic plant with altered photorespiration and improved $CO_2$ fixation, comprising introducing into a cell or tissue of said plant one or more nucleic acids encoding at least five polypeptides having the enzymatic activities of
(a) erythro-β-hydroxyaspartate aldolase belonging to the EC class 4.1.3.14,
(b) erythro-β-hydroxyaspartate dehydratase belonging to the EC class 4.3.1.20,
(c) iminosuccinate reductase,
(d) aspartate-glyoxylate transaminase, and
(e) glycolate dehydrogenase belonging to the EC class 1.1.99.14,
wherein the introduction of said nucleic acid(s) results in a de novo expression of the at least five polypeptides having the enzymatic activities of
(a) erythro-β-hydroxyaspartate aldolase belonging to the EC class 4.1.3.14,
(b) erythro-β-hydroxyaspartate dehydratase belonging to the EC class 4.3.1.20,
(c) iminosuccinate reductase,
(d) aspartate-glyoxylate transaminase, and
(e) glycolate dehydrogenase belonging to the EC class 1.1.99.14,
wherein the polypeptide having the enzymatic activity of (c) iminosuccinate reductase comprises an amino acid sequence selected from SEQ ID NO: 1-299, or an amino acid sequence having at least 80% sequence identity to a sequence selected from SEQ ID NO: 1-299;
and the polypeptide having the enzymatic activity of (d) aspartate-glyoxylate transaminase comprises an amino acid sequence selected from SEQ ID NO: 300-599, or an amino acid sequence having at least 80% sequence identity to a sequence selected from SEQ ID NO: 300-599, and wherein said polypeptides having the enzymatic activities (a)-(e) are localized in mitochondria.

In order to target all five polypeptides having the enzymatic activities (a) erythro-β-hydroxyaspartate aldolase, (b) erythro-β-hydroxyaspartate dehydratase, (c) iminosuccinate reductase, (d) aspartate-glyoxylate transaminase, and (e) glycolate dehydrogenase to plant mitochondria they can be synthetically fused with mitochondria targeting sequences. In this way, the five polypeptides with the enzymatic activities (a)-(e) are fused to N-terminal targeting sequences such as that from *Arabidopsis* serine hydroxymethyltransferase 1 (At4g37930), having nucleic acid sequence and amino acid sequence of SEQ ID NO 918 and 919, respectively. Thus, one embodiment of the invention is directed to a method for the production of a transgenic plant with altered photorespiration and improved $CO_2$ fixation, comprising introducing into a cell or tissue of said plant one or more nucleic acids encoding at least five polypeptides having the enzymatic activities of
(a) erythro-β-hydroxyaspartate aldolase belonging to the EC class 4.1.3.14,
(b) erythro-β-hydroxyaspartate dehydratase belonging to the EC class 4.3.1.20,
(c) iminosuccinate reductase,
(d) aspartate-glyoxylate transaminase, and
(e) glycolate dehydrogenase belonging to the EC class 1.1.99.14, wherein the introduction of said nucleic acid(s) results in a de novo expression of the at least five polypeptides having the enzymatic activities of
  (a) erythro-β-hydroxyaspartate aldolase belonging to the EC class 4.1.3.14,
  (b) erythro-β-hydroxyaspartate dehydratase belonging to the EC class 4.3.1.20,
  (c) iminosuccinate reductase
  (d) aspartate-glyoxylate transaminase, and
  (e) glycolate dehydrogenase belonging to the EC class 1.1.99.14,
wherein the polypeptide having the enzymatic activity of (c) iminosuccinate reductase comprises an amino acid sequence selected from SEQ ID NO: 1-299, or an amino acid sequence having at least 80% sequence identity to a sequence selected from SEQ ID NO: 1-299;
and the polypeptide having the enzymatic activity of (d) aspartate-glyoxylate transaminase comprises an amino acid sequence selected from SEQ ID NO: 300-599, or an amino acid sequence having at least 80% sequence identity to a sequence selected from SEQ ID NO: 300-599, and
wherein said polypeptides having the enzymatic activities (a)-(e) comprise an amino acid sequence targeting said polypeptides to the mitochondria.

In particular, one embodiment of the invention is directed to a method for the production of a transgenic plant with altered photorespiration and improved $CO_2$ fixation, comprising introducing into a cell or tissue of said plant one or more nucleic acids encoding at least five polypeptides having the enzymatic activities of
  (a) erythro-β-hydroxyaspartate aldolase belonging to the EC class 4.1.3.14,
  (b) erythro-β-hydroxyaspartate dehydratase belonging to the EC class 4.3.1.20,
  (c) iminosuccinate reductase
  (d) aspartate-glyoxylate transaminase, and
  (e) glycolate dehydrogenase belonging to the EC class 1.1.99.14,
wherein the introduction of said nucleic acid(s) results in a de novo expression of the at least five polypeptides having the enzymatic activities of
  (a) erythro-β-hydroxyaspartate aldolase belonging to the EC class 4.1.3.14,
  (b) erythro-β-hydroxyaspartate dehydratase belonging to the EC class 4.3.1.20,
  (c) iminosuccinate reductase,
  (d) aspartate-glyoxylate transaminase, and
  (e) glycolate dehydrogenase belonging to the EC class 1.1.99.14,
wherein the polypeptide having the enzymatic activity of (c) iminosuccinate reductase comprises an amino acid sequence selected from SEQ ID NO: 1-299, or an amino acid sequence having at least 80% sequence identity to a sequence selected from SEQ ID NO: 1-299;
and the polypeptide having the enzymatic activity of (d) aspartate-glyoxylate transaminase comprises an amino acid sequence selected from SEQ ID NO: 300-599, or an amino acid sequence having at least 80% sequence identity to a sequence selected from SEQ ID NO: 300-599,
wherein said polypeptides having the enzymatic activities (a)-(e) comprise an amino acid sequence targeting said polypeptides to the mitochondria, and
wherein said polypeptides having the enzymatic activities (a)-(e) are N-terminally fused to a serine hydroxymethyl-transferase 1 target peptide of SEQ ID NO: 919.

It is to be understood that the de novo expressed polypeptides which were N-terminally fused to a target peptide may bear at the respective N-terminus the fused target peptide or other amino acid sequences, such as tags for immunoblot analysis.

Preferably, the de novo expressed (c) iminosuccinate reductase comprises an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to a sequence selected from SEQ ID NO: 1-299.

More preferably, the polypeptide having the enzymatic activity of (c) iminosuccinate reductase comprises an amino acid sequence selected from SEQ ID NO: 1, 7, 22, 25, 26, 39, 47, 58, 75, 123, 135, and 160, or an amino acid sequence having at least 80% sequence identity to a sequence selected from SEQ ID NO: 1, 7, 22, 25, 26, 39, 47, 58, 75, 123, 135, and 160.

Preferably, the de novo expressed (d) aspartate-glyoxylate transaminase comprises an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to a sequence selected from SEQ ID NO: 300-599.

More preferably, the polypeptide having the enzymatic activity of (c) iminosuccinate reductase comprises an amino acid sequence as set forth in SEQ ID NO: 135, or an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to said sequence; and the polypeptide having the enzymatic activity of (d) aspartate-glyoxylate transaminase comprises an amino acid sequence as set forth in SEQ ID NO: 433, or an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to said sequence.

The BHAP implementation in chloroplasts requires, in addition to the further expression of the enzymatic activity (e) glycolate dehydrogenase, also an ATP-dependent phosphoenolpyruvate carboxykinase (PEPCK, EC 4.1.1.49) (enzymatic activity (f)) for downstream metabolism of oxaloacetate. Oxaloacetate produced by the BHAP will be decarboxylated by PEPCK and generated phosphoenolpyruvate will be converted into 2-phosphoglycerate by plastidial enolase, ENO1 (At1g74030) and further into 3-phosphoglycerate by plastidial phosphoglycerate mutase (PGM, At5g51820). Produced 3-phosphoglycerate subsequently enters photosynthetic carbon metabolism.

In view of the these considerations, establishing the BHAP in chloroplasts requires de novo expression of the four polypeptides having the enzymatic activities of (a) erythro-β-hydroxyaspartate aldolase belonging to the EC class 4.1.3.14, (b) erythro-β-hydroxyaspartate dehydratase belonging to the EC class 4.3.1.20, (c) iminosuccinate reductase, and (d) aspartate-glyoxylate transaminase, and further of one polypeptide having the enzymatic activity of (e) glycolate dehydrogenase belonging to the EC class 1.1.99.14, and of one polypeptide having the enzymatic activity of (f) phosphoenolpyruvate carboxykinase belonging to the EC class 4.1.3.14.

Therefore, a further embodiment of the present invention is directed to a method for the production of a transgenic plant with altered photorespiration and improved $CO_2$ fixation, comprising introducing into a cell or tissue of said plant one or more nucleic acids encoding at least six polypeptides having the enzymatic activities of
- (a) erythro-β-hydroxyaspartate aldolase belonging to the EC class 4.1.3.14,
- (b) erythro-β-hydroxyaspartate dehydratase belonging to the EC class 4.3.1.20,
- (c) iminosuccinate reductase,
- (d) aspartate-glyoxylate transaminase,
- (e) glycolate dehydrogenase belonging to the EC class 1.1.99.14, and
- (f) phosphoenolpyruvate carboxykinase belonging to the EC class EC 4.1.1.49, wherein the introduction of said nucleic acid(s) results in a de novo expression of the at least six polypeptides having the enzymatic activities of
- (a) erythro-β-hydroxyaspartate aldolase belonging to the EC class 4.1.3.14,
- (b) erythro-β-hydroxyaspartate dehydratase belonging to the EC class 4.3.1.20,
- (c) iminosuccinate reductase,
- (d) aspartate-glyoxylate transaminase,
- (e) glycolate dehydrogenase belonging to the EC class 1.1.99.14, and
- (f) phosphoenolpyruvate carboxykinase belonging to the EC class EC 4.1.1.49, wherein the polypeptide having the enzymatic activity of (c) iminosuccinate reductase comprises an amino acid sequence selected from SEQ ID NO: 1-299, or an amino acid sequence having at least 80% sequence identity to a sequence selected from SEQ ID NO: 1-299;
and the polypeptide having the enzymatic activity of (d) aspartate-glyoxylate transaminase comprises an amino acid sequence selected from SEQ ID NO: 300-599, or an amino acid sequence having at least 80% sequence identity to a sequence selected from SEQ ID NO: 300-599,
and wherein said polypeptides having the enzymatic activities (a)-(f) are localized in chloroplasts.

In order to target all six polypeptides having the enzymatic activities (a) erythro-β-hydroxyaspartate aldolase, (b) erythro-β-hydroxyaspartate dehydratase, (c) iminosuccinate reductase, (d) aspartate-glyoxylate transaminase, (e) glycolate dehydrogenase, and (f) phosphoenolpyruvate carboxykinase to plant chloroplasts they can be synthetically fused with chloroplasts targeting sequences. In this way, the six polypeptides with the enzymatic activities (a)-(f) were fused to N-terminal targeting sequences such as that from *Arabidopsis* ferredoxin-2 (At1g60950), having nucleic acid sequence and amino acid sequence of SEQ ID NOs 916 and 917, respectively. Thus, one embodiment of the invention is directed to a method for the production of a transgenic plant with altered photorespiration and improved $CO_2$ fixation, comprising introducing into a cell or tissue of said plant one or more nucleic acids encoding at least six polypeptides having the enzymatic activities of
- (a) erythro-β-hydroxyaspartate aldolase belonging to the EC class 4.1.3.14,
- (b) erythro-β-hydroxyaspartate dehydratase belonging to the EC class 4.3.1.20,
- (c) iminosuccinate reductase,
- (d) aspartate-glyoxylate transaminase,
- (e) glycolate dehydrogenase belonging to the EC class 1.1.99.14, and
- (f) phosphoenolpyruvate carboxykinase belonging to the EC class EC 4.1.1.49, wherein the introduction of said nucleic acid(s) results in a de novo expression of the at least six polypeptides having the enzymatic activities of
- (a) erythro-β-hydroxyaspartate aldolase belonging to the EC class 4.1.3.14,
- (b) erythro-β-hydroxyaspartate dehydratase belonging to the EC class 4.3.1.20,
- (c) iminosuccinate reductase,
- (d) aspartate-glyoxylate transaminase,
- (e) glycolate dehydrogenase belonging to the EC class 1.1.99.14, and
- (f) phosphoenolpyruvate carboxykinase belonging to the EC class 4.1.1.49, wherein the polypeptide having the enzymatic activity of (c) iminosuccinate reductase comprises an amino acid sequence selected from SEQ ID NO: 1-299, or an amino acid sequence having at least 80% sequence identity to a sequence selected from SEQ ID NO: 1-299;
and the polypeptide having the enzymatic activity of (d) aspartate-glyoxylate transaminase comprises an amino acid sequence selected from SEQ ID NO: 300-599, or an amino acid sequence having at least 80% sequence identity to a sequence selected from SEQ ID NO: 300-599, and
wherein said polypeptides having the enzymatic activities (a)-(f) comprise an amino acid sequence targeting said polypeptides to the chloroplasts.

In particular, one embodiment of the invention is directed to a method for the production of a transgenic plant with altered photorespiration and improved $CO_2$ fixation, comprising introducing into a cell or tissue of said plant one or more nucleic acids encoding at least six polypeptides having the enzymatic activities of
- (a) erythro-β-hydroxyaspartate aldolase belonging to the EC class 4.1.3.14,
- (b) erythro-β-hydroxyaspartate dehydratase belonging to the EC class 4.3.1.20,
- (c) iminosuccinate reductase,
- (d) aspartate-glyoxylate transaminase, and
- (e) glycolate dehydrogenase belonging to the EC class 1.1.99.14, wherein the introduction of said nucleic acid(s) results in a de novo expression of the at least six polypeptides having the enzymatic activities of
- (a) erythro-β-hydroxyaspartate aldolase belonging to the EC class 4.1.3.14,
- (b) erythro-β-hydroxyaspartate dehydratase belonging to the EC class 4.3.1.20,
- (c) iminosuccinate reductase,
- (d) aspartate-glyoxylate transaminase, and
- (e) glycolate dehydrogenase belonging to the EC class 1.1.99.14, wherein the polypeptide having the enzymatic activity of (c) iminosuccinate reductase comprises an amino acid sequence selected from SEQ ID NO: 1-299, or an amino acid sequence having at least 80% sequence identity to a sequence selected from SEQ ID NO: 1-299;

and the polypeptide having the enzymatic activity of (d) aspartate-glyoxylate transaminase comprises an amino acid sequence selected from SEQ ID NO: 300-599, or an amino acid sequence having at least 80% sequence identity to a sequence selected from SEQ ID NO: 300-599,
wherein said polypeptides having the enzymatic activities (a)-(f) comprise an amino acid sequence targeting said polypeptides to the chloroplasts, and wherein said polypeptides having the enzymatic activities (a)-(f) are N-terminally fused to Arabidopsis Ferredoxin-2 chloroplastic target peptide of SEQ ID NO: 917.

It is to be understood that the de novo expressed polypeptides which were N-terminally fused to a target peptide may bear at the respective N-terminus the fused target peptide or other amino acid sequences, such as tags for immunoblot analysis.

Preferably, the de novo expressed (c) iminosuccinate reductase comprises an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to a sequence selected from SEQ ID NO: 1-299.

More preferably, the polypeptide having the enzymatic activity of (c) iminosuccinate reductase comprises an amino acid sequence selected from SEQ ID NO: 1, 7, 22, 25, 26, 39, 47, 58, 75, 123, 135, and 160, or an amino acid sequence having at least 80% sequence identity to a sequence selected from SEQ ID NO: 1, 7, 22, 25, 26, 39, 47, 58, 75, 123, 135, and 160.

Preferably, the de novo expressed (d) aspartate-glyoxylate transaminase comprises an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to a sequence selected from SEQ ID NO: 300-599.

More preferably, the polypeptide having the enzymatic activity of (c) iminosuccinate reductase comprises an amino acid sequence as set forth in SEQ ID NO: 135, or an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to said sequence; and the polypeptide having the enzymatic activity of (d) aspartate-glyoxylate transaminase comprises an amino acid sequence as set forth in SEQ ID NO: 433, or an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to said sequence.

Although the decarboxylation of oxaloacetate in the chloroplast might positively influence $CO_2$ assimilation, the PEPCK step requires one ATP per produced phosphoenolpyruvate, thereby weakening the energy-conserving principle of the BHAP. Furthermore, produced PEP might be distributed between 3-phosphoglycerate production and the shikimate pathway for aromatic amino acid biosynthesis. Alternatively, oxaloacetate is reduced by a NAD(P)-dependent malate dehydrogenase to produce malate that can be exported from the chloroplast via Dit1 (At5g12860). Although the first proposed strategy for BHAP expression in the chloroplast requires two more enzymes in addition to the BHAP core enzymes, the chloroplastic decarboxylation of oxaloacetate and the production of 3-phosphoglycerate that can directly enter photosynthetic carbon metabolism might be advantageous.

Moreover, the BHAP can be also implemented in plant cell cytosol. The localization of the four polypeptides having the enzymatic activities (a) erythro-β-hydroxyaspartate aldolase, (b) erythro-β-hydroxyaspartate dehydratase, (c) iminosuccinate reductase, and (d) aspartate-glyoxylate transaminase to plant cell cytosol does not require the presence of particular targeting sequences. Therefore, another embodiment of the invention is directed to a method for the production of a transgenic plant with altered photorespiration and improved $CO_2$ fixation, comprising introducing into a cell or tissue of said plant one or more nucleic acids encoding at least four polypeptides having the enzymatic activities of
(a) erythro-β-hydroxyaspartate aldolase belonging to the EC class 4.1.3.14,
(b) erythro-β-hydroxyaspartate dehydratase belonging to the EC class 4.3.1.20,
(c) iminosuccinate reductase and
(d) aspartate-glyoxylate transaminase,
wherein the introduction of said nucleic acid(s) results in a de novo expression of the at least four polypeptides having the enzymatic activities of
(a) erythro-β-hydroxyaspartate aldolase belonging to the EC class 4.1.3.14,
(b) erythro-β-hydroxyaspartate dehydratase belonging to the EC class 4.3.1.20,
(c) iminosuccinate reductase and
(d) aspartate-glyoxylate transaminase,
wherein the polypeptide having the enzymatic activity of (c) iminosuccinate reductase comprises an amino acid sequence selected from SEQ ID NO: 1-299, or an amino acid sequence having at least 80% sequence identity to a sequence selected from SEQ ID NO: 1-299;
and the polypeptide having the enzymatic activity of (d) aspartate-glyoxylate transaminase comprises an amino acid sequence selected from SEQ ID NO: 300-599, or an amino acid sequence having at least 80% sequence identity to a sequence selected from SEQ ID NO: 300-599, and
wherein said polypeptides having the enzymatic activities (a)-(d) are localized in cytosol.

In particular, another embodiment of the invention is directed to a method for the production of a transgenic plant with altered photorespiration and improved $CO_2$ fixation, comprising introducing into a cell or tissue of said plant one or more nucleic acids encoding at least four polypeptides having the enzymatic activities of
(a) erythro-β-hydroxyaspartate aldolase belonging to the EC class 4.1.3.14,
(b) erythro-β-hydroxyaspartate dehydratase belonging to the EC class 4.3.1.20,
(c) iminosuccinate reductase and
(d) aspartate-glyoxylate transaminase, wherein the introduction of said nucleic acid(s) results in a de novo expression of the four polypeptides having the enzymatic activities of
- (a) erythro-β-hydroxyaspartate aldolase belonging to the EC class 4.1.3.14,
- (b) erythro-β-hydroxyaspartate dehydratase belonging to the EC class 4.3.1.20,
- (c) iminosuccinate reductase and
- (d) aspartate-glyoxylate transaminase, wherein the polypeptide having the enzymatic activity of (c) iminosuccinate reductase comprises an amino acid sequence selected from SEQ ID NO: 1-299, or an amino acid sequence having at least 80% sequence identity to a sequence selected from SEQ ID NO: 1-299;

and the polypeptide having the enzymatic activity of (d) aspartate-glyoxylate transaminase comprises an amino acid sequence selected from SEQ ID NO: 300-599, or an amino acid sequence having at least 80% sequence identity to a sequence selected from SEQ ID NO: 300-599, wherein said polypeptides having the enzymatic activities (a)-(d) are localized in cytosol; and wherein said polypeptides having the enzymatic activities (a)-(f) lack of a target sequence.

Preferably, the de novo expressed (c) iminosuccinate reductase comprises an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to a sequence selected from SEQ ID NO: 1-299.

More preferably, the polypeptide having the enzymatic activity of (c) iminosuccinate reductase comprises an amino acid sequence selected from SEQ ID NO: 1, 7, 22, 25, 26, 39, 47, 58, 75, 123, 135, and 160, or an amino acid sequence having at least 80% sequence identity to a sequence selected from SEQ ID NO: 1, 7, 22, 25, 26, 39, 47, 58, 75, 123, 135, and 160.

Preferably, the de novo expressed (d) aspartate-glyoxylate transaminase comprises an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to a sequence selected from SEQ ID NO: 300-599.

More preferably, the polypeptide having the enzymatic activity of (c) iminosuccinate reductase comprises an amino acid sequence as set forth in SEQ ID NO: 135, or an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to said sequence; and the polypeptide having the enzymatic activity of (d) aspartate-glyoxylate transaminase comprises an amino acid sequence as set forth in SEQ ID NO: 433, or an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to said sequence.

Codon Optimization

In designing the nucleic acid molecules of this invention for encoding four polypeptides having the enzymatic activities of (a) erythro-β-hydroxyaspartate aldolase belonging to the EC class 4.1.3.14, (b) erythro-β-hydroxyaspartate dehydratase belonging to the EC class 4.3.1.20, (c) iminosuccinate reductase and (d) aspartate-glyoxylate transaminase, the nucleic acids from *Paracoccus denitrificans* or other Proteobacteria are modified in order to contain codons preferred by highly expressed plant genes in a procedure referred to as "codon optimization". Codon preferences for monocot and dicot plants have been taught by Murray et al., 1989, "Codon usage in plant genes", which characterized the codon usage (frequency of codon used for each amino acid except Met and Trp) in 207 plant gene sequences from 53 monocot and 154 dicot genes (Table 3, 4, 6, 7). Murray et al. showed that the relative use of synonymous codons differ between taxonomic groups, primarily in the use of G+C in the degenerate third base.

Moreover the patent EP0359472B1 describes in detail how to prepare a plant optimized sequence of the invention. In the synthetic nucleic acids, codons used to specify a given amino acid are selected on the basis of the distribution frequency of codon usage employed in highly expressed plant genes to specify that amino acid. In the synthetic genes, codons used to specify a given amino acid are selected with regard to the distribution frequency of codon usage employed in highly expressed plant genes to specify that amino acid. As is appreciated by those skilled in the art, the distribution frequency of codon usage utilized in the nucleic acid molecules is a determinant of the level of expression. Hence, the nucleic acid molecules are designed such that its distribution frequency of codon usage deviates, preferably, no more than 25% from that of highly expressed plant genes and, more preferably, no more than about 10%. In addition, consideration is given to the percentage G+C content of the degenerate third base (monocotyledons appear to favor G+C in this position, whereas dicotyledons do not). It is also recognized that the XCG nucleotide is the least preferred codon in dicots whereas the XTA codon is avoided in both monocots and dicots. Moreover, the nucleic acid sequence is modified to attain an A+T content in nucleotide base composition substantially that found in plants, and also to eliminate sequences that cause destabilization, inappropriate polyadenylation, degradation and termination of RNA and to avoid sequences that constitute secondary structure hairpins and RNA splice sites.

In the examples of the present invention, all four required genes of the BHAP were codon-optimized for expression in the respective plants, and in particular in cell peroxisomes, by gene synthesis (Sigma Aldrich, Germany). The examples disclosed herein show that the four enzymes were expressed in peroxisomes of *Nicotiana benthamiana* (*N. benthamiana*) (FIG. 2) and were functionally active in *N. benthamiana* leaf extracts (FIG. 3-8).

In one embodiment, the implemented genes of the BHAP were codon-optimized for expression in the respective plant. Thus, in one embodiment, the method for the production of a transgenic plant with altered photorespiration and improved $CO_2$ fixation, comprises introducing into a cell or tissue of said plant one or more codon-optimized nucleic acids encoding at least four polypeptides having the enzymatic activities of (a) erythro-β-hydroxyaspartate aldolase belonging to the EC class 4.1.3.14,
(b) erythro-β-hydroxyaspartate dehydratase belonging to the EC class 4.3.1.20,
(c) iminosuccinate reductase and
(d) aspartate-glyoxylate transaminase, wherein the introduction of said nucleic acid(s) results in a de novo expression of the at least four polypeptides having the enzymatic activities of (a) erythro-β-hydroxyaspartate aldolase belonging to the EC class 4.1.3.14,
(b) erythro-β-hydroxyaspartate dehydratase belonging to the EC class 4.3.1.20,
(c) iminosuccinate reductase and
(d) aspartate-glyoxylate transaminase, wherein the polypeptide having the enzymatic activity of (c) iminosuccinate reductase comprises an amino acid sequence selected from SEQ ID NO: 1-299, or an amino acid sequence having at least 80% sequence identity to a sequence selected from SEQ ID NO: 1-299;

and the polypeptide having the enzymatic activity of (d) aspartate-glyoxylate transaminase comprises an amino acid sequence selected from SEQ ID NO: 300-599, or an amino acid sequence having at least 80% sequence identity to a sequence selected from SEQ ID NO: 300-599, and wherein said nucleic acid(s) are codon-optimized for expression in the transgenic plant.

In one embodiment, the implemented genes of the BHAP were codon-optimized for expression in *Arabidopsis thaliana*. Therefore when implementing the BHAP in *Arabidopsis* and in higher plants with similar codon usage, the nucleic acids encoding the polypeptides having the enzymatic activities of (a) erythro-β-hydroxyaspartate aldolase, (b) erythro-β-hydroxyaspartate dehydratase, (c) iminosuccinate reductase and (d) aspartate-glyoxylate transaminase are codon-optimized for expression in *Arabidopsis thaliana*. Thus, in one embodiment, the method for the production of a transgenic plant with altered photorespiration and improved $CO_2$ fixation, comprises introducing into a cell or tissue of said plant one or more nucleic acids encoding at least four polypeptides having the enzymatic activities of (a) erythro-β-hydroxyaspartate aldolase belonging to the EC class 4.1.3.14,
(b) erythro-β-hydroxyaspartate dehydratase belonging to the EC class 4.3.1.20,
(c) iminosuccinate reductase and
(d) aspartate-glyoxylate transaminase, wherein the introduction of said nucleic acid(s) results in a de novo expression of the at least four polypeptides having the enzymatic activities of (a) erythro-β-hydroxyaspartate aldolase belonging to the EC class 4.1.3.14,
(b) erythro-β-hydroxyaspartate dehydratase belonging to the EC class 4.3.1.20,
(c) iminosuccinate reductase and
(d) aspartate-glyoxylate transaminase, wherein the polypeptide having the enzymatic activity of (c) iminosuccinate reductase comprises an amino acid sequence selected from SEQ ID NO: 1-299, or an amino acid sequence having at least 80% sequence identity to a sequence selected from SEQ ID NO: 1-299;

and the polypeptide having the enzymatic activity of (d) aspartate-glyoxylate transaminase comprises an amino acid sequence selected from SEQ ID NO: 300-599, or an amino acid sequence having at least 80% sequence identity to a sequence selected from SEQ ID NO: 300-599, and wherein said nucleic acid(s) are codon-optimized for expression in *Arabidopsis thaliana*.

Preferably, the method for the production of a transgenic plant with altered photorespiration and improved $CO_2$ fixation, comprises introducing into a cell or tissue of said plant one or more nucleic acids encoding at least four polypeptides having the enzymatic activities of (a) erythro-β-hydroxyaspartate aldolase belonging to the EC class 4.1.3.14,
(b) erythro-β-hydroxyaspartate dehydratase belonging to the EC class 4.3.1.20,
(c) iminosuccinate reductase and
(d) aspartate-glyoxylate transaminase, wherein the introduction of said nucleic acid(s) results in a de novo expression of the at least four polypeptides having the enzymatic activities of (a) erythro-β-hydroxyaspartate aldolase belonging to the EC class 4.1.3.14,
(b) erythro-β-hydroxyaspartate dehydratase belonging to the EC class 4.3.1.20,
(c) iminosuccinate reductase and
(d) aspartate-glyoxylate transaminase, wherein the at least four polypeptides comprise an amino acid sequence as set forth in SEQ ID NO: 955-958, respectively, or an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to said sequences.

Preferably, the nucleic acids encoding the polypeptides having the enzymatic activities of (a) erythro-β-hydroxyaspartate aldolase, (b) erythro-β-hydroxyaspartate dehydratase, (c) iminosuccinate reductase and (d) aspartate-glyoxylate transaminase comprise a polynucleotide sequence as set forth in SEQ ID NOs 959-962, respectively, or a polynucleotide sequence having at least 80% sequence identity to said sequences. Thus, in one embodiment, the method for the production of a transgenic plant with altered photorespiration and improved $CO_2$ fixation, comprises introducing into a cell or tissue of said plant one or more nucleic acids encoding at least four polypeptides having the enzymatic activities of (a) erythro-β-hydroxyaspartate aldolase belonging to the EC class 4.1.3.14,
(b) erythro-β-hydroxyaspartate dehydratase belonging to the EC class 4.3.1.20,
(c) iminosuccinate reductase and
(d) aspartate-glyoxylate transaminase, wherein the introduction of said nucleic acid(s) results in a de novo expression of the at least four polypeptides having the enzymatic activities of (a) erythro-β-hydroxyaspartate aldolase belonging to the EC class 4.1.3.14,
(b) erythro-β-hydroxyaspartate dehydratase belonging to the EC class 4.3.1.20,
(c) iminosuccinate reductase and
(d) aspartate-glyoxylate transaminase, wherein the at least four polypeptides comprise an amino acid sequence as set forth in SEQ ID NOs: 953, 954, 135, and 433, respectively, and the nucleic acid(s) encoding the polypeptides having the enzymatic activities of (a) erythro-β-hydroxyaspartate aldolase, (b) erythro-β-hydroxyaspartate dehydratase, (c) iminosuccinate reductase and (d) aspartate-glyoxylate transaminase comprise a nucleic acid sequence as set forth in SEQ ID NOs 959-962, respectively; or wherein the at least four polypeptides comprise an amino acid sequence having at least 80% sequence identity to SEQ ID NOs: 953, 954, 135, and 433 respectively, and the nucleic acid(s) encoding the polypeptides having the enzymatic activities of (a) erythro-β-hydroxyaspartate aldolase, (b) erythro-β-hydroxyaspartate dehydratase, (c) iminosuccinate reductase and (d) aspartate-glyoxylate transaminase comprise a nucleic acid sequence having at least 80% sequence identity to SEQ ID NOs 959-962, respectively.

Alternatively, for the implementation of the BHAP in the cytosol, the nucleic acids encoding the polypeptides having the enzymatic activities of (a) erythro-β-hydroxyaspartate aldolase, (b) erythro-β-hydroxyaspartate dehydratase, (c) iminosuccinate reductase and (d) aspartate-glyoxylate transaminase comprise a polynucleotide sequence as set forth in SEQ ID NOs 963-966, respectively, or a polynucleotide sequence having at least 80% sequence identity to said sequences, respectively. Thus, in one embodiment, the method for the production of a transgenic plant with altered photorespiration and improved $CO_2$ fixation, comprises introducing into a cell or tissue of said plant one or more nucleic acids encoding at least four polypeptides having the enzymatic activities of
  (a) erythro-β-hydroxyaspartate aldolase belonging to the EC class 4.1.3.14,
  (b) erythro-β-hydroxyaspartate dehydratase belonging to the EC class 4.3.1.20,
  (c) iminosuccinate reductase and
  (d) aspartate-glyoxylate transaminase,
wherein the introduction of said nucleic acid(s) results in a de novo expression of the at least four polypeptides having the enzymatic activities of
  (a) erythro-β-hydroxyaspartate aldolase belonging to the EC class 4.1.3.14,
  (b) erythro-β-hydroxyaspartate dehydratase belonging to the EC class 4.3.1.20,
  (c) iminosuccinate reductase and
  (d) aspartate-glyoxylate transaminase,
wherein the at least four polypeptides comprise an amino acid sequence as set forth in SEQ ID NOs: 135, 433, 953 and 954, respectively, and the nucleic acid(s) encoding the polypeptides having the enzymatic activities of (a) erythro-β-hydroxyaspartate aldolase, (b) erythro-β-hydroxyaspartate dehydratase, (c) iminosuccinate reductase and (d) aspartate-glyoxylate transaminase comprise a nucleic acid sequence as set forth in SEQ ID NOs 963-966, respectively; or wherein the at least four polypeptides comprise an amino acid sequence having at least 80% sequence identity to SEQ ID NO: 135, 433, 953 and 954, respectively, and the nucleic acid(s) encoding the polypeptides having the enzymatic activities of (a) erythro-β-hydroxyaspartate aldolase, (b) erythro-β-hydroxyaspartate dehydratase, (c) iminosuccinate reductase and (d) aspartate-glyoxylate transaminase comprise a nucleic acid sequence having at least 80% sequence identity to SEQ ID NOs 963-966, respectively.

C3 Plants

The method of the present invention can be applied to any C3 plant, which fix and reduce inorganic $CO_2$ into organic compounds using only the C3 pathway in photosynthesis, including but not limited to *Helianthus annuus*, *Brassica napus*, *Camelina sativa*, *Oryza sativa*, *Hordeum vulgare*, *Triticum* spp., *Avena sativa*, *Solanum lycopersicum*, *Solanum tuberosum*, *Glycine max*, *Beta vulgaris*, *Nicotiana tabacum*, and *Arabidopsis thaliana*.

Thus, in one embodiment of the present invention, the method for the production of a transgenic plant with altered photorespiration and improved $CO_2$ fixation, comprises introducing into a cell or tissue of said plant one or more nucleic acids encoding at least four polypeptides having the enzymatic activities of
  (a) erythro-β-hydroxyaspartate aldolase belonging to the EC class 4.1.3.14,
  (b) erythro-β-hydroxyaspartate dehydratase belonging to the EC class 4.3.1.20,
  (c) iminosuccinate reductase and
  (d) aspartate-glyoxylate transaminase,
wherein the introduction of said nucleic acid(s) results in a de novo expression of the at least four polypeptides having the enzymatic activities of
  (a) erythro-β-hydroxyaspartate aldolase belonging to the EC class 4.1.3.14,
  (b) erythro-β-hydroxyaspartate dehydratase belonging to the EC class 4.3.1.20,
  (c) iminosuccinate reductase and
  (d) aspartate-glyoxylate transaminase,
wherein the polypeptide having the enzymatic activity of (c) iminosuccinate reductase comprises an amino acid sequence selected from SEQ ID NO: 1-299, or an amino acid sequence having at least 80% sequence identity to a sequence selected from SEQ ID NO: 1-299;
the polypeptide having the enzymatic activity of (d) aspartate-glyoxylate transaminase comprises an amino acid sequence selected from SEQ ID NO: 300-599, or an amino acid sequence having at least 80% sequence identity to a sequence selected from SEQ ID NO: 300-599,
and wherein the plant is a C3 plant.

Thus, in one embodiment of the present invention, the method for the production of a transgenic plant with altered photorespiration and improved $CO_2$ fixation, comprises introducing into a cell or tissue of said plant one or more nucleic acids encoding at least four polypeptides having the enzymatic activities of
  (a) erythro-β-hydroxyaspartate aldolase belonging to the EC class 4.1.3.14,
  (b) erythro-β-hydroxyaspartate dehydratase belonging to the EC class 4.3.1.20,
  (c) iminosuccinate reductase and
  (d) aspartate-glyoxylate transaminase,
wherein the introduction of said nucleic acid(s) results in a de novo expression of the at least four polypeptides having the enzymatic activities of
  (a) erythro-β-hydroxyaspartate aldolase belonging to the EC class 4.1.3.14,
  (b) erythro-β-hydroxyaspartate dehydratase belonging to the EC class 4.3.1.20,
  (c) iminosuccinate reductase and
  (d) aspartate-glyoxylate transaminase,
wherein the polypeptide having the enzymatic activity of (c) iminosuccinate reductase comprises an amino acid sequence selected from SEQ ID NO: 1-299, or an amino acid sequence having at least 80% sequence identity to a sequence selected from SEQ ID NO: 1-299; the polypeptide having the enzymatic activity of (d) aspartate-glyoxylate transaminase comprises an amino acid sequence selected from SEQ ID NO: 300-599, or an amino acid sequence having at least 80% sequence identity to a sequence selected from SEQ ID NO: 300-599,
and wherein the plant is selected from *Helianthus annuus*, *Brassica napus*, *Camelina sativa*, *Oryza sativa*, *Hordeum*

*vulgare, Triticum* spp., *Avena sativa, Solanum lycopersicum, Solanum tuberosum, Glycine max, Beta vulgaris, Nicotiana tabacum,* and *Arabidopsis thaliana*.

Moreover the present invention can be applied to other crop plants with C3 photosynthesis, such as *Artocarpus heterophyllus, Psidium guajava, Ocimum tenuiflorum, Citrus limon, Mangifera indica, Allium cepa, Pisum sativum, Solanum tuberosum, Tectona grandis, Ipomoea batatas, Psidium guajava, Secale cereale, Canavalia ensiformis, Medicago sativa* L., *Prunus* amygdalus L., *Phaseolus vulgaris* L., *Malus* spp., *Prunus armeniaca* L., *Asparagus officinalis* L., *Persea* american P.mill., *Musa sapientum* L., *Brassica oleracea* L., *Daucus carota* L., *Anacardium occidentale* L., *Cicer arietinum* L., *Theobroma cacao* L., *Vigna unguiculata, Vaccinium macrocarpon, Cucumis sativus* L., *Solanum melongena* L., *Vicia faba* L., *Ficus carica* L., *Linum usitatissimum* L., *Vitis vinifera* L., *Lactuca* spp., *Phaseolus lunatus* L., *Beta vulgaris* L., *Olea* europea L., *Citrus sinensis* L., *Petroselium* crispum, *Prunus persica* L., *Arachis hypogea* L., *Pyrus communis* L., *Carya illinoinensis, Capsicum* spp., *Cajanus cajan, Prunus* spp., *Gossypium hirsutum* L., *Ocimum tenuiflorum, Ricinus communis* L., and *Taraxacum officinale* Wigg.

Thus, in one embodiment of the present invention, the method for the production of a transgenic plant with altered photorespiration and improved $CO_2$ fixation, comprises introducing into a cell or tissue of said plant one or more nucleic acids encoding at least four polypeptides having the enzymatic activities of
(a) erythro-β-hydroxyaspartate aldolase belonging to the EC class 4.1.3.14,
(b) erythro-β-hydroxyaspartate dehydratase belonging to the EC class 4.3.1.20,
(c) iminosuccinate reductase and
(d) aspartate-glyoxylate transaminase,
wherein the introduction of said nucleic acid(s) results in a de novo expression of the at least four polypeptides having the enzymatic activities of
(a) erythro-β-hydroxyaspartate aldolase belonging to the EC class 4.1.3.14,
(b) erythro-β-hydroxyaspartate dehydratase belonging to the EC class 4.3.1.20,
(c) iminosuccinate reductase and
(d) aspartate-glyoxylate transaminase,
wherein the polypeptide having the enzymatic activity of (c) iminosuccinate reductase comprises an amino acid sequence selected from SEQ ID NO: 1-299, or an amino acid sequence having at least 80% sequence identity to a sequence selected from SEQ ID NO: 1-299;
the polypeptide having the enzymatic activity of (d) aspartate-glyoxylate transaminase comprises an amino acid sequence selected from SEQ ID NO: 300-599, or an amino acid sequence having at least 80% sequence identity to a sequence selected from SEQ ID NO: 300-599,
and wherein the plant is selected from *Helianthus annuus, Brassica napus, Camelina sativa, Oryza sativa, Hordeum vulgare, Triticum* spp., *Avena sativa, Solanum lycopersicum, Solanum tuberosum, Glycine max, Beta vulgaris, Nicotiana tabacum, Arabidopsis thaliana, Artocarpus heterophyllus, Psidium guajava, Ocimum tenuiflorum, Citrus limon, Mangifera indica, Allium cepa, Pisum sativum, Solanum tuberosum, Tectona grandis, Ipomoea batatas, Psidium guajava, Secale cereale, Canavalia ensiformis, Medicago sativa* L., *Prunus* amygdalus L., *Phaseolus vulgaris* L., *Malus* spp., *Prunus armeniaca* L., *Asparagus officinalis* L., *Persea* american P.mill., *Musa sapientum* L., *Brassica oleracea* L., *Daucus carota* L., *Anacardium occidentale* L., *Cicer arietinum* L., *Theobroma cacao* L., *Vigna unguiculata, Vaccinium macrocarpon, Cucumis sativus* L., *Solanum melongena* L., *Vicia faba* L., *Ficus carica* L., *Linum usitatissimum* L., *Vitis vinifera* L., *Lactuca* spp., *Phaseolus lunatus* L., *Beta vulgaris* L., *Olea* europea L., *Citrus sinensis* L., *Petroselium crispum, Prunus persica* L., *Arachis hypogea* L., *Pyrus communis* L., *Carya illinoinensis, Capsicum* spp., *Cajanus cajan, Prunus* spp., *Gossypium hirsutum* L., *Ocimum tenuiflorum, Ricinus communis* L., and *Taraxacum officinale*.

Preferably, in the inventive methods described above, the de novo expressed (c) iminosuccinate reductase comprises an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to a sequence selected from SEQ ID NO: 1-299.

More preferably, the polypeptide having the enzymatic activity of (c) iminosuccinate reductase comprises an amino acid sequence selected from SEQ ID NO: 1, 7, 22, 25, 26, 39, 47, 58, 75, 123, 135, and 160, or an amino acid sequence having at least 80% sequence identity to a sequence selected from SEQ ID NO: 1, 7, 22, 25, 26, 39, 47, 58, 75, 123, 135, and 160.

Preferably, in the inventive methods described above, the de novo expressed (d) aspartate-glyoxylate transaminase comprises an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to a sequence selected from SEQ ID NO: 300-599.

More preferably, in the inventive methods described above, the polypeptide having the enzymatic activity of (c) iminosuccinate reductase comprises an amino acid sequence as set forth in SEQ ID NO: 135, or an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to said sequence; and the polypeptide having the enzymatic activity of (d) aspartate-glyoxylate transaminase comprises an amino acid sequence as set forth in SEQ ID NO: 433, or an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to said sequence.

Preferably, in the inventive methods described above, the (a) erythro-β-hydroxyaspartate aldolase belonging to the EC class 4.1.3.14 is C-terminally fused to a peroxisomal targeting signal 2 of SEQ ID NO: 952 and the polypeptides having the enzymatic activities (b)-(d) are N-terminally fused to a peroxisomal targeting signal 1 of amino acid sequence SKL.

The inventors could also show that the expression of the enzymes of the BHAP can be induced by increasing intracellular levels of glyoxylate, which acts as an effector of the β-hydroxyaspartate regulatory protein. Therefore, the expression of the β-hydroxyaspartate regulatory protein (BHAR) allows for the specific induction of the BHAP in transgenic plants by increasing intracellular levels of glyoxylate. Thus in one embodiment of the present invention, the method for the production of a transgenic plant with altered photorespiration and improved $CO_2$ fixation, comprises introducing into a cell or tissue of said plant one or more nucleic acids encoding at least five polypeptides having the enzymatic activities of
(a) erythro-β-hydroxyaspartate aldolase belonging to the EC class 4.1.3.14,
(b) erythro-β-hydroxyaspartate dehydratase belonging to the EC class 4.3.1.20,
(c) iminosuccinate reductase,
(d) aspartate-glyoxylate transaminase, and
(e) β-hydroxyaspartate regulatory protein,
wherein the introduction of the nucleic acid(s) results in a de novo expression of at least five polypeptides having the enzymatic activities of
(a) erythro-β-hydroxyaspartate aldolase belonging to the EC class 4.1.3.14,
(b) erythro-β-hydroxyaspartate dehydratase belonging to the EC class 4.3.1.20,
(c) iminosuccinate reductase,
(d) aspartate-glyoxylate transaminase, and
(e) β-hydroxyaspartate regulatory protein,
wherein the polypeptide having the enzymatic activity of (c) iminosuccinate reductase comprises an amino acid sequence selected from SEQ ID NO: 1-299, or an amino acid sequence having at least 80% sequence identity to a sequence selected from SEQ ID NO: 1-299;
wherein the polypeptide having the enzymatic activity of (d) aspartate-glyoxylate transaminase comprises an amino acid sequence selected from SEQ ID NO: 300-599, or an amino acid sequence having at least 80% sequence identity to a sequence selected from SEQ ID NO: 300-599; and
wherein the polypeptide having the enzymatic activity of (e) β-hydroxyaspartate regulatory protein comprises an amino acid sequence selected from SEQ ID NO: 600-899, or an amino acid sequence having at least 80% sequence identity to a sequence selected from SEQ ID NO: 600-899.

Preferably, the polypeptide having the enzymatic activity of (e) β-hydroxyaspartate regulatory protein comprises an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99%% sequence identity to a sequence selected from SEQ ID NO: 600-899.

More preferably, the polypeptide having the enzymatic activity of (e) β-hydroxyaspartate regulatory protein comprises an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%% and most preferably at least 100% sequence identity to SEQ ID NO: 732.

Another aspect of the present invention is directed to a transgenic plant comprising one or more nucleic acids encoding at least four polypeptides having the enzymatic activities of (a) erythro-β-hydroxyaspartate aldolase, (b) erythro-β-hydroxyaspartate dehydratase, (c) iminosuccinate reductase, and (d) aspartate-glyoxylate transaminase. More in details, the present invention is directed to a transgenic plant comprising one or more heterologous nucleic acids encoding at least four polypeptides having the enzymatic activities of (a) erythro-β-hydroxyaspartate aldolase belonging to the EC class 4.1.3.14, (b) erythro-β-hydroxyaspartate dehydratase belonging to the EC class 4.3.1.20, (c) iminosuccinate reductase comprising an amino acid sequence selected from SEQ ID NO: 1-299, or an amino acid sequence having at least 80% sequence identity to a sequence selected from SEQ ID NO: 1-299; and (d) aspartate-glyoxylate transaminase comprising an amino acid sequence selected from SEQ ID NO: 300-599, or an amino acid sequence having at least 80% sequence identity to a sequence selected from SEQ ID NO: 300-599.

More preferably, the inventive transgenic plant comprises one or more heterologous nucleic acids, which encode a polypeptide having the enzymatic activity of (a) erythro-β-hydroxyaspartate aldolase which comprises an amino acid sequence having at least 80% sequence identity to SEQ ID NO: 953, a polypeptide having the enzymatic activity of (b) erythro-β-hydroxyaspartate which comprises an amino acid sequence having at least 80% sequence identity SEQ ID NO: 954, a polypeptide having the enzymatic activity of (c) iminosuccinate reductase which comprises an amino acid sequence having at least 80% sequence identity to a sequence selected from SEQ ID NO: 1-299; and a polypeptide having the enzymatic activity of (d) aspartate-glyoxylate transaminase which comprises an amino acid sequence having at least 80% sequence identity to a sequence selected from SEQ ID NO: 300-599.

More preferably, the inventive transgenic plant comprises one or more heterologous nucleic acids, which encode a polypeptide having the enzymatic activity of (a) erythro-β-hydroxyaspartate aldolase which comprises an amino acid sequence having at least 90% sequence identity to SEQ ID NO: 953, a polypeptide having the enzymatic activity of (b) erythro-β-hydroxyaspartate which comprises an amino acid sequence having at least 90% sequence identity to SEQ ID NO: 954, a polypeptide having the enzymatic activity of (c) iminosuccinate reductase which comprises an amino acid sequence having at least 90% sequence identity to a sequence selected from SEQ ID NO: 1-299; and a polypeptide having the enzymatic activity of (d) aspartate-glyoxylate transaminase which comprises an amino acid sequence having at least 90% sequence identity to a sequence selected from SEQ ID NO: 300-599.

More preferably, the inventive transgenic plant comprises one or more heterologous nucleic acids, which encode a polypeptide having the enzymatic activity of (a) erythro-β-hydroxyaspartate aldolase which comprises an amino acid sequence having at least 95% sequence identity to SEQ ID NO: 953, a polypeptide having the enzymatic activity of (b) erythro-β-hydroxyaspartate which comprises an amino acid sequence having at least 95% sequence identity to SEQ ID NO: 954, a polypeptide having the enzymatic activity of (c) iminosuccinate reductase which comprises an amino acid sequence having at least 95% sequence identity to a sequence selected from SEQ ID NO: 1-299; and a polypeptide having the enzymatic activity of (d) aspartate-glyoxylate transaminase which comprises an amino acid sequence having at least 95% sequence identity to a sequence selected from SEQ ID NO: 300-599.

More preferably, the inventive transgenic plant comprises one or more heterologous nucleic acids, which encode a polypeptide having the enzymatic activity of (a) erythro-β-hydroxyaspartate aldolase which comprises an amino acid sequence having at least 97% sequence identity to SEQ ID NO: 953, a polypeptide having the enzymatic activity of (b) erythro-β-hydroxyaspartate which comprises an amino acid sequence having at least 97% sequence identity to SEQ ID NO: 954, a polypeptide having the enzymatic activity of (c) iminosuccinate reductase which comprises an amino acid sequence having at least 97% sequence identity to a sequence selected from SEQ ID NO: 1-299; and a polypeptide having the enzymatic activity of (d) aspartate-glyoxylate transaminase which comprises an amino acid sequence having at least 97% sequence identity to a sequence selected from SEQ ID NO: 300-599.

More preferably, the inventive transgenic plant comprises one or more heterologous nucleic acids, which encode a polypeptide having the enzymatic activity of (a) erythro-β-hydroxyaspartate aldolase which comprises an amino acid sequence having at least 99% sequence identity to SEQ ID NO: 953, a polypeptide having the enzymatic activity of (b) erythro-β-hydroxyaspartate which comprises an amino acid sequence having at least 99% sequence identity to SEQ ID NO: 954, a polypeptide having the enzymatic activity of (c) iminosuccinate reductase which comprises an amino acid sequence having at least 99% sequence identity to a sequence selected from SEQ ID NO: 1-299; and a polypeptide having the enzymatic activity of (d) aspartate-glyoxylate transaminase which comprises an amino acid sequence having at least 99% sequence identity to a sequence selected from SEQ ID NO: 300-599.

Still more preferably, the inventive transgenic plant comprises one or more heterologous nucleic acids, which encode a polypeptide having the enzymatic activity of (a) erythro-β-hydroxyaspartate aldolase which comprises an amino acid sequence of SEQ ID NO: 953, a polypeptide having the enzymatic activity of (b) erythro-β-hydroxyaspartate which comprises an amino acid sequence of SEQ ID NO: 954, a polypeptide having the enzymatic activity of (c) iminosuccinate reductase which comprises an amino acid sequence selected from SEQ ID NO: 1-299; and a polypeptide having the enzymatic activity of (d) aspartate-glyoxylate transaminase which comprises an amino acid sequence selected from SEQ ID NO: 300-599.

Within the context of the present invention, synthetic nucleic acids refer to nucleic acids which are of different natural or of synthetic origin, such as derived from another microorganism and then codon optimized for high expression in C3 plant.

Preferably, the transgenic plant of the present invention comprises one or more heterologous nucleic acids encoding at least four polypeptides having the enzymatic activities of (a) erythro-β-hydroxyaspartate aldolase belonging to the EC class 4.1.3.14, (b) erythro-β-hydroxyaspartate dehydratase belonging to the EC class 4.3.1.20, (c) iminosuccinate reductase comprising an amino acid sequence selected from SEQ ID NO: 1-299, or an amino acid sequence having at least 80% sequence identity to a sequence selected from SEQ ID NO: 1-299; and (d) aspartate-glyoxylate transaminase comprising an amino acid sequence selected from SEQ ID NO: 300-599, or an amino acid sequence having at least 80% sequence identity to a sequence selected from SEQ ID NO: 300-599, wherein said polypeptides having the enzymatic activities (a)-(d) are localized in peroxisomes.

More preferably, the transgenic plant of the present invention comprises one or more heterologous nucleic acids encoding at least four polypeptides having the enzymatic activities of (a) erythro-β-hydroxyaspartate aldolase belonging to the EC class 4.1.3.14, (b) erythro-β-hydroxyaspartate dehydratase belonging to the EC class 4.3.1.20, (c) iminosuccinate reductase comprising an amino acid sequence selected from SEQ ID NO: 1-299, or an amino acid sequence having at least 80% sequence identity to a sequence selected from SEQ ID NO: 1-299; and (d) aspartate-glyoxylate transaminase comprising an amino acid sequence selected from SEQ ID NO: 300-599, or an amino acid sequence having at least 80% sequence identity to a sequence selected from SEQ ID NO: 300-599,
wherein the polypeptides having the enzymatic activities (a)-(d) comprise an amino acid sequence targeting said polypeptides to the peroxisomes, and
wherein the (a) erythro-β-hydroxyaspartate aldolase belonging to the EC class 4.1.3.14 is C-terminally fused to a peroxisomal targeting signal 2 of SEQ ID NO: 952 and the polypeptides having the enzymatic activities (b)-(d) are N-terminally fused to a peroxisomal targeting signal 1 of amino acid sequence SKL.

In alternative, the transgenic plant of the present invention comprises one or more heterologous nucleic acids encoding at least five polypeptides having the enzymatic activities of (a) erythro-β-hydroxyaspartate aldolase belonging to the EC class 4.1.3.14, (b) erythro-β-hydroxyaspartate dehydratase belonging to the EC class 4.3.1.20, (c) iminosuccinate reductase comprising an amino acid sequence selected from SEQ ID NO: 1-299, or an amino acid sequence having at least 80% sequence identity to a sequence selected from SEQ ID NO: 1-299; (d) aspartate-glyoxylate transaminase comprising an amino acid sequence selected from SEQ ID NO: 300-599, or an amino acid sequence having at least 80% sequence identity to a sequence selected from SEQ ID NO: 300-599, and (e) glycolate dehydrogenase belonging to the EC class 1.1.99.14, wherein said polypeptides having the enzymatic activities (a)-(e) are localized in mitochondria.

More preferably, the transgenic plant of the present invention comprises one or more heterologous nucleic acids encoding at least five polypeptides having the enzymatic activities of (a) erythro-β-hydroxyaspartate aldolase belonging to the EC class 4.1.3.14, (b) erythro-β-hydroxyaspartate dehydratase belonging to the EC class 4.3.1.20, (c) iminosuccinate reductase comprising an amino acid sequence selected from SEQ ID NO: 1-299, or an amino acid sequence having at least 80% sequence identity to a sequence selected from SEQ ID NO: 1-299; (d) aspartate-glyoxylate transaminase comprising an amino acid sequence selected from SEQ ID NO: 300-599, or an amino acid sequence having at least 80% sequence identity to a sequence selected from SEQ ID NO: 300-599, and (e) glycolate dehydrogenase belonging to the EC class 1.1.99.14, wherein said polypeptides having the enzymatic activities (a)-(e) are localized in mitochondria, and wherein said polypeptides having the enzymatic activities (a)-(e) are N-terminally fused to a serine hydroxymethyltransferase 1 target peptide of SEQ ID NO: 919.

In another aspect, the transgenic plant of the present invention comprises one or more heterologous nucleic acids encoding at least six polypeptides having the enzymatic activities of (a) erythro-β-hydroxyaspartate aldolase belonging to the EC class 4.1.3.14, (b) erythro-β-hydroxyaspartate dehydratase belonging to the EC class 4.3.1.20, (c) iminosuccinate reductase comprising an amino acid sequence selected from SEQ ID NO: 1-299, or an amino acid sequence having at least 80% sequence identity to a sequence selected from SEQ ID NO: 1-299; (d) aspartate-glyoxylate transaminase comprising an amino acid sequence selected from SEQ ID NO: 300-599, or an amino acid sequence having at least 80% sequence identity to a sequence selected from SEQ ID NO: 300-599, (e) glycolate dehydrogenase belonging to the EC class 1.1.99.14, and (f) phosphoenolpyruvate carboxykinase belonging to the EC class 4.1.3.14, wherein said polypeptides having the enzymatic activities (a)-(f) are localized in chloroplasts.

More preferably, the transgenic plant of the present invention comprises one or more heterologous nucleic acids encoding at least six polypeptides having the enzymatic activities of (a) erythro-β-hydroxyaspartate aldolase belonging to the EC class 4.1.3.14, (b) erythro-β-hydroxyaspartate dehydratase belonging to the EC class 4.3.1.20, (c) iminosuccinate reductase comprising an amino acid sequence selected from SEQ ID NO: 1-299, or an amino acid sequence having at least 80% sequence identity to a sequence selected from SEQ ID NO: 1-299; (d) aspartate-glyoxylate transaminase comprising an amino acid sequence selected from SEQ ID NO: 300-599, or an amino acid sequence having at least 80% sequence identity to a sequence selected from SEQ ID NO: 300-599, (e) glycolate dehydrogenase belonging to the EC class 1.1.99.14, and (f) phosphoenolpyruvate carboxykinase belonging to the EC class 4.1.3.14, wherein said polypeptides having the enzymatic activities (a)-(f) are localized in chloroplasts, and wherein said polypeptides having the enzymatic activities (a)-(f) are N-terminally fused to *Arabidopsis* Ferredoxin-2 chloroplastic target peptide of SEQ ID NO: 917.

Preferably, in inventive transgenic plants described herein, the de novo expressed (c) iminosuccinate reductase comprises an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to a sequence selected from SEQ ID NO: 1-299.

More preferably, the polypeptide having the enzymatic activity of (c) iminosuccinate reductase comprises an amino acid sequence selected from SEQ ID NO: 1, 7, 22, 25, 26, 39, 47, 58, 75, 123, 135, and 160, or an amino acid sequence having at least 80% sequence identity to a sequence selected from SEQ ID NO: 1, 7, 22, 25, 26, 39, 47, 58, 75, 123, 135, and 160.

Preferably, in inventive transgenic plants described herein, the de novo expressed (d) aspartate-glyoxylate transaminase comprises an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to a sequence selected from SEQ ID NO: 300-599.

More preferably, in inventive transgenic plants described herein, the polypeptide having the enzymatic activity of (c) iminosuccinate reductase comprises an amino acid sequence as set forth in SEQ ID NO: 135, or an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to said sequence; and the polypeptide having the enzymatic activity of (d) aspartate-glyoxylate transaminase comprises an amino acid sequence as set forth in SEQ ID NO: 433, or an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to said sequence.

The transgenic plant can be any C3 plant, including but not limited to *Helianthus annuus, Brassica napus, Camelina sativa, Oryza sativa, Hordeum vulgare, Triticum* spp., *Avena sativa, Solanum lycopersicum, Solanum tuberosum, Glycine max, Beta vulgaris, Nicotiana tabacum*, and *Arabidopsis thaliana*.

Therefore, one embodiment of the present invention is directed to a transgenic plant comprising one or more heterologous nucleic acids encoding at least four polypeptides having the enzymatic activities of (a) erythro-β-hydroxyaspartate aldolase belonging to the EC class 4.1.3.14, (b) erythro-β-hydroxyaspartate dehydratase belonging to the EC class 4.3.1.20, (c) iminosuccinate reductase comprising an amino acid sequence selected from SEQ ID NO: 1-299, or an amino acid sequence having at least 80% sequence identity to a sequence selected from SEQ ID NO: 1-299; and (d) aspartate-glyoxylate transaminase comprising an amino acid sequence selected from SEQ ID NO: 300-599, or an amino acid sequence having at least 80% sequence identity to a sequence selected from SEQ ID NO: 300-599, wherein the plant is a C3 plant.

One embodiment of the present invention is directed to a transgenic plant comprising one or more heterologous nucleic acids encoding at least four polypeptides having the enzymatic activities of (a) erythro-β-hydroxyaspartate aldolase belonging to the EC class 4.1.3.14, (b) erythro-β-hydroxyaspartate dehydratase belonging to the EC class 4.3.1.20, (c) iminosuccinate reductase comprising an amino acid sequence selected from SEQ ID NO: 1-299, or an amino acid sequence having at least 80% sequence identity to a sequence selected from SEQ ID NO: 1-299; and (d) aspartate-glyoxylate transaminase comprising an amino acid sequence selected from SEQ ID NO: 300-599, or an amino acid sequence having at least 80% sequence identity to a sequence selected from SEQ ID NO: 300-599, wherein the plant is selected from *Helianthus annuus, Brassica napus, Camelina sativa, Oryza sativa, Hordeum vulgare, Triticum* spp., *Avena sativa, Solanum lycopersicum, Solanum tuberosum, Glycine max, Beta vulgaris, Nicotiana tabacum*, and *Arabidopsis thaliana*.

Moreover, one embodiment of the present invention is directed to a transgenic plant comprising one or more heterologous nucleic acids encoding at least four polypeptides having the enzymatic activities of (a) erythro-β-hydroxyaspartate aldolase belonging to the EC class 4.1.3.14, (b) erythro-β-hydroxyaspartate dehydratase belonging to the EC class 4.3.1.20, (c) iminosuccinate reductase comprising an amino acid sequence selected from SEQ ID NO: 1-299, or an amino acid sequence having at least 80% sequence identity to a sequence selected from SEQ ID NO: 1-299; and (d) aspartate-glyoxylate transaminase comprising an amino acid sequence selected from SEQ ID NO: 300-599, or an amino acid sequence having at least 80% sequence identity to a sequence selected from SEQ ID NO: 300-599, wherein said polypeptides having the enzymatic activities (a)-(d) are localized in peroxisomes, and wherein the plant is a C3 plant.

One embodiment of the present invention is directed to a transgenic plant comprising one or more heterologous nucleic acids encoding four polypeptides having the enzymatic activities of (a) erythro-β-hydroxyaspartate aldolase belonging to the EC class 4.1.3.14, (b) erythro-β-hydroxyaspartate dehydratase belonging to the EC class 4.3.1.20, (c) iminosuccinate reductase comprising an amino acid sequence selected from SEQ ID NO: 1-299, or an amino acid sequence having at least 80% sequence identity to a sequence selected from SEQ ID NO: 1-299; and (d) aspartate-glyoxylate transaminase comprising an amino acid sequence selected from SEQ ID NO: 300-599, or an amino acid sequence having at least 80% sequence identity to a sequence selected from SEQ ID NO: 300-599, wherein said polypeptides having the enzymatic activities (a)-(d) are localized in peroxisomes, and wherein the plant is selected from *Helianthus annuus, Brassica napus, Camelina sativa, Oryza sativa, Hordeum vulgare, Triticum* spp., *Avena sativa, Solanum lycopersicum, Solanum tuberosum, Glycine max, Beta vulgaris, Nicotiana tabacum*, and *Arabidopsis thaliana*.

In an alternative embodiment, the transgenic plant of the present invention comprises one or more heterologous nucleic acids encoding at least five polypeptides having the enzymatic activities of (a) erythro-β-hydroxyaspartate aldolase belonging to the EC class 4.1.3.14, (b) erythro-β-hydroxyaspartate dehydratase belonging to the EC class 4.3.1.20, (c) iminosuccinate reductase comprising an amino acid sequence selected from SEQ ID NO: 1-299, or an amino acid sequence having at least 80% sequence identity to a sequence selected from SEQ ID NO: 1-299; (d) aspartate-glyoxylate transaminase comprising an amino acid sequence selected from SEQ ID NO: 300-599, or an amino acid sequence having at least 80% sequence identity to a sequence selected from SEQ ID NO: 300-599, and (e) glycolate dehydrogenase belonging to the EC class 1.1.99.14, wherein said polypeptides having the enzymatic activities (a)-(e) are localized in mitochondria, and wherein the plant is a C3 plant.

Also, the transgenic plant of the present invention comprises one or more heterologous nucleic acids encoding at least five polypeptides having the enzymatic activities of (a) erythro-β-hydroxyaspartate aldolase belonging to the EC class 4.1.3.14, (b) erythro-β-hydroxyaspartate dehydratase belonging to the EC class 4.3.1.20, (c) iminosuccinate reductase comprising an amino acid sequence selected from SEQ ID NO: 1-299, or an amino acid sequence having at least 80% sequence identity to a sequence selected from SEQ ID NO: 1-299; (d) aspartate-glyoxylate transaminase comprising an amino acid sequence selected from SEQ ID NO: 300-599, or an amino acid sequence having at least 80% sequence identity to a sequence selected from SEQ ID NO: 300-599, and (e) glycolate dehydrogenase belonging to the EC class 1.1.99.14, wherein said polypeptides having the enzymatic activities (a)-(e) are localized in mitochondria, and wherein the plant is selected from *Helianthus annuus, Brassica napus, Camelina sativa, Oryza sativa, Hordeum vulgare, Triticum* spp., *Avena sativa, Solanum lycopersicum, Solanum tuberosum, Glycine max, Beta vulgaris, Nicotiana tabacum*, and *Arabidopsis thaliana*.

In another aspect, the transgenic plant of the present invention comprises one or more heterologous nucleic acids encoding at least six polypeptides having the enzymatic activities of (a) erythro-β-hydroxyaspartate aldolase belonging to the EC class 4.1.3.14, (b) erythro-β-hydroxyaspartate dehydratase belonging to the EC class 4.3.1.20, (c) iminosuccinate reductase comprising an amino acid sequence selected from SEQ ID NO: 1-299, or an amino acid sequence having at least 80% sequence identity to a sequence selected from SEQ ID NO: 1-299; (d) aspartate-glyoxylate transaminase comprising an amino acid sequence selected from SEQ ID NO: 300-599, or an amino acid sequence having at least 80% sequence identity to a sequence selected from SEQ ID NO: 300-599, (e) glycolate dehydrogenase belonging to the EC class 1.1.99.14, and (f) phosphoenolpyruvate carboxykinase belonging to the EC class 4.1.3.14, wherein said polypeptides having the enzymatic activities (a)-(f) are localized in chloroplasts, and wherein the plant is a C3 plant.

In another aspect, the transgenic plant of the present invention comprises one or more heterologous nucleic acids encoding at least six polypeptides having the enzymatic activities of (a) erythro-β-hydroxyaspartate aldolase belonging to the EC class 4.1.3.14, (b) erythro-β-hydroxyaspartate dehydratase belonging to the EC class 4.3.1.20, (c) iminosuccinate reductase comprising an amino acid sequence selected from SEQ ID NO: 1-299, or an amino acid sequence having at least 80% sequence identity to a sequence selected from SEQ ID NO: 1-299; (d) aspartate-glyoxylate transaminase comprising an amino acid sequence selected from SEQ ID NO: 300-599, or an amino acid sequence having at least 80% sequence identity to a sequence selected from SEQ ID NO: 300-599, (e) glycolate dehydrogenase belonging to the EC class 1.1.99.14, and (f) phosphoenolpyruvate carboxykinase belonging to the EC class 4.1.3.14, wherein said polypeptides having the enzymatic activities (a)-(f) are localized in chloroplasts, and wherein the plant is selected from *Helianthus annuus, Brassica napus, Camelina sativa, Oryza sativa, Hordeum vulgare, Triticum* spp., *Avena sativa, Solanum lycopersicum, Solanum tuberosum, Glycine max, Beta vulgaris, Nicotiana tabacum*, and *Arabidopsis thaliana*.

Moreover the present invention can be applied to other crop plants with C3 photosynthesis, such as *Artocarpus heterophyllus, Psidium guajava, Ocimum tenuiflorum, Citrus limon, Mangifera indica, Allium cepa, Pisum sativum, Solanum tuberosum, Tectona grandis, Ipomoea batatas, Psidium guajava, Secale cereale, Canavalia ensiformis, Medicago sativa* L., *Prunus amygdalus* L., *Phaseolus vulgaris* L., *Malus* spp., *Prunus armeniaca* L., *Asparagus officinalis* L., *Persea american* P.mill., *Musa sapientum* L., *Brassica oleracea* L., *Daucus carota* L., *Anacardium occidentale* L., *Cicer arietinum* L., *Theobroma cacao* L., *Vigna unguiculata, Vaccinium macrocarpon, Cucumis sativus* L., *Solanum melongena* L., *Vicia faba* L., *Ficus carica* L., *Linum usitatissimum* L., *Vitis vinifera* L., *Lactuca* spp., *Phaseolus lunatus* L., *Beta vulgaris* L., *Olea europea* L., *Citrus sinensis* L., *Petroselium crispum, Prunus persica* L., *Arachis hypogea* L., *Pyrus communis* L., *Carya illinoinensis, Capsicum* spp., *Cajanus cajan, Prunus* spp., *Gossypium hirsutum* L., *Ocimum* tenuiflorum, *Ricinus communis* L., and *Taraxacum officinale* Wigg.

Preferably, in inventive transgenic C3 plants described herein, the de novo expressed (c) iminosuccinate reductase comprises an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to a sequence selected from SEQ ID NO: 1-299.

More preferably, the polypeptide having the enzymatic activity of (c) iminosuccinate reductase comprises an amino acid sequence selected from SEQ ID NO: 1, 7, 22, 25, 26, 39, 47, 58, 75, 123, 135, and 160, or an amino acid sequence having at least 80% sequence identity to a sequence selected from SEQ ID NO: 1, 7, 22, 25, 26, 39, 47, 58, 75, 123, 135, and 160.

Preferably, in inventive transgenic C3 plants described herein, the de novo expressed (d) aspartate-glyoxylate transaminase comprises an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to a sequence selected from SEQ ID NO: 300-599.

More preferably, in inventive transgenic C3 plants described herein, the polypeptide having the enzymatic activity of (c) iminosuccinate reductase comprises an amino acid sequence as set forth in SEQ ID NO: 135, or an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to said sequence; and the polypeptide having the enzymatic activity of (d) aspartate-glyoxylate transaminase comprises an amino acid sequence as set forth in SEQ ID NO: 433, or an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to said sequence.

Moreover, the inventors have designed a nucleic acid construct for implementation of the four polypeptides of BHAP in plants (FIG. 9). Within the multigene construct each BHAP enzyme is expressed under its own photosynthetically regulated promoter, restricting BHAP expression to photosynthetic tissue and coupling BHAP expression to light and high photorespiratory metabolic flux. In particular, the nucleic acid construct comprises the nucleic acid sequence coding the polypeptide having the enzymatic activity BHAA under the *Arabidopsis* RubisCO small subunit 2B promoter (AtRbcS2Bp, AT5g38420), the nucleic acid sequence coding the polypeptide having the enzymatic activity BHAD is expressed under the *Arabidopsis* RubisCO small subunit 1B promoter (AtRbcS1 Bp, AT5g38430), the nucleic acid sequence coding the polypeptide having the enzymatic activity ISRed expressed under the *Arabidopsis* RubisCO small subunit 3B promoter (AtRbS3Bp, AT5g38410), and the nucleic acid sequence coding the polypeptide having the enzymatic activity AsGAT expressed under *Arabidopsis* chlorophyll A binding protein promoter (AtCaBp, AT1g29930). Moreover, the nucleic acid construct comprises terminator sequences operably linked to the nucleic acid sequence coding each polypeptide. These terminators are: *Agrobacterium tumefaciens* octopine synthase terminator (AtuOCSt), *Agrobacterium tumefaciens* nopaline synthase terminator (AtuNOSt), 35S terminator derived from the Cauliflower Mosaic Virus (35St), *Solanum lycopersicum* RubisCO small subunit 3C terminator (SlRbcS3Ct). Kanamycin resistance is used as selection marker.

Functionality of this nucleic acid construct regarding expression of all four enzymes was verified by transient expression in *N. benthamiana*, followed by immunoblot analysis (FIG. 10-11).

Moreover *Arabidopsis* wildtype Col-0 and ggt1 mutant (GK-649H07) were transformed with the generated BHAP nucleic acid construct by floral dipping. The ggt1 mutant is deficient in the peroxisomal glyoxylate:glutamate aminotransferase 1 (GGT1, At1g23310) and accumulates glyoxylate (see Dellero et. al, Plant J. 83, 1005-1018 (2015)). The inventors verified complete BHAP implementation in *Arabidopsis* WT and ggt1 mutant by genotyping using for each BHAP enzyme a combination forward and reverse primers specific for the promoter and the coding sequence of interest (FIG. 16). The established transgenic lines with the BHAP in WT and ggt1 mutant background are analyzed for protein expression and enzymatic activity of all four BHAP enzymes to identify primary transformants with high BHAP activity. Therefore, BHAP enzymes are individually assayed in vitro and complete BHAP activity is tested.

Thus, another aspect of the present invention is directed to a nucleic acid construct comprising nucleic acid sequences encoding at least four polypeptides having the enzymatic activities of (a) erythro-β-hydroxyaspartate aldolase belonging to the EC class 4.1.3.14, (b) erythro-β-hydroxyaspartate dehydratase belonging to the EC class 4.3.1.20, (c) iminosuccinate reductase comprising an amino acid sequence selected from SEQ ID NO: 1-299, or an amino acid sequence having at least 80% sequence identity to a sequence selected from SEQ ID NO: 1-299; (d) aspartate-glyoxylate transaminase comprising an amino acid sequence selected from SEQ ID NO: 300-599, or an amino acid sequence having at least 80% sequence identity to a sequence selected from SEQ ID NO: 300-599, wherein said nucleic acid sequences are operably linked to at least one promoter for expression in a plant. Preferably, the nucleic acid sequences are further operably linked to at least one terminator.

"Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame. A nucleic acid is "operably linked" when it is placed into a functional relationship with another nucleic acid sequence. In particular, by "operably linked" is meant that a gene and a regulatory sequence(s) are connected in such a way as to permit gene expression when the appropriate molecules (e.g., transcriptional activator proteins) are bound to the regulatory sequence(s). For example, DNA for a presequence or secretory leader is operably linked to DNA for a polypeptide if it is expressed as a preprotein that participates in the secretion of the polypeptide; a promoter or enhancer or terminator is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and present in open reading frame. However, enhancers do not have to be contiguous. Linking is accomplished by ligation at convenient restriction sites. If such sites do not exist, the synthetic oligonucleotide adaptors or linkers are used in accordance with conventional practice.

Preferably, the promoter is a photosynthetically regulated promoter, such as *Arabidopsis* chlorophyll A binding protein promoter (AT1g29930), *Arabidopsis* RubisCO small subunit 2B promoter (AT5g38420), *Arabidopsis* RubisCO small subunit 1B promoter (AT5g38430), or *Arabidopsis* RubisCO small subunit 3B promoter (AT5g38410), thereby restricting expression of the BHAP enzymes to photosynthetic tissue and coupling the expression of said enzymes to light and high photorespiratory metabolic flux.

Therefore, one embodiment of the present invention is directed to a nucleic acid construct comprising nucleic acid sequences encoding four polypeptides having the enzymatic activities of (a) erythro-β-hydroxyaspartate aldolase belonging to the EC class 4.1.3.14, (b) erythro-β-hydroxyaspartate dehydratase belonging to the EC class 4.3.1.20, (c) iminosuccinate reductase comprising an amino acid sequence selected from SEQ ID NO: 1-299, or an amino acid sequence having at least 80% sequence identity to a sequence selected from SEQ ID NO: 1-299; (d) aspartate-glyoxylate transaminase comprising an amino acid sequence selected from SEQ ID NO: 300-599, or an amino acid sequence having at least 80% sequence identity to a sequence selected from SEQ ID NO: 300-599, wherein said nucleic acid sequences are operably linked to at least one photosynthetically regulated promoter for expression in a plant. Preferably, the photosynthetically regulated promoter is selected from *Arabidopsis* chlorophyll A binding protein promoter (AT1g29930), *Arabidopsis* RubisCO small subunit 2B promoter (AT5g38420), *Arabidopsis* RubisCO small subunit 1B promoter (AT5g38430), and *Arabidopsis* RubisCO small subunit 3B promoter (AT5g38410).

In one embodiment of the present invention the nucleic acid construct comprises nucleic acid sequences encoding at least four polypeptides having the enzymatic activities of (a) erythro-β-hydroxyaspartate aldolase belonging to the EC class 4.1.3.14, (b) erythro-β-hydroxyaspartate dehydratase belonging to the EC class 4.3.1.20, (c) iminosuccinate reductase comprising an amino acid sequence selected from SEQ ID NO: 1-299, or an amino acid sequence having at least 80% sequence identity to a sequence selected from SEQ ID NO: 1-299; (d) aspartate-glyoxylate transaminase comprising an amino acid sequence selected from SEQ ID NO: 300-599, or an amino acid sequence having at least 80% sequence identity to a sequence selected from SEQ ID NO: 300-599, wherein said nucleic acid sequences are operably linked to at least one photosynthetically regulated promoter for expression in a plant and are operably linked to at least one terminator.

In a further embodiment of the present invention the nucleic acid construct comprises nucleic acid sequences encoding at least four polypeptides having the enzymatic activities of (a) erythro-β-hydroxyaspartate aldolase belonging to the EC class 4.1.3.14, (b) erythro-β-hydroxyaspartate dehydratase belonging to the EC class 4.3.1.20, (c) iminosuccinate reductase comprising an amino acid sequence selected from SEQ ID NO: 1-299, or an amino acid sequence having at least 80% sequence identity to a sequence selected from SEQ ID NO: 1-299; (d) aspartate-glyoxylate transaminase comprising an amino acid sequence selected from SEQ ID NO: 300-599, or an amino acid sequence having at least 80% sequence identity to a sequence selected from SEQ ID NO: 300-599, a selection marker nucleic acid, wherein said nucleic acid sequences are operably linked to at least one photosynthetically regulated promoter for expression in a plant and are operably linked to at least one terminator. Preferably, the selection marker nucleic acid is a kanamycin resistance nucleic acid. Preferably, the kanamycin resistance nucleic acid comprises a nucleic acid sequence as included in SEQ ID NO: 986 (nucleotides 9581-11438).

Preferably, in the inventive nucleic acid constructs described herein, the nucleic acid sequences encode an (c) iminosuccinate reductase comprising an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to a sequence selected from SEQ ID NO: 1-299.

More preferably, the nucleic acid sequences encode an (c) iminosuccinate reductase comprising an amino acid sequence selected from SEQ ID NO: 1, 7, 22, 25, 26, 39, 47, 58, 75, 123, 135, and 160, or an amino acid sequence having at least 80% sequence identity to a sequence selected from SEQ ID NO: 1, 7, 22, 25, 26, 39, 47, 58, 75, 123, 135, and 160.

Preferably, in the inventive nucleic acid constructs described herein, the nucleic acid sequences encode an (d) aspartate-glyoxylate transaminase comprising an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to a sequence selected from SEQ ID NO: 300-599.

More preferably, in the inventive nucleic acid constructs described herein, the nucleic acid sequences encode an (c) iminosuccinate reductase comprising an amino acid sequence as set forth in SEQ ID NO: 135, or an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to said sequence; and the the nucleic acid sequences encode an (d) aspartate-glyoxylate transaminase comprising an amino acid sequence as set forth in SEQ ID NO: 433, or an amino acid sequence having at least 80%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to said sequence.

In one embodiment of the present invention, the nucleic acid construct comprises (1) a nucleic acid sequence comprising a sequence as set forth in SEQ ID NO: 963 which encodes a polypeptide having the enzymatic activity of erythro-β-hydroxyaspartate aldolase belonging to the EC class 4.1.3.14, (2) a nucleic acid sequence comprising a sequence as set forth in SEQ ID NO: 964, which encodes a polypeptide having the enzymatic activity of erythro-β-hydroxyaspartate dehydratase belonging to the EC class 4.3.1.20, (3) a nucleic acid sequence comprising a sequence as set forth in SEQ ID NO: 965, which encodes a polypeptide having the enzymatic activity of iminosuccinate reductase, and (4) a nucleic acid sequence comprising a sequence as set forth in SEQ ID NO: 966, which encodes a polypeptide having the enzymatic activity of aspartate-glyoxylate transaminase, wherein the nucleic acid sequences (1)-(4) are operably linked to at least one photosynthetically regulated promoter for expression in a plant.

Preferably, the nucleic acid construct comprises (1) a nucleic acid sequence comprising a sequence as set forth in SEQ ID NO: 963, which encodes a polypeptide having the enzymatic activity of erythro-β-hydroxyaspartate aldolase belonging to the EC class 4.1.3.14, (2) a nucleic acid sequence comprising a sequence as set forth in SEQ ID NO: 964, which encodes a polypeptide having the enzymatic activity of erythro-β-hydroxyaspartate dehydratase belonging to the EC class 4.3.1.20, (3) a nucleic acid sequence comprising a sequence as set forth in SEQ ID NO: 965, which encodes a polypeptide having the enzymatic activity of iminosuccinate reductase, and (4) a nucleic acid sequence comprising a sequence as set forth in SEQ ID NO: 966, which encodes a polypeptide having the enzymatic activity of aspartate-glyoxylate transaminase, wherein the nucleic acid sequences (1)-(4) are operably linked to at least one photosynthetically regulated promoter for expression in a plant and are operably linked to at least one terminator.

Preferably, the nucleic acid construct comprises (1) a nucleic acid sequence comprising a sequence as set forth in SEQ ID NO: 963, which encodes a polypeptide having the enzymatic activity of erythro-β-hydroxyaspartate aldolase belonging to the EC class 4.1.3.14, (2) a nucleic acid sequence comprising a sequence as set forth in SEQ ID NO: 964, which encodes a polypeptide having the enzymatic activity of erythro-β-hydroxyaspartate dehydratase belonging to the EC class 4.3.1.20, (3) a nucleic acid sequence comprising a sequence as set forth in SEQ ID NO: 965, which encodes a polypeptide having the enzymatic activity of iminosuccinate reductase, and (4) a nucleic acid sequence comprising a sequence as set forth in SEQ ID NO: 966, which encodes a polypeptide having the enzymatic activity of aspartate-glyoxylate transaminase, (5) a selection marker nucleic acid, wherein the nucleic acid sequences (1)-(5) are operably linked to at least one photosynthetically regulated promoter for expression in a plant and are operably linked to at least one terminator. Preferably, the selection marker nucleic acid is a kanamycin resistance nucleic acid.

Preferably, the kanamycin resistance nucleic acid comprises a nucleic acid sequence as included in SEQ ID NO: 986 (nucleotides 9581-11438).

More preferably, the nucleic acid construct comprises (1) a nucleic acid sequence comprising a sequence as set forth in SEQ ID NO: 963, which encodes a polypeptide having the enzymatic activity of erythro-β-hydroxyaspartate aldolase belonging to the EC class 4.1.3.14, (2) a nucleic acid sequence comprising a sequence as set forth in SEQ ID NO: 964, which encodes a polypeptide having the enzymatic activity of erythro-β-hydroxyaspartate dehydratase belonging to the EC class 4.3.1.20, (3) a nucleic acid sequence comprising a sequence as set forth in SEQ ID NO: 965, which encodes a polypeptide having the enzymatic activity of iminosuccinate reductase, and (4) a nucleic acid sequence comprising a sequence as set forth in SEQ ID NO: 966, which encodes a polypeptide having the enzymatic activity of aspartate-glyoxylate transaminase, (5) a kanamycin resistance nucleic acid, wherein the nucleic acid sequences (1)-(5) are operably linked to at least one photosynthetically regulated promoter for expression in a plant and are operably linked to at least one terminator. Preferably, the kanamycin resistance nucleic acid comprises a nucleic acid sequence as included in SEQ ID NO: 986 (nucleotides 9581-11438).

In one embodiment of the present invention, the nucleic acid construct comprises nucleic acid sequences encoding four polypeptides having the enzymatic activities of (a) erythro-β-hydroxyaspartate aldolase belonging to the EC class 4.1.3.14, (b) erythro-β-hydroxyaspartate dehydratase belonging to the EC class 4.3.1.20, (c) iminosuccinate reductase comprising an amino acid sequence selected from SEQ ID NO: 1-299, or an amino acid sequence having at least 80% sequence identity to a sequence selected from SEQ ID NO: 1-299; (d) aspartate-glyoxylate transaminase comprising an amino acid sequence selected from SEQ ID NO: 300-599, or an amino acid sequence having at least 80% sequence identity to a sequence selected from SEQ ID NO: 300-599, a further nucleic acid sequence targeting said polypeptides to the peroxisomes, and wherein said nucleic acid sequences are operably linked to at least one photosynthetically regulated promoter for expression in a plant.

Preferably, the nucleic acid construct comprises nucleic acid sequences encoding four polypeptides having the enzymatic activities of (a) erythro-β-hydroxyaspartate aldolase belonging to the EC class 4.1.3.14, (b) erythro-β-hydroxyaspartate dehydratase belonging to the EC class 4.3.1.20, (c) iminosuccinate reductase comprising an amino acid sequence selected from SEQ ID NO: 1-299, or an amino acid sequence having at least 80% sequence identity to a sequence selected from SEQ ID NO: 1-299; (d) aspartate-glyoxylate transaminase comprising an amino acid sequence selected from SEQ ID NO: 300-599, or an amino acid sequence having at least 80% sequence identity to a sequence selected from SEQ ID NO: 300-599, a further nucleic acid sequence targeting said polypeptides to the peroxisomes, and wherein said nucleic acid sequences are operably linked to at least one photosynthetically regulated promoter for expression in a plant and are operably linked to at least one terminator.

Preferably, the nucleic acid construct comprises nucleic acid sequences encoding four polypeptides having the enzymatic activities of (a) erythro-β-hydroxyaspartate aldolase belonging to the EC class 4.1.3.14, (b) erythro-β-hydroxyaspartate dehydratase belonging to the EC class 4.3.1.20, (c) iminosuccinate reductase comprising an amino acid sequence selected from SEQ ID NO: 1-299, or an amino acid sequence having at least 80% sequence identity to a sequence selected from SEQ ID NO: 1-299; (d) aspartate-glyoxylate transaminase comprising an amino acid sequence selected from SEQ ID NO: 300-599, or an amino acid sequence having at least 80% sequence identity to a sequence selected from SEQ ID NO: 300-599, a selection marker nucleic acid, a further nucleic acid sequence targeting said polypeptides to the peroxisomes, and wherein said nucleic acid sequences are operably linked to at least one photosynthetically regulated promoter for expression in a plant and are operably linked to at least one terminator. Preferably, the selection marker nucleic acid is a kanamycin resistance nucleic acid.

In one embodiment of the present invention, the nucleic acid construct comprises (1) a nucleic acid sequence comprising a sequence as set forth in SEQ ID NO: 960, which encodes a polypeptide having the enzymatic activity of erythro-β-hydroxyaspartate aldolase belonging to the EC class 4.1.3.14, (2) a nucleic acid sequence comprising a sequence as set forth in SEQ ID NO: 961, which encodes a polypeptide having the enzymatic activity of erythro-β-hydroxyaspartate dehydratase belonging to the EC class 4.3.1.20, (3) a nucleic acid sequence comprising a sequence as set forth in SEQ ID NO: 959, which encodes a polypeptide having the enzymatic activity of iminosuccinate reductase, and (4) a nucleic acid sequence comprising a sequence as set forth in SEQ ID NO: 962, which encodes a polypeptide having the enzymatic activity of aspartate-glyoxylate transaminase, wherein the nucleic acid sequences (1)-(4) are operably linked to at least one photosynthetically regulated promoter for expression in a plant and are operably linked to at least one terminator.

In a preferred embodiment of the present invention, the nucleic acid construct comprises a nucleic acid sequence as set forth in SEQ ID NO: 986, or a nucleic acid sequence having at least 80%%, more preferably at least 85%, more preferably at least 87%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98% and most preferably at least 99% sequence identity to said sequence.

Figure 1:
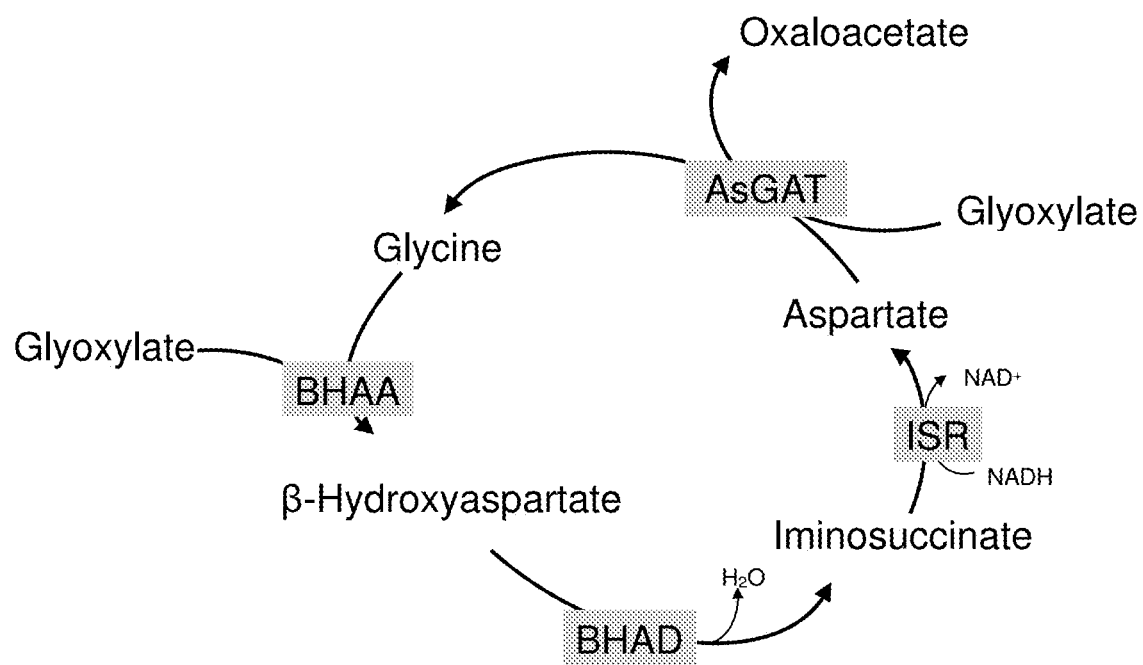
FIG. 1: illustrates the integration of the BHAP as $CO_2$ neutral photorespiratory bypass, the reaction sequence of the β-hydroxyaspartate pathway (as recently elucidated by the inventors), the core sequence of the projected carbon-neutral photorespiration bypass route. Enzymes are indicated in grey boxes aspartate-glyoxylate transaminase (AsGAT), β-hydroxyaspartate aldolase (BHAA), β-hydroxyaspartate dehydratase (BHAD), iminosuccinate reductase (ISRed).

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

EXAMPLES

Abbreviations and Acronyms

AsGAT, AGAT aspartate glyoxylate aminotransferase
ISRed, ISR iminosuccinate reductase
BHA erythro-β-hydroxyaspartate
BHAA β-hydroxyaspartate aldolase
BHAD β-hydroxyaspartate dehydratase
BHAP β-hydroxyaspartate pathway
CBB Calvin-Benson-Bassham
DNA desoxyribo nucleic acid
fwd forward primer FDH formate dehydrogenase
MDH malate dehydrogenase
rev reverse primer Chemicals & Reagents Unless otherwise stated, all chemicals and reagents were acquired from Sigma-Aldrich and were of the highest purity available. Gene synthesis was also performed by Sigma-Aldrich.

Methods

Construction of expression vectors for heterologous expression of the enzymes ISRed, BHAA, BHAD and AsGAT as well as the regulatory protein BHAR The gene encoding for the iminosuccinate reductase enzyme from *Paracoccus denitrificans* DSM 413 (ISRed; nucleic acid sequence shown in SEQ ID NO: 969; amino acid sequence shown in SEQ ID NO: 135) was cloned into the standard expression vector pET16b (commercially available from Merck Millipore). To this end, the ISRed gene was amplified from genomic DNA of *Paracoccus denitrificans* DSM 413 with the primers

```
                                         (SEQ ID NO: 976)
5'-GACGCCTCATATGCTCGTCGTCGCCGAAAAG-3'

(SEQ ID NO: 977)
5'-GCCACTCCTCGAGTCAGATCTCGACCTCTTG-3'
```

The resulting PCR product was digested with the endonucleases NdeI and XhoI and ligated into the expression vector pET16b to create a vector for heterologous expression of ISRed.

The gene encoding for the β-hydroxyaspartate aldolase enzyme from *Paracoccus denitrificans* DSM 413 (BHAA; nucleic acid sequence shown in SEQ ID NO: 970; amino acid sequence shown in SEQ ID NO: 971) was cloned into the standard expression vector pET16b (commercially available from Merck Millipore). To this end, the BHAA gene was amplified from genomic DNA of *Paracoccus denitrificans* DSM 413 with the primers

```
                                         (SEQ ID NO: 978)
5'-GACGCCGCATATGAACGCGAAAACGGATTTC-3'

(SEQ ID NO: 979)
5'-GACACCTGGATCCTCAGTAGCCCTTTCCG-3'
```

The resulting PCR product was digested with the endonucleases NdeI and BamHI and ligated into the expression vector pET16b to create a vector for heterologous expression of BHAA.

The gene encoding for the β-hydroxyaspartate dehydratase enzyme from *Paracoccus denitrificans* DSM 413 (BHAD; nucleic acid sequence shown in SEQ ID NO: 972; amino acid sequence shown in SEQ ID NO: 973) was cloned into the standard expression vector pET16b (commercially available from Merck Millipore).

To this end, the BHAD gene was amplified from genomic DNA of *Paracoccus denitrificans* DSM 413 with the primers

```
                                         (SEQ ID NO: 980)
5'-GACGCTGCATATGTATATCCCGACCTATGAG-3'

(SEQ ID NO: 981)
5'-GACACTCGGATCCTCAGTTCCACGGCAGCTTG-3'
```

The resulting PCR product was digested with the endonucleases NdeI and BamHI and ligated into the expression vector pET16b to create a vector for heterologous expression of BHAD.

The gene encoding for the aspartate-glyoxylate aminotransferase enzyme from *Paracoccus denitrificans* DSM 413 (AsGAT; nucleic acid sequence shown in SEQ ID NO: 433; amino acid sequence shown in SEQ ID NO: 974) was cloned into the standard expression vector pET16b (commercially available from Merck Millipore). To this end, the AsGAT gene was amplified from genomic DNA of *Paracoccus denitrificans* DSM 413 with the primers

```
                                         (SEQ ID NO: 982)
5'-GCCACTACATATGACCAGCCAGAACCC-3'

(SEQ ID NO: 983)
5'-GCCACTCGGATCCTCAGGCGGCTTTCTTCTGC-3'
```

The resulting PCR product was digested with the endonucleases NdeI and BamHI and ligated into the expression vector pET16b to create a vector for heterologous expression of AsGAT.

The gene encoding for the BHA-regulatory protein from *Paracoccus denitrificans* DSM 413 (BHAR; nucleic acid sequence shown in SEQ ID NO: 975; amino acid sequence shown in SEQ ID NO: 732) was cloned into the standard expression vector pET16b (commercially available from Merck Millipore). To this end, the BHAR gene was amplified from genomic DNA of *Paracoccus denitrificans* DSM 413 with the primers

```
                                         (SEQ ID NO: 984)
5'-GCCACATCATATGTCGGTTCAAATCC-3'

(SEQ ID NO: 985)
5'-GTCACTCGGATCCTCAGGCTCTTTCGCCGGCATC-3'
```

The resulting PCR product was digested with the endonucleases NdeI and BamHI and ligated into the expression vector pET16b to create a vector for heterologous expression of BHAR.

Heterologous Expression and Purification of Recombinant Proteins

Enzymes of the BHAP

For heterologous overexpression of the AsGAT, BHAD, BHAA and ISRed enzymes, respectively, the corresponding plasmid encoding the respective enzyme was first transformed into chemically competent *E. coli* BL21 AI cells. The cells were then grown on LB agar plates containing 100 μg mL$^{-1}$ ampicillin at 37° C. overnight. A starter culture in selective LB medium was inoculated from a single colony on the next day and left to grow overnight at 37° C. in a shaking incubator. The starter culture was used on the next day to inoculate an expression culture in selective TB medium in a 1:100 dilution. The expression culture was grown at 37° C. in a shaking incubator to an OD$_{600}$ of 0.5 to 0.7, induced with 0.5 mM IPTG and 0.2% L-arabinose and subsequently grown overnight at 18° C. in a shaking incubator.

Cells were harvested at 6,000×g for 15 min at 4° C. and cell pellets were stored at −20° C. until purification of enzymes. Cell pellets were resuspended in twice their volume of buffer A (300 mM NaCl, 25 mM Tris-HCl pH 8.0, 15 mM imidazole, 1 mM β-mercaptoethanol, 0.1 mM MgCl$_2$, 0.01 mM pyridoxalphosphate (PLP), and one tablet of SIGMAFAST™ protease inhibitor cocktail, EDTA-free per L). The cell suspension was treated with a Sonopuls GM200 sonicator (BANDELIN Electronic GmbH & Co. KG, Berlin, Germany) at an amplitude of 50% in order to lyse the cells and subsequently centrifuged at 50,000×g and 4° C. for 1 h. The filtered supernatant (0.45 µm filter, Sarstedt, Numbrecht, Germany) was loaded onto Protino® Ni-NTA Agarose (Macherey-Nagel, Düren, Germany) in a gravity column, which had previously been equilibrated with 5 column volumes of buffer A. The column was washed with 20 column volumes of buffer A and 5 column volumes of 85% buffer A and 15% buffer B and the His-tagged protein was eluted with buffer B (buffer A with 500 mM imidazole). The eluate was desalted using PD-10 desalting columns (GE Healthcare, Chicago, USA) and buffer C (100 mM NaCl, 25 mM Tris-HCl pH 8.0, 1 mM MgCl$_2$, 0.01 mM PLP, 0.1 mM dithiothreitol (DTT)). This was followed by purification on a size exclusion column (Superdex™ 200 µg, HiLoad™ 16/600; GE Healthcare, Chicago, USA) connected to an ÄKTA Pure system (GE Healthcare, Chicago, USA) using buffer C. 2 mL concentrated protein solution was injected, and flow was kept constant at 1 mL min$^{-1}$. Elution fractions containing pure protein were determined via SDS-PAGE analysis (Laemmli 1970) on 12.5% gels. Purified enzymes in buffer C were used for crystallization or stored at −20° C. in buffer C containing 50% glycerol for later use in enzymatic assays. BhcR was expressed and purified in the same way, except that buffer A contained 100 mM KCl, 20 mM HEPES-KOH pH 7.5, 10 mM MgCl$_2$, 4 mM β-mercaptoethanol, 5% glycerol and one tablet of SIGMAFAST™ protease inhibitor cocktail, EDTA-free per L. Buffer C contained 100 mM KCl, 20 mM HEPES-KOH pH 7.5, 10 mM MgCl$_2$, 5% glycerol and 1 mM DTT. NADH-dependent malate dehydrogenase (Mdh) and NADPH-dependent glyoxylate reductase (GhrA) from *E. coli* were overexpressed using the respective strains from the ASKA collection (Kitagawa, Ara et al. 2005). A starter culture in selective LB medium (34 µg mL$^{-1}$ chloramphenicol) was inoculated from a single colony and left to grow overnight at 37° C. in a shaking incubator. The starter culture was used on the next day to inoculate an expression culture in selective TB medium in a 1:100 dilution. The expression culture was grown at 37° C. in a shaking incubator to an OD$_{600}$ of 0.6, induced with 0.5 mM IPTG and grown for four more hours at 37° C. in a shaking incubator. The enzymes were affinity-purified in the same way as described above, except that buffer A contained 200 mM NaCl, 50 mM potassium phosphate pH 7.0, 15 mM imidazole, 1 mM β-mercaptoethanol, and one tablet of SIGMAFAST™ protease inhibitor cocktail, EDTA-free per L. Buffer C contained 100 mM NaCl, 50 mM potassium phosphate pH 7.0, and 0.1 mM DTT. The purified enzyme was stored at −20° C. in buffer C containing 50% glycerol.

Construction of T-DNA vectors for BHAP enzyme expression and localization studies The construction of all T-DNA vectors used in this study relies on the Golden Gate cloning based MoClo kit (Weber et al., *PLoS ONE* 2011). The MoClo kit contains a set of 95 empty standardized genetic modules that can be used for hierarchical assembly based on the Golden Gate cloning technique. This kit is comprised of plasmids for cloning: promoters, 5' untranslated regions, signal peptides, coding sequences, and terminators. The MoClo kit can be used to assemble any eukaryotic multigene construct. In-vitro synthesized BHAP genes were matured for the Golden Gate system by removing internal BpiI and BsaI restriction enzyme sites. Golden Gate assembly was performed in a 15 µl reaction (10 U BpiI/BsaI, 400 U T4 DNA Ligase, 1×T4 DNA Ligase buffer) with a 50 cycles digestion-ligation cycle (37° C. for 2 minutes and 16° C. for 5 minutes) followed by 5 minutes at 37° C. and 10 minutes at 65° C.

The plant-codon optimized gene for the iminosuccinate reductase enzyme from *Paracoccus denitrificans* DSM 413 (ISRed; nucleic acid sequence shown in SEQ ID NO: 900; amino acid sequence shown in SEQ ID NO: 901) was cloned into the Level 0 vector pICH41308 by golden gate assembly. To this end, the ISRed gene was amplified with the primers

```
                                        (SEQ ID NO: 927)
5'-ttgaagacaaaATGTACCCTTACGATGTGCCTG-3'

(SEQ ID NO: 928)
5'-ttgaagacaaaagcTCAGAGCTTAGAGATCTCGACCTC-3'
```

The plant-codon optimized gene for the β-hydroxyaspartate aldolase enzyme from *Paracoccus denitrificans* DSM 413 (BHAA; nucleic acid sequence shown in SEQ ID NO: 902; amino acid sequence shown in SEQ ID NO: 903) was cloned into the Level 0 vector pICH41308 12 by golden gate assembly. To this end, the BHAA gene was amplified with the primers

```
                                        (SEQ ID NO: 929)
5'-ttgaagacaaaATGCATCACCATCACCACCACCGATTAGCTGTTCTCT

CAGGTCATTTAAACGCTAAGACCGACTTTTC-3'

(SEQ ID NO: 930)
5'-ttgaagacaacgaaccGATCTCGACCTCTTGTGCAACAC-3'
```

In addition, BHAA was cloned in the Level 0 vector pAGM1299 without stop codon for C-terminal fluorescent protein fusion. To this end, the BHAA gene was amplified with the primers

```
                                        (SEQ ID NO: 931)
5'-ttgaagacaaaATGCATCACCATCACCACCACCGATTAGCTGTTCTCT

CAGGTCATTTAAACGCTAAGACCGACTTTTC-3'

(SEQ ID NO: 932)
5'-ttgaagacaacgaaccCTCGACGCAGCCAAGGAAG-3'
```

The plant-codon optimized gene for the β-hydroxyaspartate dehydratase enzyme from *Paracoccus denitrificans* DSM 413 (BHAD; nucleic acid sequence shown in SEQ ID NO: 904; amino acid sequence shown in SEQ ID NO: 905) was cloned into the Level 0 vector pICH41308 by golden gate assembly. To this end, the BHAD gene was amplified with the primers

```
                                        (SEQ ID NO: 933)
5'-ttgaagacaaaATGCATCACCATCACCAC-3'

(SEQ ID NO: 934)
5'-ttgaagacaaaagcTCAAAGCTTGCTGTTCCAC-3'
```

The plant-codon optimized gene for the aspartate:glyoxylate aminotransferase enzyme from *Paracoccus denitrificans* DSM 413 (AsGAT; nucleic acid sequence shown in SEQ ID NO: 906; amino acid sequence shown in SEQ ID NO: 907) was cloned into the Level 0 vector pICH41308 by golden gate assembly. To this end, the AsGAT gene was amplified with the primers

```
                                        (SEQ ID NO: 935)
5'-ttgaagacaaaATGTACCCTTACGATGTGC-3'

(SEQ ID NO: 936)
5'-ttgaagacaaaagcTCAAAGCTTAGAAGCAGCC-3'
```

Construction of higher-level T-DNA constructs (Level 1 & 2, Level P & M) followed the MoClo kit-based guidelines (Weber et al., 2011). The generated constructs are described in Tables 2, 3 and 4. Used promoter (p), fluorescent proteins and terminators (t) are all part of the MoClo Plant Parts kit. Used vector backbones and linker are also part of the MoClo toolkit. In addition, Arabidopsis UBIQUITIN10 promoter (UBQ10p) was added as part.

For targeting BHAP enzymes to the chloroplast and mitochondria a similar cloning strategy will be used to generate the corresponding construct for verification of the localization and implementing the pathway in plants. Regarding the localization only C-terminal fluorescent fusions can be generated due to the N-terminal localization of the target peptide for mitochondrial or chloroplastic localization.

TABLE 2

Constructs used for localization studies

| Name | Insert 1 | Vector/ backbone | Plant Resistance | Bacterial Resistance |
|---|---|---|---|---|
| pMR211 | AtUBQ10p::mCherry-ASGAT::S/RbcS3Ct | pICH86966 | Kanamycin | Kanamycin |
| pMR213 | AtUBQ10p::mCherry-BHAD::S/RbcS3Ct | pICH86966 | Kanamycin | Kanamycin |
| pMR214G | AtUBQ10p::eGFP-ISR::S/RbcS3Ct | pICH86966 | Kanamycin | Kanamycin |
| pMR261 | AtUBQ10p::BHAA-mCherry::S/RbcS3Ct | pICH86966 | Kanamycin | Kanamycin |

TABLE 3

Constructs for in vitro enzyme assays

| Name | Transcriptional unit 1 | Transcriptional unit 2 | Linker | Vector/ backbone | Bacterial Resistance |
|---|---|---|---|---|---|
| pMR225N | AtRbcS2Bp::BHAA::AtuOCSt | AtRbcS1Bp::BHAD::AtuNOSt | pICH50881 | pAGM8031 | Spectinomycin |
| pMR226 | AtRbcS3Bp::ISR::35St | AtCaBp::ASGAT::S/RbcS3Ct | pICH50900 | pAGM8055 | Spectinomycin |
| pMR268 | AtRbcS1Bp::BHAD::AtuNosT | AtRbcS3Bp::ISR::35St | pICH50892 | pAGM8043 | Spectinomycin |

TABLE 4

Construct for stable P-hydroxyaspartate pathway implementation

| Name | pMR228N |
|---|---|
| Transcriptional unit 1 | AtRbcS2Bp::BHAA::AtuOCSt |
| Transcriptional unit 2 | AtRbcS1Bp::BHAD::AtuNOSt |
| Transcriptional unit 3 | AtRbcS3Bp::ISR::35St |
| Transcriptional unit 4 | AtCaBp::ASGAT::S/RbcS3Ct |
| Linker | pICH79290 |
| Vector/backbone | pICH75322 |
| Plant Resistance | Kanamycin |
| Bacterial Resistance | Kanamycin |

Transformation of *Agrobacterium tumefaciens*

*Agrobacterium tumefaciens* GV3103::pMP90 (*A. tumefaciens*) was transformed with corresponding T-DNA constructs by electroporation. Electrocompetent *A. tumefaciens* cells were thawed on ice and 1 μg plasmid DNA was added and afterwards cells were transferred into a 2 mm electroporation cuvette (Eppendorf, Germany) and electroporated using an Eppendorf electroporator 2510 (Eppendorf, Germany) set to 25 μF, 2.4 kV, 200 Ohm, and 5 msec pulse length. After electroporation cells were resuspended in 1 ml YEP medium and incubated at 28° C. with shaking at 200 ppm before plating on YEP plates containing the appropriate antibiotics.

Transformation of *Arabidopsis thaliana*

*Arabidopsis* was transformed by floral dipping, which is a simplified method for *Agrobacterium*-mediated transformation of *Arabidopsis thaliana*. 300 ml *A. tumefaciens* overnight culture was pelleted at 1,600×g for 10 min at RT. The bacterial pellet was resuspended in 400 ml 5% (w/v) sucrose and supplemented with 0.02% (v/v) Silwet L-77. *Arabidopsis* were dipped into the *A. tumefaciens* suspension for 1 min and kept in the dark for 1 day before being transferred back to the growth chamber until seed harvesting.

Transient Expression of BHAP Enzymes in *Nicotiana benthamiana*, Protoplast Isolation and Confocal Microscopy

*A. tumefaciens* cultures were diluted to an OD600 of 0.4 in infiltration medium (10 mM MgCl2, 10 mM MES pH 5.7, 100 μM acetosyringon) and diluted equally for coexpression of two T-DNAs. Leaves of four-week-old greenhouse grown *N. benthamiana* plants were infiltrated using a syringe without a needle for transient expression. For leaf disc assays two leaf discs (1 cm diameter each) per leaf, were infiltrated similarly and harvested 5 days post infection (5 dpi).

Leaf discs were grinded, using glassbeads and windmill, and resuspended in 400 μl extraction buffer (50 mM potassium phosphate pH 7.5, 5 mM MgCl2, 1 mM EDTA, 0.1% (v/v) Triton-X 100). After centrifugation for 10 minutes at 12,000 rpm at 4° C. the supernatant was used for SDS-PAGE analysis following immunoblot analysis. For localization studies leaves were harvested two days post infection and protoplasts were isolated for confocal microscopy. Dissected leaf material was vacuum infiltrated with protoplast digestion solution (1.5% Cellulase R-10, 0.4% Macerozyme R-10, 0.4 M Mannitol, 20 mM KCl, 20 mM MES pH 5.6, 10 mM CaCl2, 0.1% BSA) and incubated at 30° C. for two hours. Protoplasts were transferred to a new tube and allowed to sediment and afterwards resuspended in W5 solution (154 mM NaCl, 25 mM $CaCl_2$, 5 mM KCl, 2 mM MES pH 5.6). Protoplasts were analysed using a Zeiss LSM 780 confocal microscope and Zeiss ZEN software. Excitation/emission wavelength settings were used as follows: CFP (458 nm/458-514 nm), GFP (488 nm/490-550 nm), mCherry (561 nm/580-625 nm), and chlorophyll A (488 nm/640-710 nm). Fiji software was used for image processing.

BHAP Enzyme Activity Assays

Each BHAP enzyme was assayed individually after 5 days transient expression in *N. benthamiana*. Leaf discs were grinded, using glass beads and windmill, and resuspended in 700 µl extraction buffer (50 mM potassium phosphate pH 7.5, 5 mM MgCl$_2$, 1 mM EDTA, 0.1% (v/v) Triton-X 100). After centrifugation for 10 minutes at 12,000 rpm at 4° C. and 25 µl of the supernatant was used per enzyme assay. All assays were carried out at 30° C. in a total volume of 300 µl. The oxidation of NADH was followed at 340 nm on a Cary 60 UV-Vis photospectometer (Agilent) in quartz cuvettes with a path length of 10 mm (Hellma Analytics).

The reaction mixture to assay AsGAT activity contained 100 mM potassium phosphate buffer pH 7.5, 0.1 mM PLP, 0.2 mM NADH, 5 mM glyoxylate, 20 mM aspartate, 25 µl of N. benthamiana leaf disc extract and 8.75 µg MDH enzyme.

The reaction mixture to assay BHAA activity contained 100 mM potassium phosphate buffer pH 7.5, 0.1 mM PLP, 0.2 mM NADH, 0.5 mM MgCl$_2$, 5 mM glyoxylate, 10 mM glycine, 25 µl of N. benthamiana leaf disc extract and 7 µg purified BHAD and 7 µg purified ISRed enzyme.

The reaction mixture to assay BHAD activity contained 100 mM potassium phosphate buffer pH 7.5, 0.1 mM PLP, 0.2 mM NADH, 2 mM β-hydroxyaspartate (BHA), 25 µl of N. benthamiana leaf disc extract and 7 µg purified ISRed enzyme. BHA (=(2R,3S)-β-hydroxyaspartate) was custom-synthesized for the inventors by the company NewChem (Newcastle upon Tyne, United Kingdom), and was determined to be >95% pure by NMR analysis.

The reaction mixture to assay ISRed activity contained 100 mM potassium phosphate buffer pH 7.5, 0.1 mM PLP, 0.2 mM NADH, 2 mM BHA, 25 µl of N. benthamiana leaf disc extract and 7 µg purified BHAD enzyme. The formation of aspartate by ISRed activity was confirmed by LC-MS/MS. To take samples for LC-MS/MS analysis, the reaction volume of the assay was increased to 600 µl and contained 100 mM potassium phosphate buffer pH 7.5, 0.1 mM PLP, 0.2 mM NADH, 2 mM BHA, 25 µl of N. benthamiana leaf disc extract and 7 µg purified BHAD enzyme. 90 µL aliquots were taken after 0, 1, 2 and 3 minutes and the reaction was immediately stopped by addition of formic acid (4% final concentration). The samples were centrifuged at 17,000×g and 4° C. for 15 min and the supernatant was subsequently used for LC-MS analysis.

The LC-MS measurements were done using an Agilent 6550 Funnel Q-TOF LC-MS system equipped with an electrospray ionization source set to negative ionization mode. Liquid chromatography (LC) was carried out as follows: The analytes were separated on an aminopropyl column (30 mm×2 mm, particle size 3 µm, 100 Å, Luna NH$_2$, Phenomenex inc.) using a mobile phase system comprised of 95:5 20 mM ammonium acetate pH 9.3 (adjusted with ammonium hydroxide to a final concentration of approximately 10 mM)/acetonitrile (A) and acetonitrile (B). Chromatographic separation was carried out using the following gradient condition at a flow rate of 250 µl min-1: 0 min 85% B; 3.5 min 0% B, 7 min, 0% B, 7.5 min 85% B, 8 min 85% B. Column oven and autosampler temperature were maintained at 15° C. The ESI source was set to the following parameters: Capillary voltage was set at 3.5 kV and nitrogen gas was used as nebulizing (20 psig), drying (13 l/min, 225 C) and sheath gas (12 l/min, 400° C.). The QTOF mass detector was calibrated prior to measurement using an ESI-L Low Concentration Tuning Mix (Agilent) with residuals and corrected residuals less than 2 ppm and 1 ppm respectively. MS data were acquired with a scan range of 50-600 m/z. Autorecalibration was carried out using 113 m/z as reference mass. Subsequent peak integration of all analytes was performed using the eMZed software, which is specific for the development of LCMS data analysis.

The same procedure was used to assay the activity of the enzymes purified from E. Coli BL21 implemented with the BHAP:

The above described assay conditions are used to measure individually BHAP enzyme activity in the generated Arabidopsis thaliana BHAP plants. Therefore, leaves of four-week old transgenic lines expressing the BHAP are harvested and total leaf protein is extracted as stated above. The optimal volume of crude leaf extract in the enzymatic assays needs to be optimized. In order to distinguish between aspartate formation by ISRed activity and leaf extract aspartate aminotransferase activity, $^{15}$N-glycine will be used in BHAA assays as substrate to measure $^{15}$N-aspartate enrichment over time by LC/MS.

Verification of BHAP Implementation in Arabidopsis thaliana.

Seeds of primary transformants with the nucleic acid construct were harvested four weeks after transformation and plated on 0.5× Murashige & Skoog (MS) medium containing kanamycin as selection marker (50 µg/ml). After stratification at 4° C. for 2 days in the dark, seeds were grown in a growth chamber (100 µmol photons m$^{-2}$s$^{-1}$) at high CO$_2$ concentrations (3000 ppm) under normal day conditions (12 h day/12 h night, 22° C.). Seedlings were grown on plates for 12 days and transferred to soil and grown under the same conditions as described.

Leaves of four-week-old plants were harvested in liquid nitrogen for genomic DNA isolation. Leaf material was grinded using glass beads and windmill and resuspended in 400 µl extraction buffer (250 mM Tris-HCl pH 7.5, 250 mM NaCl, 25 mM EDTA, 0.5% (w/v) SDS) and 150 µl 3 M potassium acetate. After vortexing samples were centrifuged at 12,000 rpm for 5 minutes. Supernatant was transferred to a new tube containing 550 µl 100% isopropanol and inverted several times. Samples were again centrifuges for 5 minutes at 12,000 rpm and the supernatant was discarded. DNA pellet was washed with 300 µl 70% (v/v) ethanol and centrifuged for 5 minutes at 12,000 rpm. The supernatant was discarded and the pellet after 10 minutes ethanol evaporation resuspended in 50 µl TE-Buffer (10 mM Tris-HCl pH 7.5, 0.1 mM EDTA). 2 µl of resuspended DNA was used for PCR. The complete integration of all four BHAP enzymes was verified using a combination of forward and reverse primers specific for the promoter and the coding sequence.

Integration of AsGAT under control of the chlorophyll A binding protein promoter was verified with the primers

```
                                    (SEQ ID NO: 937)
        5'-GACTAGCCAATAGCAACCTC-3'

(SEQ ID NO: 938)
        5'-CTCTGATAGCAGACACGGAAT-3'
```

Integration of BHAA under control of the RubisCO small subunit 2B promoter was verified with the primers

```
                                    (SEQ ID NO: 939)
        5'-CCAGTAGCCATACACATTCAC-3'

(SEQ ID NO: 940)
        5'-GCTTGTCGTTCACCTTGAG-3'
```

Integration of BHAD under control of the RubisCO small subunit 1B promoter was verified with the primers (SEQ ID NO: 941)
5'-GAGCCAAAGCAACCGATC-3'

(SEQ ID NO: 942)
5'-GATCTGTAAGCGTCATCAGC-3'

Integration of ISRed under control of RubisCO small subunit 3B promoter was verified with the primers (SEQ ID NO: 943)
5'-GAAAGGAGCCAAAAGCAAC-3'

(SEQ ID NO: 944)
5'-GTCCAACACCAGTTCCATC-3'

Successful gDNA isolation was confirmed by amplification of the *Arabidopsis* housekeeping gene ACTIN 2 (AT3G18780) using primers (SEQ ID NO: 945)
5'-GTTGGGATGAACCAGAAGGA-3'

(SEQ ID NO: 946)
5'-GAACCACCGATCCAGACACT-3'

To verify homozygosity of the ggt1 mutant a gene-specific/T-DNA specific primer pair was used. Wildtype GGT1 was amplified using primers (SEQ ID NO: 947)
5'-CCTTGCCCTTGGCTCTAGAACC-3'

(SEQ ID NO: 948)
5'-GTCATACCTAAACCGCCTGAAGTC-3'

The T-DNA integration in the GGT1 locus in the ggt1 mutant was verified using primers (SEQ ID NO: 949)
5'-TAACTCTCCCCACTCTTTGCC-3'

(SEQ ID NO: 950)
5'-ATATTGACCATCATACTCATTGC-3'

TABLE 5

Description of the Sequence List

| SEQ ID No | Description | Type |
|---|---|---|
| 1-299 | IsRed enzyme | Amino Acid |
| 300-599 | AsGAT enzyme | Amino Acid |
| 600-899 | β-hydroxyaspartate regulatory protein | Amino Acid |
| 900 | *Arabidopsis* codon-optimized sequence of IsRed enzyme from *Paracoccus denitrificans* DSM 413 targeted to plant peroxisomes | Nucleic acid |
| 901 | IsRed enzyme from *Paracoccus denitrificans* DSM 413 containing a plant peroxisome targeting sequence | Amino acid |
| 902 | *Arabidopsis* codon-optimized sequence of BHAA enzyme from *Paracoccus denitrificans* DSM 413 containing a plant peroxisome targeting sequence | Nucleic acid |
| 903 | BHAA enzyme from *Paracoccus denitrificans* DSM 413 containing a plant peroxisome targeting sequence | Amino acid |
| 904 | *Arabidopsis* codon-optimized sequence of BHAD enzyme from *Paracoccus denitrificans* DSM 413 targeted to plant peroxisomes | Nucleic acid |
| 905 | BHAD enzyme from *Paracoccus denitrificans* DSM 413 containing a plant peroxisome targeting sequence | Amino acid |
| 906 | *Arabidopsis* codon-optimized sequence of AsGAT enzyme from *Paracoccus denitrificans* DSM 413 targeted to plant peroxisomes | Nucleic acid |
| 907 | AsGAT enzyme from *Paracoccus denitrificans* DSM containing a plant peroxisome targeting sequence | Amino acid |
| 908 | *Arabidopsis* codon-optimized sequence of IsRed enzyme from *Paracoccus denitrificans* DSM 413 and for cytosolic expression | Nucleic acid |
| 909 | IsRed enzyme from *Paracoccus denitrificans* DSM 413 for expression in plant cytosolic expression | Amino acid |
| 910 | *Arabidopsis* codon-optimized sequence of BHAA enzyme from *Paracoccus denitrificans* DSM 413 for expression in plant cytosol | Nucleic acid |
| 911 | BHAA enzyme from *Paracoccus denitrificans* DSM 413 for expression in plant cytosol | Amino acid |
| 912 | *Arabidopsis* codon-optimized sequence of BHAD enzyme from *Paracoccus denitrificans* DSM 413 for expression in plant cytosol | Nucleic acid |
| 913 | BHAD enzyme from *Paracoccus denitrificans* DSM 413 for expression in plant cytosol | Amino acid |
| 914 | *Arabidopsis* codon-optimized sequence of AsGAT enzyme from *Paracoccus denitrificans* DSM 413 for expression in plant cytosol | Nucleic acid |
| 915 | AsGAT enzyme from *Paracoccus denitrificans* DSM 413 for expression in plant cytosol | Amino acid |
| 916 | *Arabidopsis* Ferredoxin-2 chloroplastic target peptide for N-terminal fusion to target BHAP proteins to plant chloroplasts. | Nucleic acid |
| 917 | *Arabidopsis* Ferredoxin-2 chloroplastic target peptide for N-terminal fusion to target BHAP proteins to plant chloroplasts. | Amino acid |
| 918 | *Arabidopsis* serine hydroxymethyl transferase target peptide for N-terminal fusion to target BHAP proteins to plant mitochondria. | Nucleic acid |
| 919 | *Arabidopsis* serine hydroxymethyl transferase target peptide for N-terminal fusion to target BHAP proteins to plant mitochondria | Amino acid |

TABLE 5-continued

Description of the Sequence List

| SEQ ID No | Description | Type |
|---|---|---|
| 920 | Nucleic acid sequence coding *Dicosoma* sp. red fluorescent protein (m Cherry) | Nucleic acid |
| 921 | *Dicosoma* sp. red fluorescent protein (mCherry) | Amino acid |
| 922 | Nucleic acid sequence coding enhanced green fluorescent protein | Nucleic acid |
| 923 | enhanced green fluorescent protein | Amino acid |
| 924 | *Agrobacterium tumefaciens* NOS promoter | Nucleic acid |
| 925 | *Agrobacterium tumefaciens* MAS promoter | Nucleic acid |
| 926 | cauliflower mosaic virus 35S promoter | Nucleic acid |
| 927 | primer for cloning of IsRed in pICH41308, fwd | Nucleic Acid |
| 928 | primer for cloning of IsRed in pICH41308, rev | Nucleic Acid |
| 929 | primer for cloning of BHAA in pICH41308, fwd | Nucleic Acid |
| 930 | primer for cloning of BHAA in pICH41308, rev | Nucleic Acid |
| 931 | primer for cloning of BHAA in pAGM1299 without stop codon, fwd | Nucleic Acid |
| 932 | primer for cloning of BHAA in pAGM1299 without stop codon, rev | Nucleic Acid |
| 933 | primer for cloning of BHAD in pICH41308, fwd | Nucleic Acid |
| 934 | primer for cloning of BHAD in pICH41308, rev | Nucleic Acid |
| 935 | primer for cloning of AsGAT in pICH41308, fwd | Nucleic Acid |
| 936 | primer for cloning of AsGAT in pICH41308, rev | Nucleic Acid |
| 937 | Primer used to assess the integration of AsGAT under control of chlorophyll A binding protein promoter, fwd | Nucleic Acid |
| 938 | Primer used to assess the integration of AsGAT under control of chlorophyll A binding protein promoter, rev | Nucleic Acid |
| 939 | Primer used to assess the integration of BHAA under control of RubisCO small subunit 2B promoter, fwd | Nucleic Acid |
| 940 | Primer used to assess the integration of BHAA under control of RubisCO small subunit 2B promoter, rev | Nucleic Acid |
| 941 | Primer used to assess the integration of BHAD under control of RubisCO small subunit 1B promoter, fwd | Nucleic Acid |
| 942 | Primer used to assess the integration of BHAD under control of RubisCO small subunit 1B promoter, rev | Nucleic Acid |
| 943 | Primer used to assess the integration of ISRed under control of RubisCO small subunit 3B promoter, fwd | Nucleic Acid |
| 944 | Primer used to assess the integration of ISRed under control of RubisCO small subunit 3B promoter, rev | Nucleic Acid |
| 945 | Primer for Actin 2 amplification, fwd | Nucleic Acid |
| 946 | Primer for Actin 2 amplification, rev | Nucleic Acid |
| 947 | Primer for wildtype GGT1 amplification, fwd | Nucleic Acid |
| 948 | Primer for wildtype GGT1 amplification, rev | Nucleic Acid |
| 949 | primer for verification of T-DNA integration in the GGT1 locus, fwd | Nucleic Acid |
| 950 | primer for verification of T-DNA integration in the GGT1 locus, rev | Nucleic Acid |
| 951 | nucleic acid sequence coding the peroxisomal targeting signal 2 (PTS2) from *Arabidopsis* peroxisomal citrate synthase 3 (At2g42790) | Nucleic acid |
| 952 | peroxisomal targeting signal 2 (PTS2) from *Arabidopsis* peroxisomal citrate synthase 3 (At2g42790) | Amino acid |
| 953 | Pden_3919 BHAA | Amino acid |
| 954 | Pden_3920 BHAD | Amino acid |
| 955 | BHAA enzyme derived from *Paracoccus denitrificans* DSM 413 containing a plant peroxisome targeting sequence and without tag for immunoblot analysis | Amino acid |
| 956 | BHAD enzyme from *Paracoccus denitrificans* DSM 413 containing a plant peroxisome targeting sequence and without tags for immunoblot | Amino acid |
| 957 | ISRed enzyme derived from *Paracoccus denitrificans* DSM 413 containing a plant peroxisome targeting sequence and without tags for immunoblot | Amino acid |
| 958 | AsGAT enzyme derived from *Paracoccus denitrificans* DSM 413 containing a plant peroxisome targeting sequence and without tags for immunoblot analysis | Amino acid |
| 959 | Arabidopsis codon-optimized sequence of BHAA enzyme from *Paracoccus denitrificans* DSM 413 containing a plant peroxisome targeting sequence, and without tags for immunoblot analysis | Nucleic acid |
| 960 | Arabidopsis codon-optimized sequence of BHAD enzyme from *Paracoccus denitrificans* DSM 413 containing a plant peroxisome targeting sequence and without tags for imunoblot analysis | Nucleic acid |
| 961 | Arabidopsis codon-optimized sequence of ISRed enzyme from *Paracoccus denitrificans* DSM containing a plant peroxisome targeting sequence and without tags for immunoblot analysis | Nucleic acid |
| 962 | Arabidopsis codon-optimized sequence of AsGAT enzyme from *Paracoccus denitrificans* DSM 413 containing a plant peroxisome targeting sequence, and without tags for immunoblot analysis | Nucleic acid |
| 963 | Arabidopsis codon-optimized sequence of BHAA enzyme from *Paracoccus denitrificans* DSM 413 for expression in plant cytosol | Nucleic acid |
| 964 | Arabidopsis codon-optimized sequence of BHAD enzyme from *Paracoccus denitrificans* DSM 413 for expression in plant cytosol | Nucleic acid |

TABLE 5-continued

Description of the Sequence List

| SEQ ID No | Description | Type |
|---|---|---|
| 965 | Arabidopsis codon-optimized sequence of IsRed enzyme from *Paracoccus denitrificans* DSM 413 for expression in plant cytosol | Nucleic acid |
| 966 | Arabidopsis codon-optimized sequence of AsGAT enzyme from *Paracoccus denitrificans* DSM 413 for expression in plant cytosol | Nucleic acid |
| 967 | Conserved amino acid sequence of the IsRed enzymes | Amino acid |
| 968 | Conserved amino acid sequence of the AsGAT enzymes | Amino acid |
| 969 | IsRed enzyme from *Paracoccus denitrificans* DSM 413 | Nucleic acid |
| 970 | BHAA enzyme from *Paracoccus denitrificans* DSM 413 | Nucleic acid |
| 971 | BHAA enzyme from *Paracoccus denitrificans* DSM 413 | Amino acid |
| 972 | BHAD enzyme from *Paracoccus denitrificans* DSM 413 | Nucleic acid |
| 973 | BHAD enzyme from *Paracoccus denitrificans* DSM 413 | Amino acid |
| 974 | AsGAT enzyme from *Paracoccus denitrificans* DSM 413 | Nucleic acid |
| 975 | BHA-regulatory protein from *Paracoccus denitrificans* DSM 413 | Nucleic acid |
| 976 | Primer for cloning of ISRed from *Paracoccus denitrificans* DSM 413 into pET16b, fwd | Nucleic acid |
| 977 | Primer for cloning of ISRed from *Paracoccus denitrificans* DSM 413 into pET16b, rev | Nucleic acid |
| 978 | Primer for cloning of BHAA from *Paracoccus denitrificans* DSM 413 into pET16b, fwd | Nucleic acid |
| 979 | Primer for cloning of BHAA from *Paracoccus denitrificans* DSM 413 into pET16b, rev | Nucleic acid |
| 980 | Primer for cloning of BHAD from *Paracoccus denitrificans* DSM 413 into pET16b, fwd | Nucleic acid |
| 981 | Primer for cloning of BHAD from *Paracoccus denitrificans* DSM 413 into pET16b, rev | Nucleic acid |
| 982 | Primer for cloning of AsGAT from *Paracoccus denitrificans* DSM 413 into pET16b, fwd | Nucleic acid |
| 983 | Primer for cloning of AsGAT from *Paracoccus denitrificans* DSM 413 into pET16b, rev | Nucleic acid |
| 984 | Primer for cloning of BHAR from *Paracoccus denitrificans* DSM 413 into pET16b, fwd | Nucleic acid |
| 985 | Primer for cloning of BHAR from *Paracoccus denitrificans* DSM 413 into pET16b, rev | Nucleic acid |
| 986 | multigene T-DNA construct pMR228N for BHAP implementation in plant peroxisomes. | Nucleic acid |

Phenotypic Analysis

*Arabidopsis thaliana* seeds are plated on 0.5× Murashige & Skoog (MS) medium containing kanamycin as selection marker (50 µg/ml) for segregation analysis to confirm homozygous integration of the nucleic acid construct (T-DNA). Seeds of homozygous plants are plated on 0.5× Murashige & Skoog (MS) medium without selection marker. After stratification at 4° C. for 2 days in the dark, seeds are grown in a growth chamber (100 µmol photons $m^{-2}s^{-1}$) at ambient 002 concentrations (400 ppm) under normal day conditions (12 h day/12 h night, 22° C.). Alternatively, plants are shifted between ambient $CO_2$ concentrations (400 ppm) and high $CO_2$ concentrations (3000 ppm) under normal day conditions (12 h day/12 h night, 22° C.). In order to determine phenotypic parameters, the plants are imaged and rosette size and leaf size are analysed using Fiji software. Leaf fresh weight is measured by weighting leaves from comparable developmental stages.

As a matter of photorespiratory stress protection chlorophyll fluorescence ($F_v/F_m$) upon shift between low (100 ppm $CO_2$), ambient and high $CO_2$ concentrations are measured using an Imaging PAM (Walz, Germany). Seedlings are dark exposed for 15 minutes and exposed to saturating light pulse (10 000 µmol photons $m^{-2}$ $s^{-1}$ for 800 ms). Photosynthetic parameters are recorded with pre-illuminates plants grown at 100 µmol photons $m^{-2}$ $s^{-1}$ with stepwise increasing light intensities up to 1600 µmol photons $m^{-2}$ $s^{-1}$ using the Dual-PAM. ETR I, ETR II, NPQ, Y(NPQ), Y(NO) are calculated by the Dual-PAM 100 software.

Gas Exchange Measurements

Photosynthetic rates are measured using a LI-6400XT portable photosynthesis analyzer (LI-COR Environmental). Conditions were maintained at 1500 µmol $m^{-2}$ $s^{-1}$ photon flux and $A/C_i$ curves are determined by stepwise changes in external $CO_2$ supply ranging from 50 to 2000 ppm. Based on the initial slope of the $A/C_i$ curve the maximum rate of carboxylation ($V_{cmax}$) and maximum electron transport rate ($J_{max}$) is calculated. Inhibition of photosynthesis by oxygen is assessed by determining the $CO_2$ compensation point in the presence of different oxygen concentrations (2-40%). The $CO_2$ compensation point is less affected in the BHAP implemented lines as compared to the wild type.

Transformation of *Nicotiana tabacum*.

The implementation of the BHAP in tobacco is achieved by transforming *Nicotiana tabacum* leaf discs with pMR228N as described in Gallois et al. in Methods in Molecular Biology 1995, vol. 49, p. 39.

Free Ammonium Quantification in Plant Tissue

Free ammonium was quantified in plant tissue using a colorimetric assay as previously described. In detail, 10 mg of grinded material was resuspended in 100 µL chloroform and 200 µl 100 mM HCl. Samples were rotated for 15 minutes at 4° C. and centrifuged at 12,000×g for 10 minutes at 4° C. 150 µl of the aqueous phase was transferred to a new tube containing 10 mg washed charcoal and centrifuged for 5 minutes at 4° C. at 16,000×g. 50 µl of the supernatant was mixed with 50 µl 100 mM HCl and used for further processing. Assay conditions were as follow. 20 µl of sample were mixed with 100 µl solution A, containing 1% (w/v) phenol and 0.005% (w/v) sodium nitroprusside solution in water and 100 μl solution B, containing 1% (v/v) sodium hypochlorite and 0.5% (w/v) sodium hydroxide solution in water. The assay mixture was incubated at 37° C. for 30 minutes and absorbance was measured using a Synergy™ HTX Multi-Mode Microplate Reader (BioTek). Total ammonium quantification was calculated based on a standard curve.

Metabolite Profiling

For metabolite profiling green tissue of 14 days old seedlings was harvested by immediate quenching with liquid nitrogen at the middle of the light phase. Frozen material was grinded using a precooled mortar and pestil. Grinded material was aliquoted under continuous liquid nitrogen expose to avoid sample thawing. 50 mg of leaf material is used for metabolite extraction using a one-phase extraction protocol as previously described. In detail, 1.5 ml of extraction mix, containing water:methanol:chloroform at ratio 1:2.5:1 and 5 μM ribitol as internal standard, was added to frozen material. Samples were vortexed for 20 seconds, rotated for 6 minutes at 4° C. and centrifuged for 2 minutes at 20,000×g at room temperature. The supernatant was transferred to a new tube and stored at −80° C. before further processing. For metabolite profiling by gas chromatography-mass spectrometry (GC-MS), 50 μl of extract was dried using a speed vacuum concentrator. Dried samples were placed in the Gerstel MPS 2 XL autosampler for automatic sample derivatization using methoxyamine hydrochloride and N-Methyl-N-(trimethylsilyl) trifluoroacetamide before injection. The GC-MS device is a 7200 accurate mass Q-TOF GC/MS (Agilent). For relative quantification metabolite peak areas are normalized to the internal extraction standard and the material fresh weight.

Example 1—Kinetic Characterization of the Enzymes of the β-Hydroxyaspartate Pathway (BHAP) and Reconstruction of the BHAP In Vitro The genes encoding for the four enzymes of the BHAP in the genome of *Paracoccus denitrificans* DSM 413 were identified and these four proteins were heterologously expressed in *E. coli*. The four enzymes were purified and subjected to kinetic characterization by conducting suitable enzyme assays. Kinetic parameters of the enzymes are summarized in Table 1. The complete reaction sequence of the BHAP, catalyzed by these four enzymes, is shown in FIG. 1.

Figure 2:
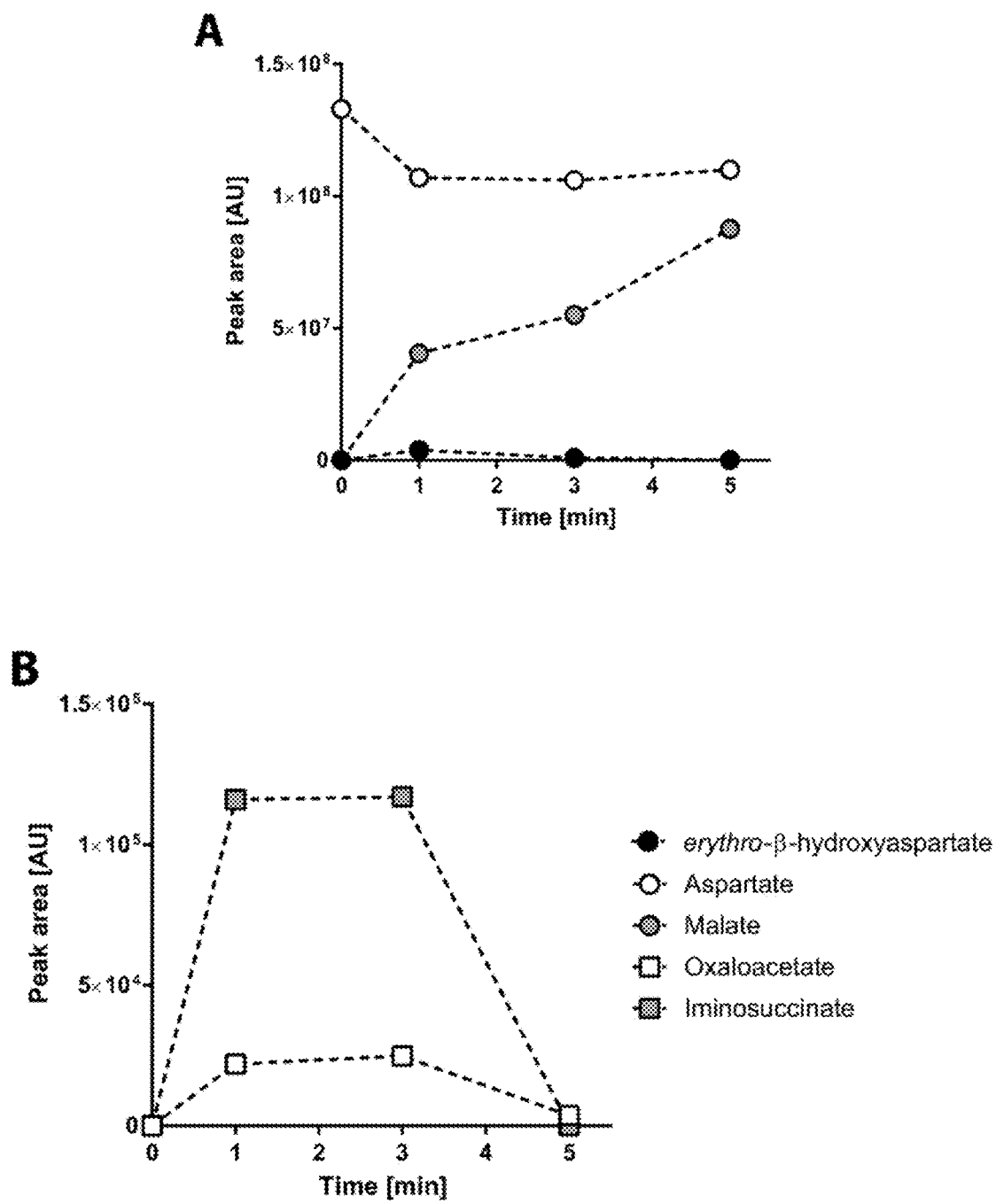
FIG. 2: In vitro assay with the four enzymes of the BHAP and malate dehydrogenase. Metabolites were quantified via LC-MS analysis. Glyoxylate (not measurable with this method) and aspartate (white circles) were added to produce malate (grey circles), as shown in panel A. The intermediate metabolites of the pathway (erythro-β-hydroxyaspartate, oxaloacetate, iminosuccinate) were also measured successfully, as shown in panel A and B.

To assess the efficiency of the BHAP in converting its input molecule (glyoxylate) into its output molecule (oxaloacetate), a combined assay of all four enzymes was conducted. Additionally, the enzymes malate dehydrogenase (MDH) and formate dehydrogenase (FDH) were added. MDH converts oxaloacetate into malate, which can be analyzed well via LC-MS, while FDH as cofactor regeneration system is required for the regeneration of the cofactor NADH by oxidation of formate to carbon dioxide. The results of this assay are shown in FIG. 2 and demonstrate that the BHAP converts glyoxylate into malate with high speed and efficiency.

Furthermore, this assay demonstrates that the concentration of the required co-substrate aspartate remains largely the same over the course of the assay. With these in vitro results the stability and effectiveness of the enzyme-catalyzed reaction network is demonstrated that is the BHAP, which suggests that the pathway can also be used with high efficiency in a host microorganism, especially since it would not deplete the intracellular aspartate pool too much.

TABLE 6

Kinetic data of the four enzymes of the β-hydroxyaspartate pathway.

| Enzyme | Substrate | app. $k_{cat}$ [s$^{-1}$] | app. $K_M$ [mM] | app. $k_{cat}/K_M$ [M$^{-1}$ s$^{-1}$] |
|---|---|---|---|---|
| ISRed | Iminosuccinate | 201.04 ± 10.20 | 0.088 ± 0.010 | 2.29 * 106 |
|  | NADH | — | 0.023 ± 0.003 | — |
|  | NADPH | — | 0.33 ± 0.05 | — |
| BHAA | Glyoxylate | 85.96 ± 3.64 | 0.23 ± 0.03 | 3.72 * 105 |
|  | Glycine | 90.98 ± 02.41 | 4.31 ± 0.34 | 2.11 * 104 |
|  | (2R, 3S)-β-hydroxy-aspartate | 33.11 ± 1.29 | 0.28 ± 0.03 | 1.18 * 105 |
|  | D-Threonine | 76.21 ± 2.49 | 9.24 ± 0.86 | 8.25 * 103 |
| BHAD | (2R, 3S)-β-hydroxy-aspartate | 35.01 ± 0.82 | 0.20 ± 0.02 | 1.75 * 105 |
| AsGAT | Glyoxylate | 58.07 ± 0.82 | 0.43 ± 0.02 | 1.34 * 105 |
|  | L-Aspartate | 56.36 ± 0.73 | 2.51 ± 0.10 | 2.25 * 104 |
|  | Glycine | 0.76 ± 0.01 | 9.52 ± 0.40 | 7.97 * 101 |
|  | Oxaloacetate | 0.76 ± 0.02 | 2.90 ± 0.27 | 2.62 * 102 |
|  | L-Serine | 8.82 ± 0.31 | 2.10 ± 0.24 | 4.20 * 103 |
|  | L-Glutamate | 5.03 ± 0.26 | 20.62 ± 2.33 | 2.44 * 102 |

Example 2—Designing the β-Hydroxyaspartate Pathway (BHAP) for Implementation in Plant Peroxisomes Initially, the β-hydroxyaspartate pathway (BHAP) from *Paracoccus denitrificans* DSM 413 has been implemented in plant peroxisomes due to high expected concentrations of photorespiration-derived glyoxylate (FIG. 1). The genes coding the four enzymes (aspartate-glyoxylate aminotransferase (AsGAT), β-hydroxyaspartate aldolase (BHAA), β-hydroxyaspartate dehydratase(BHAD) and iminosuccinate reductase (ISRed)) of the BHAP were codon-optimized for expression in *Arabidopsis thaliana* (henceforth: *Arabidopsis*) by gene synthesis (Sigma Aldrich, Germany). In order to target the BHAP enzymes to plant peroxisomes, synthetic fusions with peroxisomal targeting sequences were generated. AsGAT, BHAD and ISRed were C-terminally fused with the three amino acid peroxisomal targeting signal 1 (PTS1; serine-lysine-leucine). C-terminal fusion of BHAA with PTS1 inactivated the enzyme and therefore, BHAA was N-terminally fused with the peroxisomal targeting signal 2 (PTS2) from *Arabidopsis* peroxisomal citrate synthase 3 (At2g42790). Furthermore, all four enzymes were fused with tags for immunoblot analysis. AsGAT and ISRed were N-terminally fused with a hemagglutinin A (HA)-tag and BHAA and BHAD were N-terminally fused with a 6× histidine tag (6×His).

fied via LC-MS. As shown, both aspartate and malate were formed in the respective enzyme assay (FIG. 8), with the ratio of malate aspartate being approximately 100 towards the end of the assay (FIG. 9).

TABLE 7

Required enzymes to convert 2-phosphoglycolate into oxaloacetate in the projected photorespiratory bypass. Substrates and products of all enzymes are given, with possible cofactors indicated in brackets.

| Reaction/ Enzyme no. | EC no. of enzyme to be employed | Enzyme to be employed | Examples for organisms | Natural plant localization | Substrate(s) | Product(s) | Reference |
|---|---|---|---|---|---|---|---|
| a | 2.6.1.X (not yet given) | aspartate-glyoxylate transaminase | *Paracoccus denitrificans* | — | aspartate, glyoxylate | oxaloacetate, glycine | |
| b | 4.1.3.14 | erythro-β-hydroxyaspartate aldolase | *Paracoccus denitrificans* | — | glyoxylate, glycine | erythro-β-hydroxyaspartate | |
| c | 4.3.1.20 (former 4.2.1.38) | erythro-β-hydroxyaspartate dehydratase | *Paracoccus denitrificans* | — | erythro-β-hydroxyaspartate | iminosuccinate, $H_2O$ | Biochem. J. 1965, 97(2), 547 |
| d | 1.5.1.X (not yet given) | iminosuccinate reductase | *Paracoccus denitrificans* | — | iminosuccinate (NADH) | aspartate (NAD) | |

Example 3—Demonstrating BHAP Enzyme Targeting to Plant Peroxisomes

Figure 3:
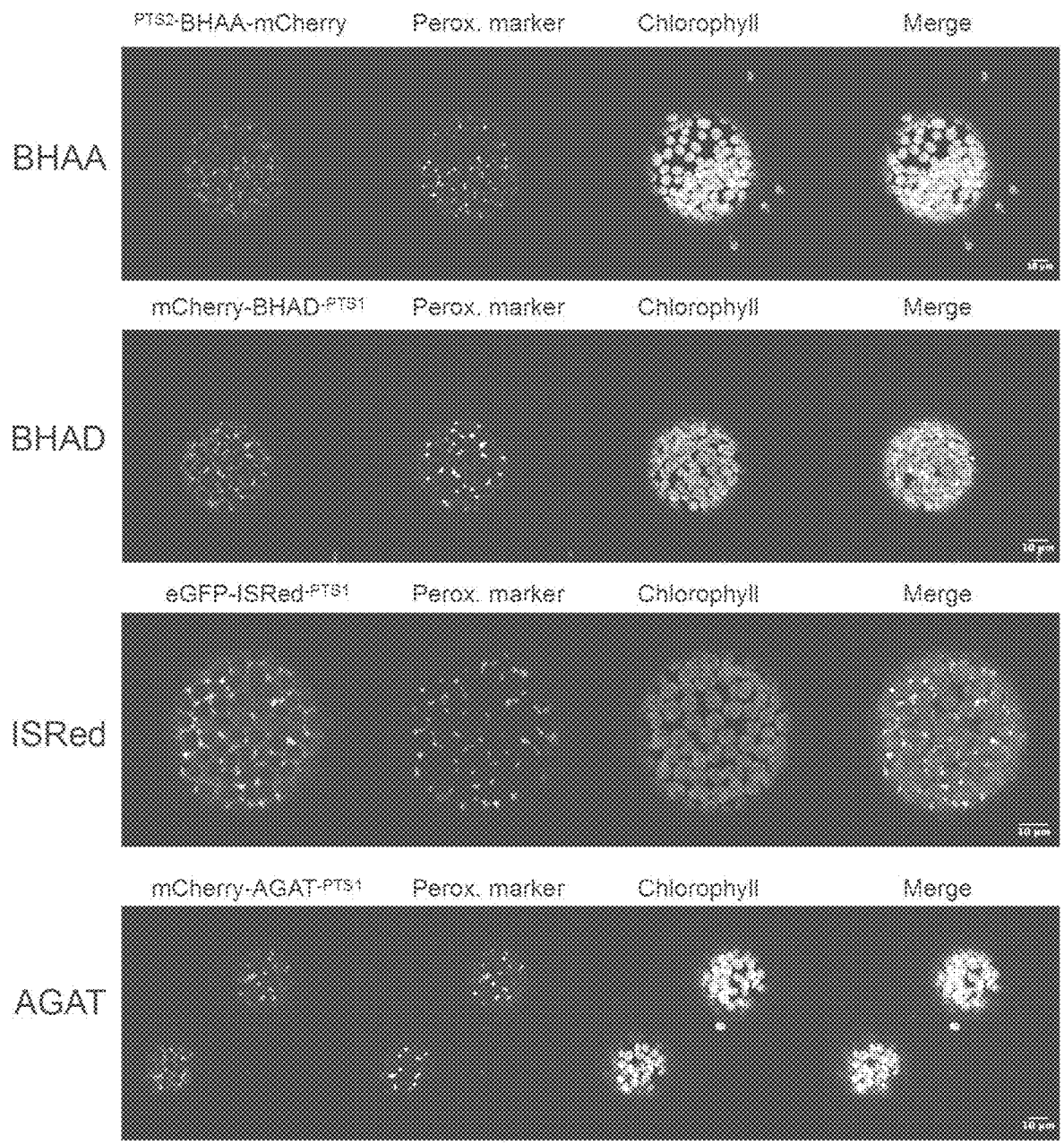
FIG. 3: shows the localization of BHAP enzymes to plant peroxisomes. Peroxisomal localization of four BHAP enzymes by co-localization studies in N. benthamiana protoplasts. Fluorescent fusion constructs were transiently expressed in N. benthamiana and protoplasts were isolated 2 days post infection. Overlap of BHAP fluorescent with peroxisomal marker (perox. marker) verify the successfully targeting of BHAP enzymes to peroxisomes.
Figure 4:
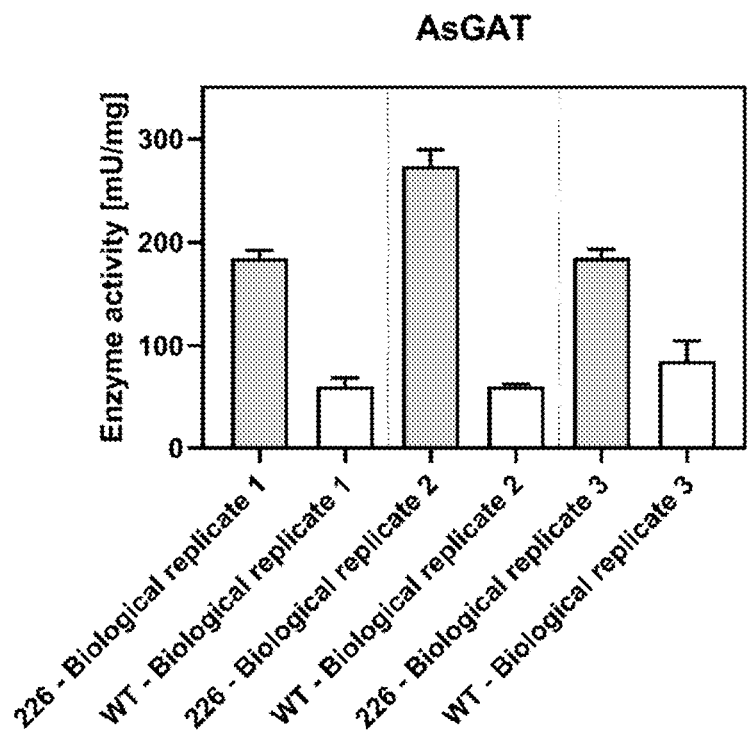
FIG. 4: shows the activity of the AsGAT enzyme in N. benthamiana plants. Enzyme activity was measured in plant cell extracts of plant lines with transient expression of the enzyme (226) and compared to WT plant cell extracts. As shown, the enzyme activity is clearly present in the transiently expressing plants and considerably higher than the background activity in WT plants. Experiments were performed in 3 biological replicates.
Figure 5:
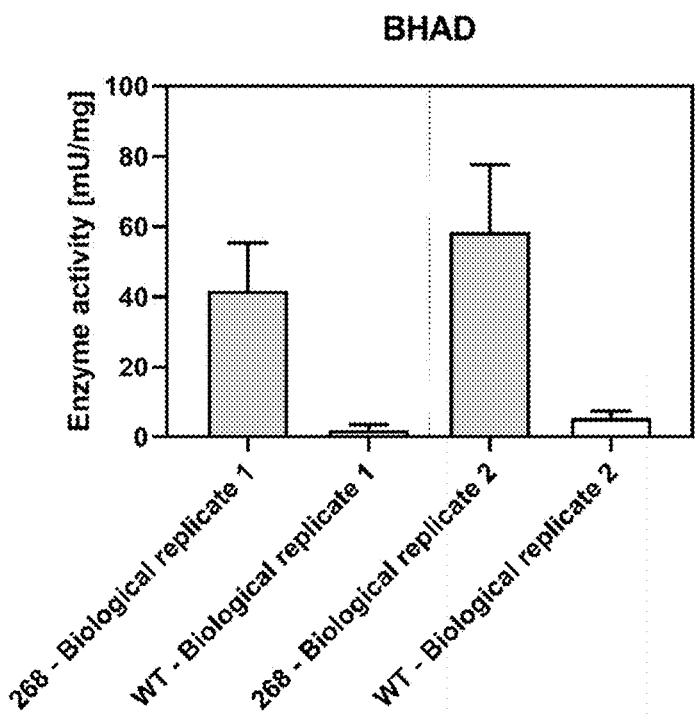
FIG. 5: shows the activity of the BHAD enzyme in N. benthamiana plants. Enzyme activity was measured in plant cell extracts of plant lines with transient expression of the enzyme (268) and compared to WT plant cell extracts. As shown, the enzyme activity is clearly present in the transiently expressing plants and considerably higher than the background activity in WT plants. Experiments were performed in two biological replicates.
Figure 6:
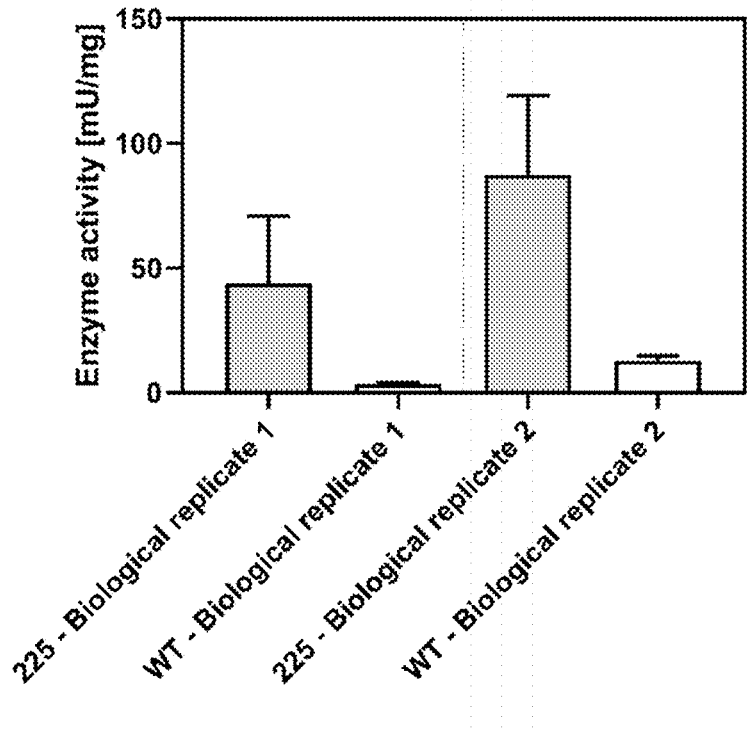
FIG. 6: shows the activity of the BHAA enzyme in N. benthamiana plants. Enzyme activity was measured in plant cell extracts of plant lines with transient expression of the enzyme (225) and compared to WT plant cell extracts. As shown, the enzyme activity is clearly present in the transiently expressing plants and considerably higher than the background activity in WT plants. Experiments were performed in two biological replicates.
Figure 7:
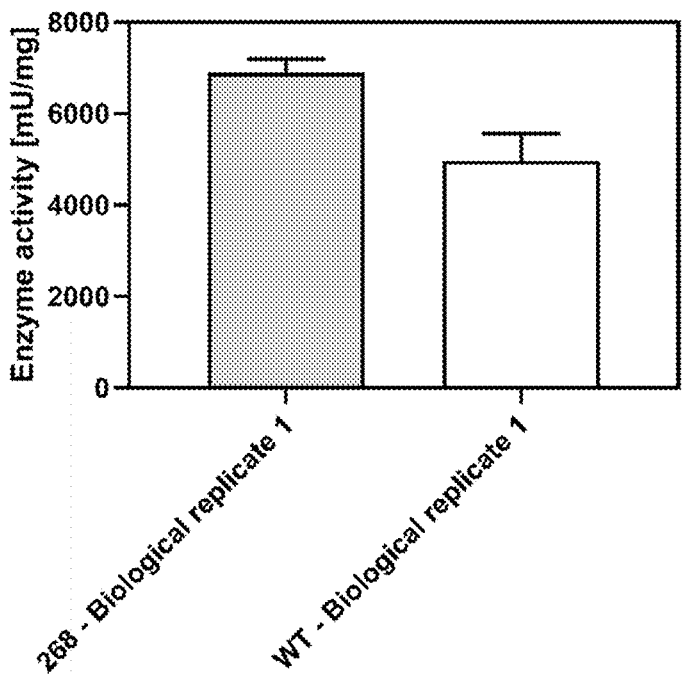
FIG. 7: shows the activity of the IsRed enzyme in N. benthamiana plants. Enzyme activity was measured in plant cell extracts of plant lines with transient expression of the enzyme (225) and compared to WT plant cell extracts. As shown, the enzyme activity is clearly present in the transiently expressing plants and considerably higher than the background activity in WT plants. Experiments were performed in one biological replicate.

The inventors were able to demonstrate the correct localization of BHAP enzymes in plant peroxisomes (FIG. 3). Peroxisomal targeting of BHAP enzymes was confirmed via co-localization studies in *Nicotiana benthamiana* (*N. benthamiana*). Fluorescent fusion constructs of BHAP enzymes were co-infiltrated with a peroxisomal organellar marker for transient expression in *N. benthamiana* and co-localization was confirmed by confocal microscopy with isolated *N. benthamiana* protoplasts (FIG. 3). AsGAT and BHAD were N-terminally fused with *Dicosoma* sp. red fluorescent protein (mCherry) (nucleic acid sequence and amino acid sequence: SEQ ID NOs 920 and 921, respectively). ISRED was N-terminally fused with an enhanced green fluorescent protein (eGFP) (nucleic acid sequence and amino acid sequence: SEQ ID NO 922 and 923, respectively) and BHAA was C-terminally fused with *Dicosoma* sp. red fluorescent mCherry. Used peroxisomal markers are either mCherry or cyan fluorescent protein (CFP) with a C-terminal PTS1 fusion. The *Arabidopsis* UBIQUITIN10 promoter was used as promoter for all constructs including organellar markers.

Example 4—BHAP Enzymatic Activity in Plants

Figure 8:
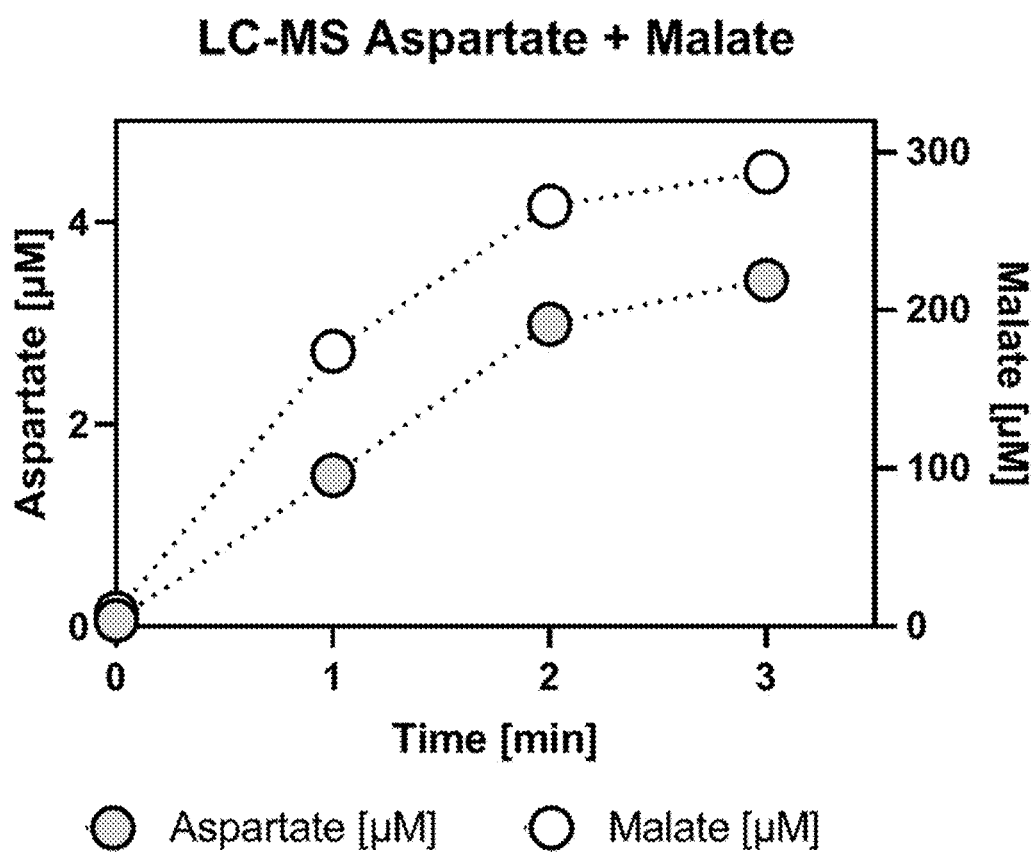
FIG. 8: shows the formation of aspartate (via IsRed) and malate (via malate dehydrogenase) as quantified via LC-MS in N. benthamiana plant cell extracts of plant lines with transient expression of IsRed. This experiment was performed in order to differentiate the activity of IsRed from malate dehydrogenase activity. As shown, both aspartate and malate were formed in the respective enzyme assay.
Figure 9:
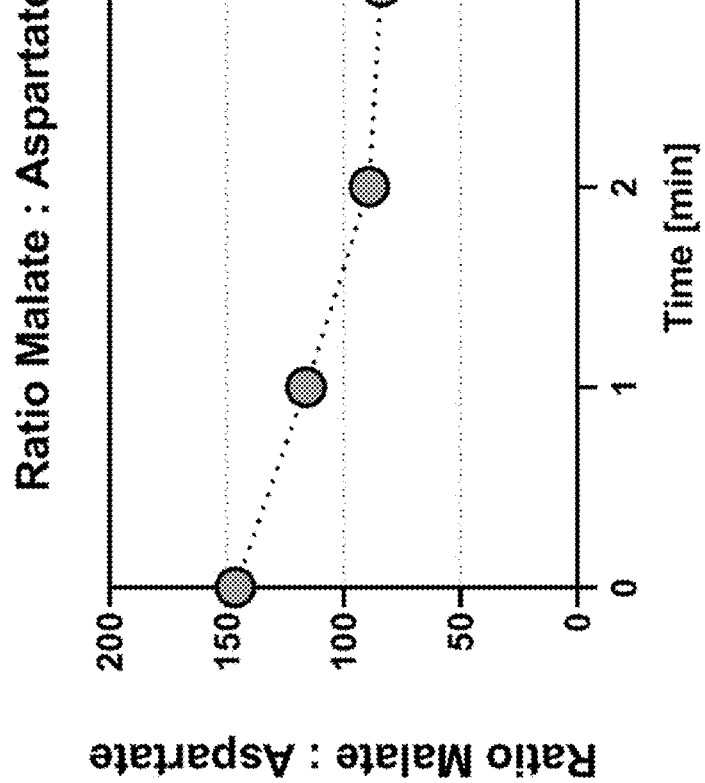
FIG. 9: shows the ratio malate:aspartate formed in the experiment described in FIG. 7. As shown, both aspartate and malate were formed in the respective enzyme assay, with the ratio of malate:aspartate being approximately 100 towards the end of the assay.

The inventors were able to demonstrate activity of each of the BHAP enzymes in *N. benthamiana* leaf extracts (FIG. 4-9). Aspartate formation by ISRed activity was validated by time-dependent increase of aspartate concentration via LC-MS (FIG. 8 and FIG. 9).

Figure 10:
FIG. 10: A schematic representation of the generated T-DNA nucleic acid construct (pMR228N, BHAP, SEQ ID NO: 986) is shown. Abbreviations: *Arabidopsis thaliana* (At), *Agrobacterium tumefaciens* (Atu), *Solanum lycopersicum* (Sl), Arabidopsis RubisCO small subunit 2B promoter (AtRbcS2Bp), beta-hydroxyaspartate aldolase (BHAA), *Agrobacterium tumefaciens* octopine synthase terminator (AtuOCSt), Arabidopsis RubisCO small subunit 1B promoter (AtRbcS1 Bp), beta-hydroxyaspartate dehydratase (BHAD), *Agrobacterium tumefaciens* nopaline synthase terminator (AtuNOSt), Arabidopsis RubisCO small subunit 3B promoter (AtRbS3Bp), iminosuccinate reductase (ISRed), 35S terminator derived from the Cauliflower Mosaic Virus (35St), Arabidopsis chlorophyll A binding protein promoter (AtCaBp), aspartate-glyoxylate aminotransferase (AsGAT), *Solanum lycopersicum* RubisCO small subunit 3C terminator (S/RbcS3Ct), Kanamycin Resistance gene (KanR).
Figure 11:
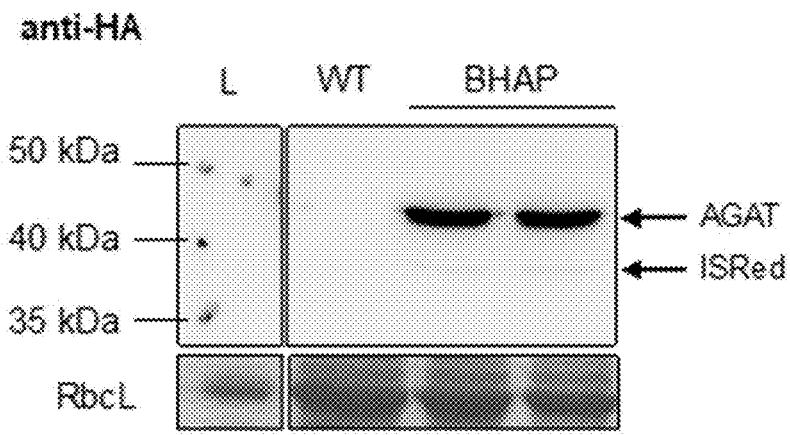
FIG. 11: Transient expression of BHAP T-DNA construct in N. benthamiana. Immunoblot analysis of N. benthamiana leaf discs transiently expressing the BHAP T-DNA construct for 5 days post infection with Agrobacteria. Enzyme expression was verified by using anti-HA-HRP antibody for the detection of AsGAT (43.90 kDa) and ISRed (35.09 kDa). Non-infiltrated leaves (WT) served as negative control.
Figure 12:
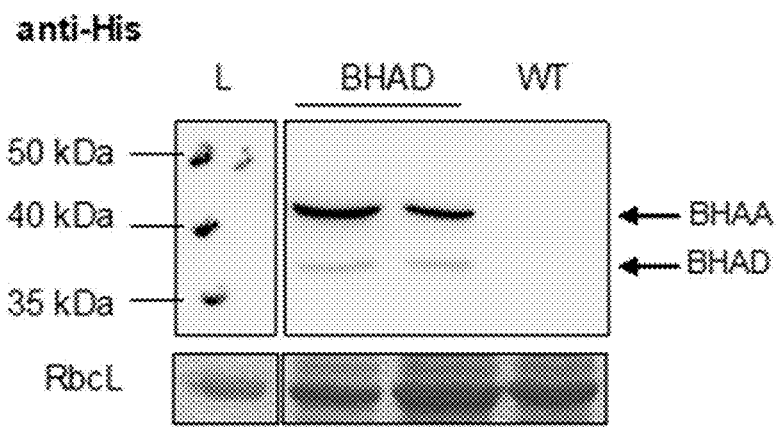
FIG. 12: Transient expression of BHAP T-DNA construct in N. benthamiana. Enzyme expression was verified by using anti-HIS-HRP antibody for the detection of BHAA (42.439 kDa) and BHAD (35.17 kDa). Non-infiltrated leaves (WT) served as negative control.

BHAP enzymes were individually tested for enzymatic activity in plant cell extracts of plant lines with transient expression of each enzyme, and compared to WT plant cell extracts. BHAP enzymes were transiently expressed in *N. benthamiana* leaf discs under the same photosynthetic promoter as contained in the multigene T-DNA construct for stable implementation of the BHAP in *Arabidopsis* (pMR228N, FIG. 9). As shown in FIGS. 4-7, the enzyme activity is clearly present in the transiently expressing plants and considerably higher than the background activity in WT plants. To differentiate the activity of IsRed from malate dehydrogenase activity, the formation of aspartate (via IsRed) and malate (via malate dehydrogenase) was quanti- Example 5—Multigene BHAP T-DNA Construct for in Planta Implementation and Verification of Construct Functionality The inventors constructed a multigene T-DNA nucleic acid construct for implementation of the BHAP in plants (FIG. 10). Although constitutive expression of multiple transgenes is a predominant approach in plants and might be of interest for future studies, the inventors use a fine-tuned approach of BHAP expression in plants. Within the multigene nucleic acid construct, each BHAP enzyme is expressed under its own photosynthetically regulated promoter, restricting BHAP expression to photosynthetic tissue and coupling BHAP expression to light and high photorespiratory metabolic flux. In our case, AsGAT is expressed under *Arabidopsis* chlorophyll A binding protein promoter (AT1g29930) and BHAA under the *Arabidopsis* RubisCO small subunit 2B promoter (AT5g38420). BHAD is expressed under the *Arabidopsis* RubisCO small subunit 1B promoter (AT5g38430) and ISRed expressed under the *Arabidopsis* RubisCO small subunit 3B promoter (AT5g38410). Moreover, the nucleic acid construct comprises terminator sequences operably linked to the nucleic acid sequence coding each polypeptide. These terminators are: *Agrobacterium tumefaciens* octopine synthase terminator (AtuOCSt, contained in SEQ ID NO 986, residues 2169-2882), *Agrobacterium tumefaciens* nopaline synthase terminator (AtuNOSt, contained in SEQ ID NO 986, residues 4773-5027), 35S terminator derived from the Cauliflower Mosaic Virus (35St, contained in SEQ ID NO 986, residues 6969-7172), *Solanum lycopersicum* RubisCO small subunit 3C terminator (SlRbcS3Ct, contained in SEQ ID NO 986, residues 9275-9556). Kanamycin resistance is used as selectable marker. Functionality of the T-DNA construct, regarding expression of all four enzymes was verified by transient expression in *N. benthamiana*, followed by immunoblot analysis (FIG. 11 and FIG. 12). *N. benthamiana* leaf discs transiently were infected with Agrobacteria to express the BHAP T-DNA construct, and were collected after 5 days for immunoblot analysis. Expression of the enzymes was verified by using anti-HA-HRP antibody for the detection of AsGAT (43.90 kDa) and ISRed (35.09 kDa). Anti-HIS-HRP antibody was used for the detection of BHAA (42.439 kDa) and BHAD (35.17 kDa). Non-infiltrated leaves (WT) served as negative control.

Example 6—BHAP Implementation in Plants

Figure 16:
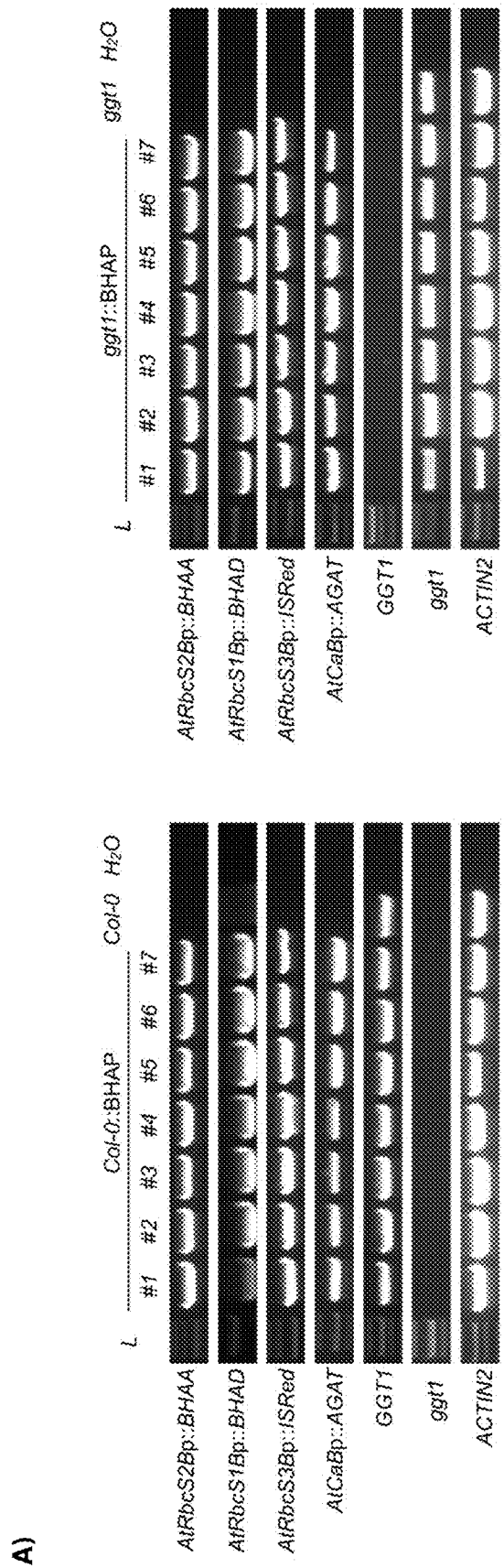
FIG. 16: BHAP implementation in *Arabidopsis* Col-0 and ggt1 mutant. A) Genomic DNA of seven independent primary transformants (#1-7) per background genotype was isolated and presence of the BHAP genes was verified using a promoter/coding sequence specific primer combination. ACTIN2 served as control to prove genomic DNA isolation. Homozygosity of the ggt1 mutant was confirmed using T-DNA specific primer and wildtype GGT1 gene served as control. B) Analysis BHAP implementation in *Arabidopsis* transformed lines with Col-0 and ggt1 background that were used in the experiments of Examples 7-9, FIGS. 17-23. CTRL1: Col-0, T-1: Col::BHAP #1, T-2: Col::BHAP #2, CTRL2: ggt1-1, T-3: ggt1-1::BHAP #1, T-4: ggt1-1::BHAP #2.
Figure 17:
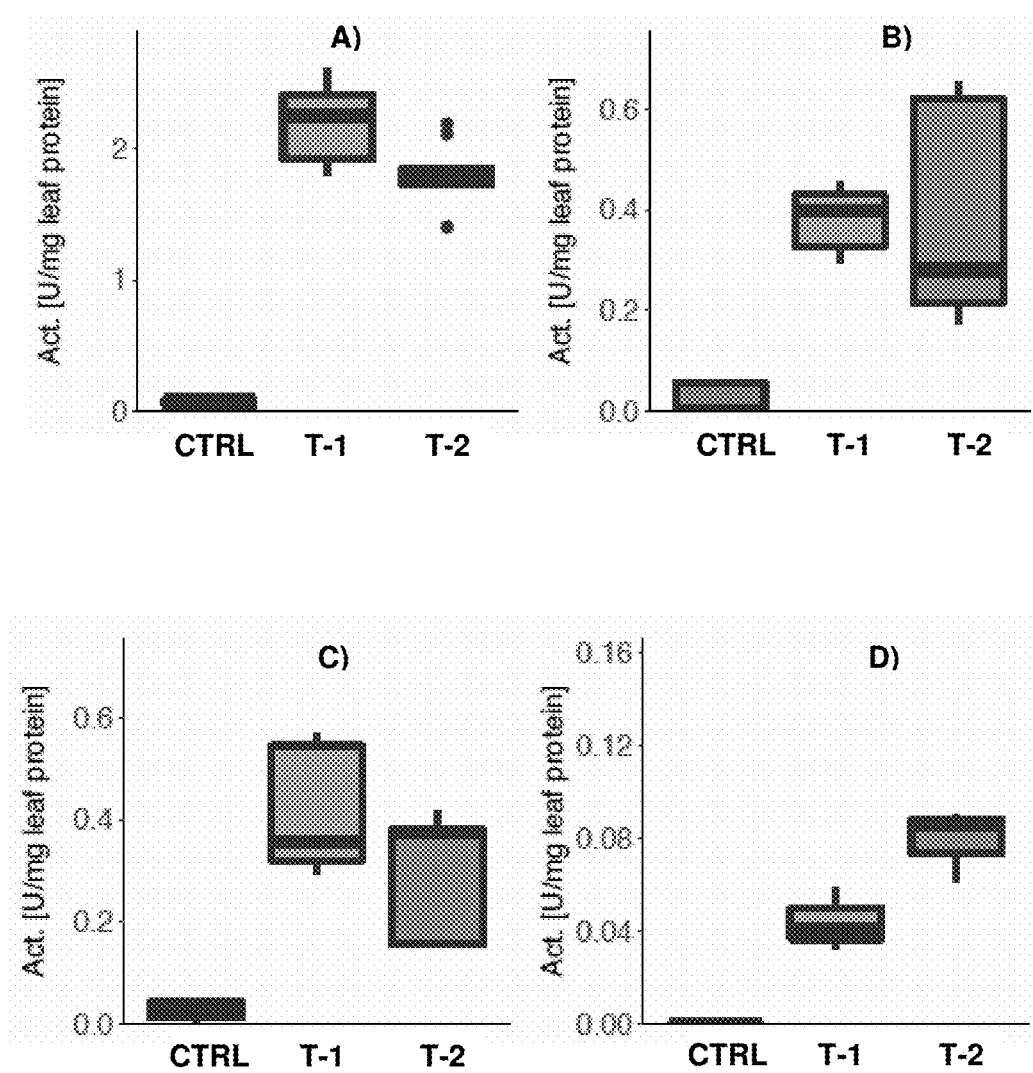
FIG. 17: shows the BHAP enzyme activity in transgenic *Arabidopsis* plants. BHAP enzyme activity was measured in total leaf extracts from 28 days old air-grown plants. A) aspartate:glyoxylate aminotransferase (AGAT), B) β-hydroxyaspartate aldolase (BHAA), β-hydroxyaspartate dehydratase (BHAD), D) Combined activities of BHAA, BHAD and ISR. E-G) ISR activity: E)$^{15}$N-aspartate, F) β-hydroxyaspartate, G) malate. The rate of $^{15}$N incorporation into aspartate was quantified over time. Rates of β-hydroxyaspartate and malate production are shown as control. CTRL: ggt1-1, T-1: ggt1-1::BHAP #1, T-2: ggt1-1::BHAP #2. Shown are mean±SD of three technical replicates.

*Arabidopsis* wildtype Col-0 was transformed with the generated BHAP T-DNA construct by floral dipping as described in the Methods. In order to facilitate high pathway flux via the BHAP, the synthetic pathway was also implemented in the *Arabidopsis* ggt1 mutant (GK-649H07). The ggt1 mutant is deficient in the peroxisomal glyoxylate: glutamate aminotransferase 1 (GGT1, At1g23310) and accumulates glyoxylate. The inventors verified complete BHAP implementation in *Arabidopsis* WT and ggt1 mutant by genotyping using for each BHAP enzyme a combination of forward and reverse primers specific for the promoter and the coding sequence, as described in the method section (FIG. 16). The established transgenic lines with the BHAP in WT and ggt1 mutant background were analyzed for phenotype, protein expression and enzymatic activity of all four BHAP enzymes (Examples 8 and 9).

These data strongly suggest that the BHAP can successfully be implemented also in other C3 plant, as oil, cereal, food or biomass crop (Table 8).

TABLE 8

Overview of potential plant species used for implementation of the BHAP. Notably, the crop species presented here are all C3 photosynthesis type crops where photorespiration plays a major role in limiting plant productivity.

| Scientific name | Common name | Purpose |
|---|---|---|
| *Helianthus annuus* | Sunflower | Oil crop |
| *Brassica napus* | Rapeseed/canola | Oil crop |
| *Camelina sativa* | Camelina | Oil crop |
| *Oryza sativa* | Rice | Cereal crop |
| *Hordeum vulgare* | Barley | Cereal crop |
| *Triticum* spp. | Wheat | Cereal crop |
| *Avena sativa* | Oat | Cereal crop |
| *Solanum lycopersicum* | Tomato | Food crop |
| *Solanum tuberosum* | Potato | Food crop |
| *Ipomoea batatas* | Sweet Potatoes | Food crop |
| *Glycine max* | Soybean | Food crop |
| *Beta vulgaris* | Sugar beet | Food crop |
| *Psidium guajava* | Common guava | Food crop |
| *Citrus limon* | Lemon | Food crop |
| *Mangifera indica* | Mango | Food crop |
| *Allium cepa* | Onion | Food crop |
| *Pisum sativum* | Pea | Food crop |
| *Secale cereale* | Roggen | Food crop |
| *Canavalia ensiformis* | Jack bean | Food crop |
| *Medicago sativa* L. | Alfaalfa | Food crop |
| *Prunus amygdalus* L. | Almond | Food crop |
| *Phaseolus vulgaris* L. | Bean | Food crop |
| *Malus* spp. | Apple | Food crop |
| *Prunus armeniaca* L. | Apricot | Food crop |
| *Asparagus officinalis* L. | Asparagus | Food crop |
| *Persea american* P.mill. | Avocado | Food crop |
| *Musa sapientum* L. | Banana | Food crop |
| *Brassica oleracea* L. | Cabbage | Food crop |
| *Daucus carota* L. | Carrot | Food crop |
| *Anacardium occidentale* L. | Cashew | Food crop |
| *Cicer arietinum* L. | Chickpea | Food crop |
| *Theobroma cacao* L. | Cocoa | Food crop |
| *Vigna unguiculata* | Cowpea | Food crop |
| *Vaccinium macro carpon* | Cranberry | Food crop |
| *Cucumis sativus* L. | Cucumber | Food crop |
| *Solanum melongena* L. | Eggplant | Food crop |
| *Vicia faba* L. | Faba bean | Food crop |
| *Ficus carica* L. | Fig | Food crop |
| *Linum usitatissimum* L. | Flaxseed | Food crop |
| *Vitis vinifera* L. | Grape | Food crop |
| *Lactuca* spp. | lettuce | Food crop |
| *Phaseolus lunatus* L. | Lima bean | Food crop |
| *Beta vulgaris* L. | Mangold | Food crop |
| *Olea europea* L. | Olive | Food crop |
| *Citrus sinensis* L. | Orange | Food crop |

TABLE 8-continued

Overview of potential plant species used for implementation of the BHAP. Notably, the crop species presented here are all C3 photosynthesis type crops where photorespiration plays a major role in limiting plant productivity.

| Scientific name | Common name | Purpose |
|---|---|---|
| *Petroselium crispum* | Parsley | Food crop |
| *Prunus persica* L. | Peach | Food crop |
| *Arachis hypogea* L. | Peanut | Food crop |
| *Pyrus communis* L. | Pear | Food crop |
| *Carya illinoinensis* | Pecan | Food crop |
| *Capsicum* spp. | Pepper | Food crop |
| *Cajanus cajan* | Pigeonpea | Food crop |
| *Prunus* spp. | Plum | Food crop |
| *Gossypium hirsutum* L. | Cotton | Fiber crop |
| *Ocimum tenuiflorum* | Tulsi | Medicinal crop |
| *Ricinus communis* L. | Castor bean | Medicinal crop |
| *Taraxacum officinale* | Dandelion | Medicinal crop |
| *Nicotiana tabacum* | Tobacco | Biomass crop |
| *Arabidopsis thaliana* | Thale cress | Scientific research |

Example 7—Establishing Transgenic BHAP Plant Lines

The inventors verified BHAP implementation in *Arabidopsis thaliana* WT Col-0 (FIG. 21) and ggt1 mutant (FIGS. 17-23) on a genomic level. Stable BHAP plant lines were tested for BHAP activity. This included the identification of two independent T-DNA lines per genotype expressing all four BHAP enzymes, i.e. BHAP #1 and #2, using immunoblot analysis. The established lines were segregated for homozygous T-DNA insertion and in vitro BHAP enzyme activity was successfully demonstrated using the previously established assays described in the Method section and in Example 4 (FIG. 17A-G). Thus, stable BHAP plant lines expressing all four enzymes of the BHAP in an active form were identified.

Example 8—Phenotypic Analysis of BHAP Plants

Figure 18:
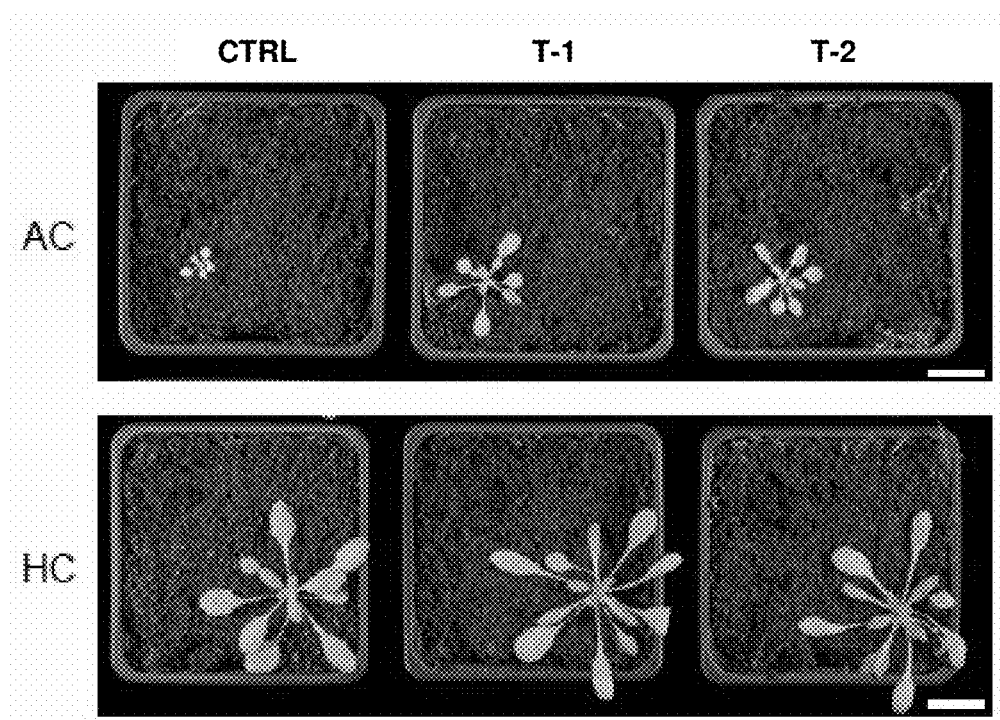
FIG. 18: Phenotype of *Arabidopsis* plants containing the peroxisomal BHAP. A) Plants were grown either in air (400 ppm $CO_2$, AC) or under non-photorespiratory conditions (3000 ppm $CO_2$, HC) in a 12 h light/12 h dark rhythm. Phenotype of plants containing the BHAP in the ggt1-1 mutant background compared to negative control plants. CTRL: ggt1-1, T-1: ggt1-1::BHAP #1, T-2: ggt1-1::BHAP #2. Images were taken 28 days after transfer to light. Scalebar=2 cm.
Figure 19:
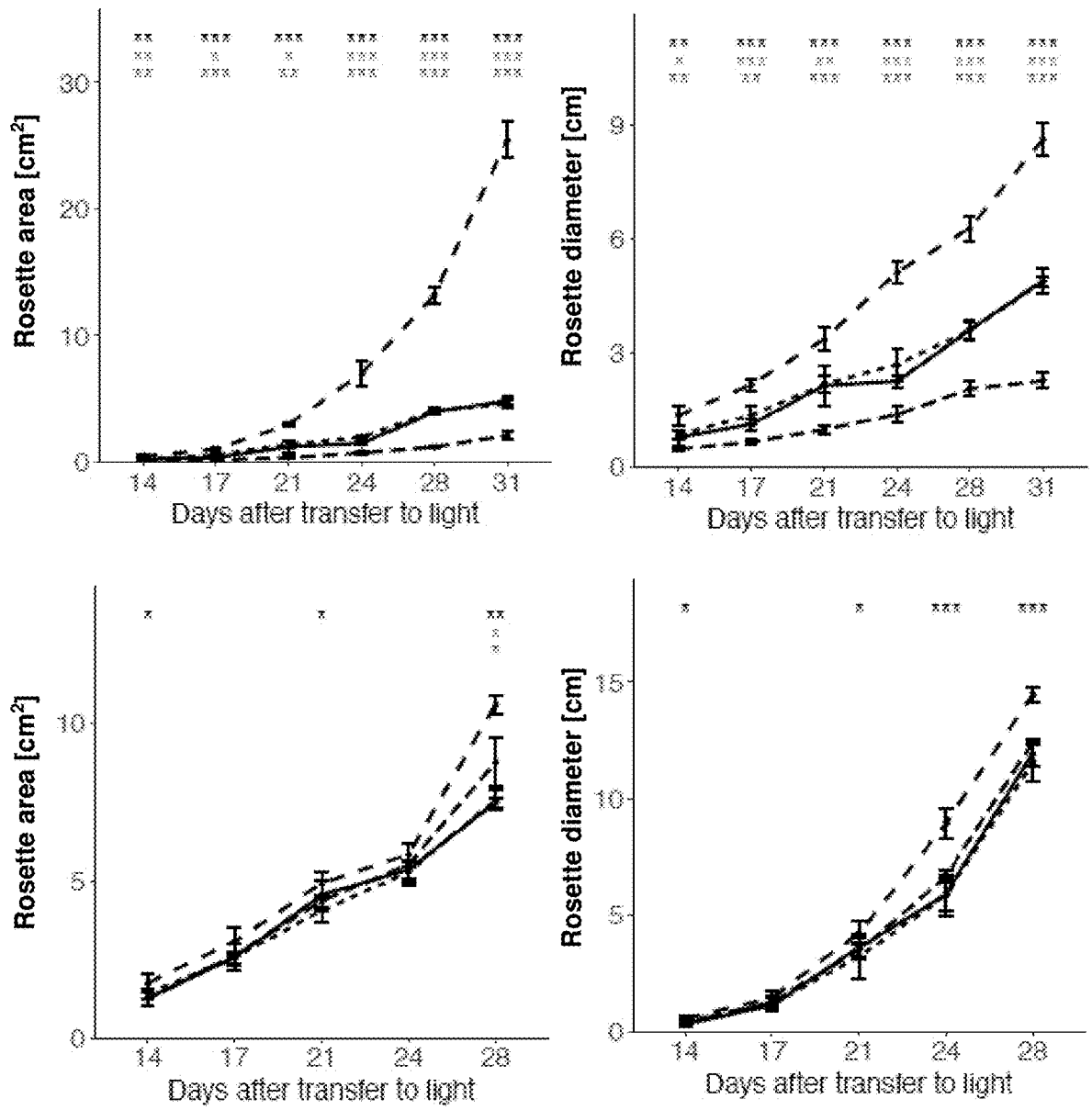
FIG. 19: Phenotype of *Arabidopsis* plants containing the peroxisomal BHAP. Quantification of growth of BHAP-containing plants. Rosette area and rosette diameter were measured over time. CTRL1: Col-0, CTRL2: ggt1-1, T-1: ggt1-1::BHAP #1, T-2: ggt1-1::BHAP #2. Plants were grown either at 3000 ppm $CO_2$ (HC, second row), 400 ppm $CO_2$ (AC, first row). Student's t-test was performed against the ggt1-1 mutant. Asterisks represent the test results for the respective genotype. $p<0.05=*$, $p<0.01=$, $<0.001=*$. n=5.
Figure 20:
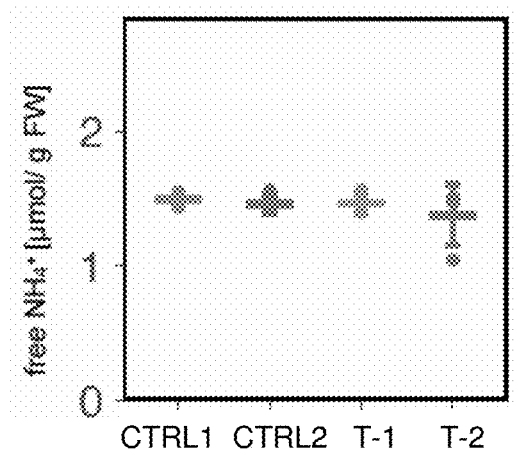
FIG. 20: Quantification of free ammonium in green tissue of 14 days old seedlings. *Arabidopsis* plants were harvested in the middle of the light phase. Plants were grown either at 3000 ppm $CO_2$ (HC), 400 ppm $CO_2$ (AC) or shifted from 3000 ppm $CO_2$ to 400 ppm $CO_2$ three days prior harvest (Shift). CTRL1: Col-0, CTRL2: ggt1-1, T-1: ggt1-1::BHAP #1, T-2: ggt1-1::BHAP #2. Student's t-test against the ggt1-1 mutant. Asterisks represent the test results for the respective genotype. $p<0.05=p<0.01=$, $<0.001=*$. n=4.
Figure 20:
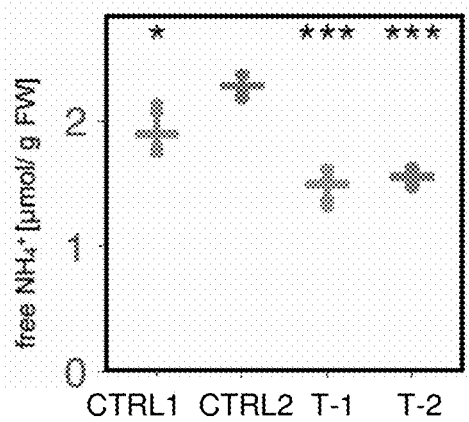
Figure 20:
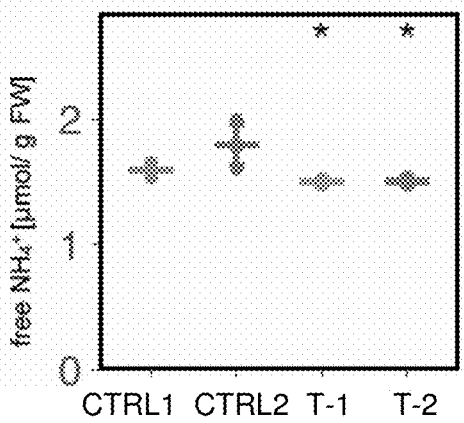

The physiological consequences of the BHAP, as $CO_2$ neutral photorespiratory bypass, were tested by analyzing the phenotype of the established BHAP *Arabidopsis thaliana* plants. This included the quantification of phenotypic parameters like plant growth, rosette size and leaf size, as well as the measurement of free ammonium in green tissue. In all cases, the transgenic plants engineered with the BHAP performed markedly better than the ggt1 mutant (background), which was used as negative control (FIGS. 18, 19, and 20).

Example 9—Metabolomic Analysis of BHAP Plants

Figure 21:
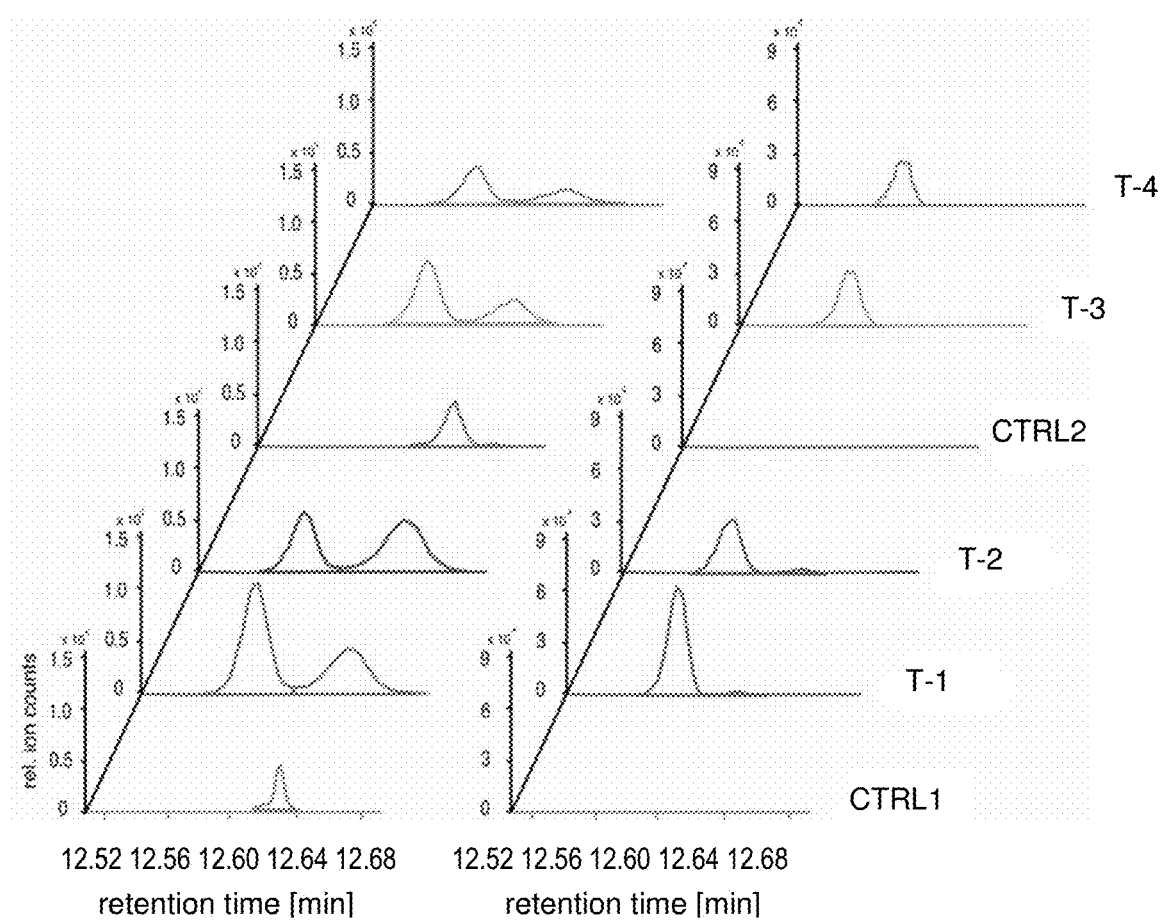
FIG. 21: Metabolite profiling. Representative extracted ion chromatogram for the masses 281.1023 (graphs on left), and 292.1346 (graph on right). CTRL1: Col-0, T-1: Col::BHAP #1, T-2: Col::BHAP #2, CTRL2: ggt1-1, T-3: ggt1-1::BHAP #1, T-4: ggt1-1::BHAP #2.
Figure 22:
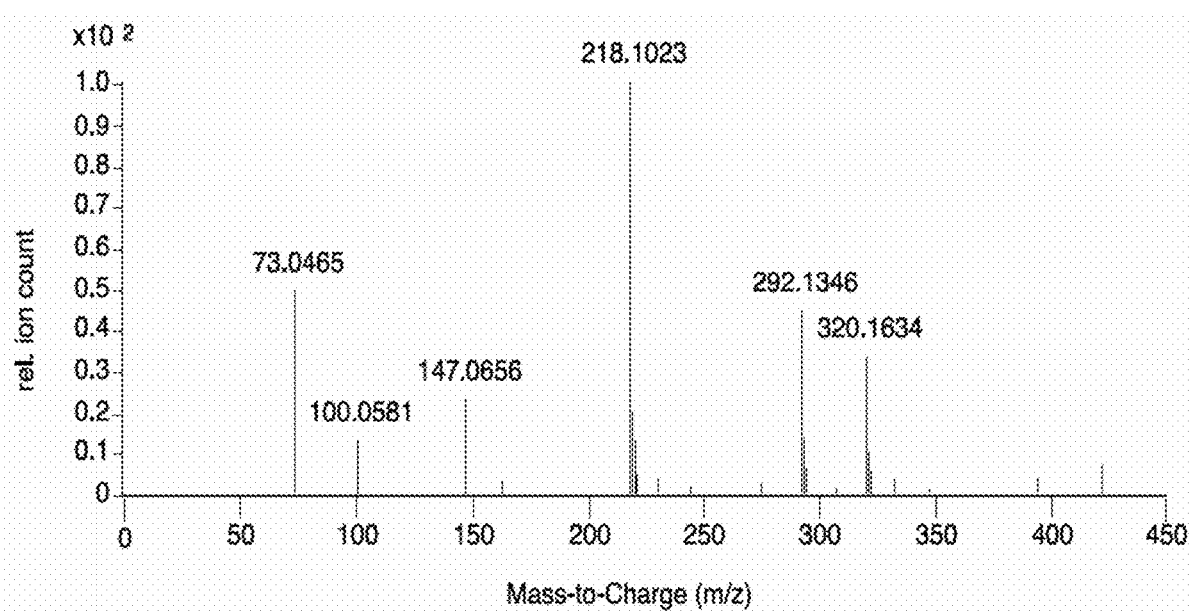
FIG. 22: Metabolite profiling. Deconvoluted mass spectrum of β-hydroxyaspartate.
Figure 23:
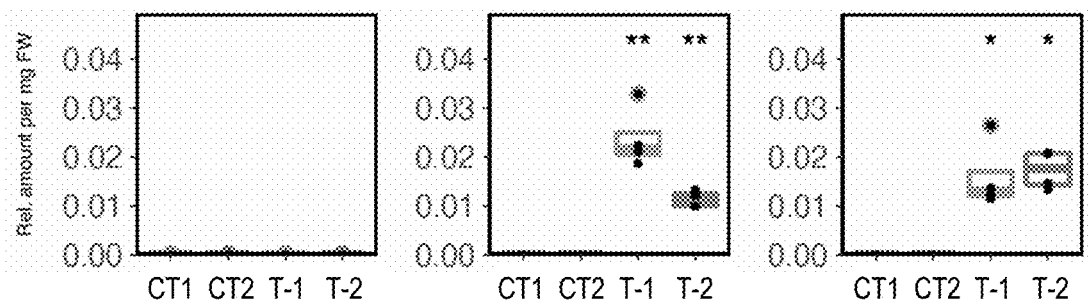
FIG. 23: Metabolite profiling. Relative metabolite levels of (A) β-hydroxyaspartate, (B) glycine, (C) aspartate and (D) malate. Green tissue of 14 days old seedlings was harvested in the middle of the light phase. Plants were grown either at 3000 ppm $CO_2$ (HC, left graph), 400 ppm $CO_2$ (AC, middle graph) or shifted from 3000 ppm $CO_2$ to 400 ppm $CO_2$ three days prior harvest (Shift, right graph). CT1: Col-0, CT2: ggt1-1, T-1: ggt1-1::BHAP #1, T-2: ggt1-1::BHAP #2. Student's t-test against ggt1-1 mutant. Asterisks indicate significance after multiple testing correction using Benjamini-Hochberg. $p<0.05=*$, $p<0.01=$, $p<0.001=*$. n=4.
Figure 23:
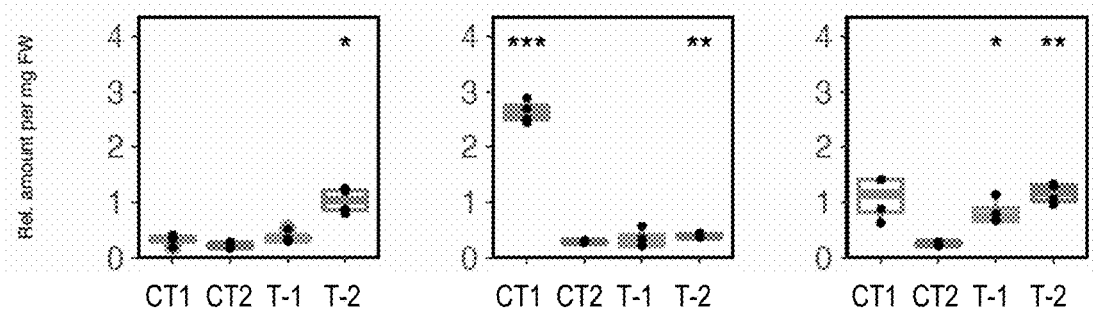
Figure 23:
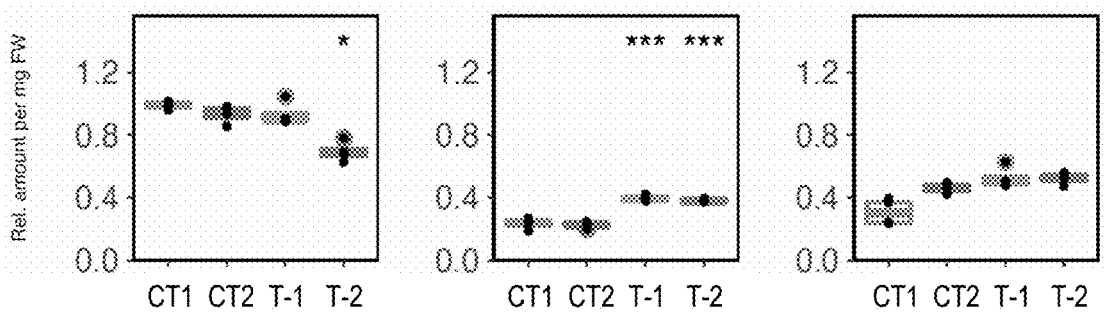
Figure 23:
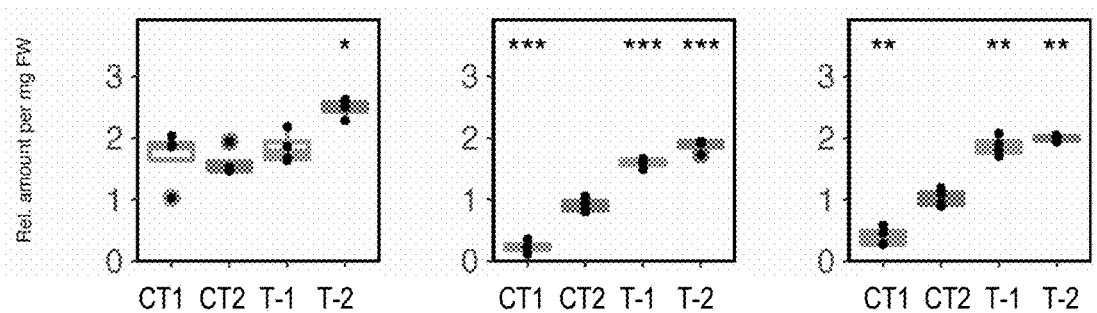

Metabolic flux through the BHAP was tested by quantifying cellular aspartate levels, as BHAP intermediate, and malate levels as described in the Method section. As expected, aspartate and malate levels were significantly increased in plant lines engineered with the BHAP under photorespiratory conditions (FIG. 23C, D). To analyze the metabolic effects of the BHAP on photorespiratory metabolism, the levels of glycine (FIG. 23B) were also analyzed. Furthermore, β-hydroxyaspartate as a unique metabolite of the BHAP was successfully identified in transgenic plant lines, while this compound was completely absent in negative control lines (FIGS. 21-23). This demonstrates unequivocally that the BHAP is indeed operating in these transgenic plant lines.

Example 10—Gas Exchange Measurements in BHAP Plants

In order to confirm the improved carbon efficiency of BHAP plants photorespiratorily released $CO_2$ will be measured by gas exchange and quantified as described by (Long, S P and Bernacchi, CJ Journal of Experimental Botany 2003). A lowered photorespiratory $CO_2$ loss will be observed in BHAP plants. Furthermore, respiratory $CO_2$ release will be determined to exclude enhanced respiratory $CO_2$ release in BHAP plants. The improved carbon efficiency of the BHAP plants results in a lowered $CO_2$ compensation point.

Example 11—BHAP Implementation in Plants Cytoplasm, Chloroplast or Mitochondria

The implementation of BHAP in cellular compartments such as mitochondria, chloroplast and cytosol is possible and of interest.

The implementation of BHAP in plant cell cytosol can be accomplished by targeting BHAP enzymes to the cytosol using the nucleotide sequences coding the polypeptides with the enzymatic activities (a)-(d) without a specific organellar targeting sequences (IsRed: SEQ ID NOs 908 and 909, BHAA: SEQ ID NOs 910 and 911, BHAD: SEQ ID NOs 912 and 913, and AsGAT: SEQ ID NOs 914 and 915).

As glyoxylate is low in chloroplast and mitochondria, the establishing of the BHAP requires the expression of glycolate dehydrogenase (EC 1.1.99.14) (enzymatic activity (e)) for glyoxylate production, fused to chloroplast or mitochondria targeting sequences.

Thus, establishing the BHAP in mitochondria requires only one additional gene for functionality, since produced oxaloacetate is directly metabolized by the TCA cycle.

BHAP expression in chloroplasts requires further an ATP-dependent phosphoenolpyruvate carboxykinase (PEPCK, EC 4.1.1.49) (enzymatic activity (f)) for downstream metabolism of oxaloacetate. Oxaloacetate produced by the BHAP will be decarboxylated by PEPCK and generated phosphoenolpyruvate will be converted into 2-phosphoglycerate by plastidial enolase, ENO1 (At1g74030 (http://doi.wiley.com/10.1016/j.febslet.2009.02.017)) and further into 3-phosphoglycerate by plastidial phosphoglycerate mutase (PGM, At5g51820). Produced 3-phosphoglycerate subsequently enters photosynthetic carbon metabolism. Although the decarboxylation of oxaloacetate in the chloroplast might positively influence $CO_2$ assimilation, the PEPCK step requires one ATP per produced phosphoenolpyruvate, thereby weakening the energy-conserving principle of the BHAP. Furthermore, produced PEP might be distributed between 3-phosphoglycerate production and the shikimate pathway for aromatic amino acid biosynthesis. Alternatively, oxaloacetate is reduced by a NAD(P)-dependent malate dehydrogenase to produce malate that can be exported from the chloroplast via Dit1 (At5g12860).

Therefore, the implementation of BHAP in plant cell mitochondria can be accomplished by targeting BHAP enzymes to the mitochondria using the nucleotide sequences coding the polypeptides with the enzymatic activities (a) erythro-β-hydroxyaspartate aldolase, (b) erythro-β-hydroxyaspartate dehydratase, (c) iminosuccinate reductase, (d) aspartate-glyoxylate transaminase, and (e) glycolate dehydrogenase fused to a N-terminal targeting sequence such as the serine hydroxymethyltransferase 1 (At4g37930) (SEQ ID No 919).

The implementation of BHAP in plant cell chloroplast can be accomplished by targeting BHAP enzymes to the chloroplast using the nucleotide sequences coding the polypeptides with the enzymatic activities (a) erythro-β-hydroxyaspartate aldolase, (b) erythro-β-hydroxyaspartate dehydratase, (c) iminosuccinate reductase, (d) aspartate-glyoxylate transaminase, (e) glycolate dehydrogenase, and (f) phosphoenolpyruvate carboxykinase fused to a N-terminal targeting sequence such as the *Arabidopsis* ferredoxin-2 (At1 g60950) (SEQ ID No 917).

Example 12—Implementing the BHAP as a Heterologous Photorespiration Bypass Pathway into Cyanobacteria The four genes of the BHAP were successfully integrated at two different neutral sites of the *S. elongatus* PCC7942 chromosome. This was done both in the WT strain and in a deletion strain that lacks the genes necessary for the formation of carboxysomes (ccmK-O), and therefore requires elevated atmospheric $CO_2$ concentrations for growth (this strain is henceforth referred to as ΔK-O). Subsequently, successful expression of the pathway enzymes was verified by measuring enzyme activities in cell-free extracts.

Figure 13:
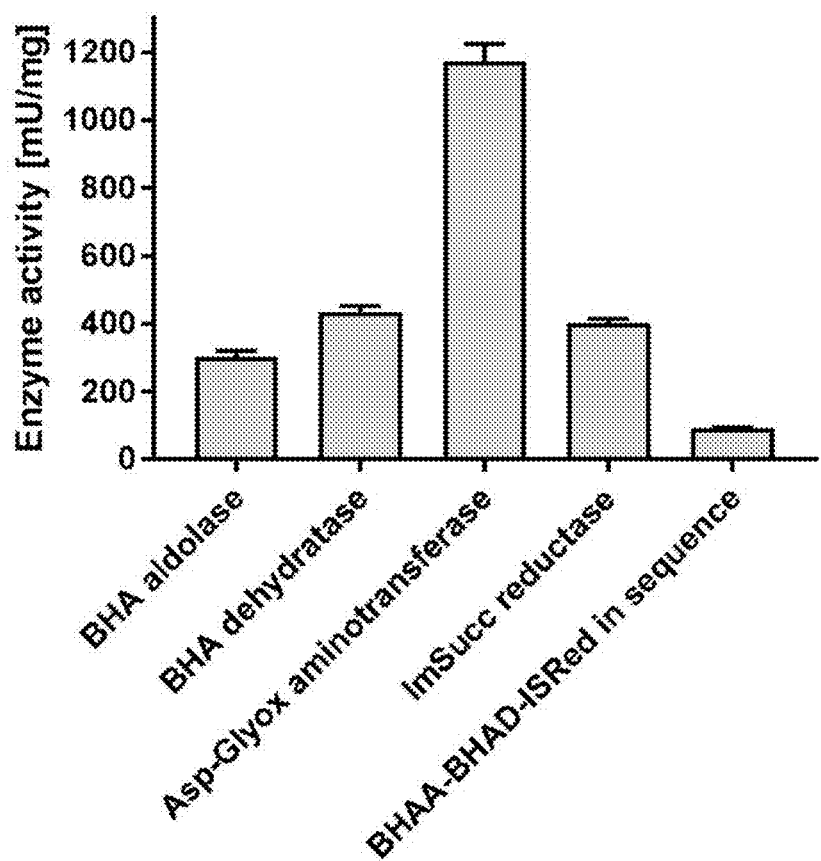
FIG. 13: shows the activities of BHAP enzymes measured in cell-free extracts of *S. elongatus* PCC7942 ΔK-O. To determine the single enzyme activities, required coupling enzymes were added in excess. The rightmost bar shows the activity of the BHAA-BHAD-ISRed reaction sequence, measured without additional coupling enzymes. The average of three replicates is shown; error bars represent standard deviations.

As shown in FIG. 13, the activity of each single enzyme in the ΔK-O strain was at least 300 mU/mg, while the reaction sequence from glycine and glyoxylate to aspartate (via BHA aldolase, BHA dehydratase and iminosuccinate reductase) was measured at an activity of ~100 mU/mg, notably without any additional coupling enzymes. It can therefore be assumed that the expression level of the BHAP enzymes is high enough to sustain photorespiratory flux in *S. elongatus* PCC7942 ΔK-O.

Figure 14:
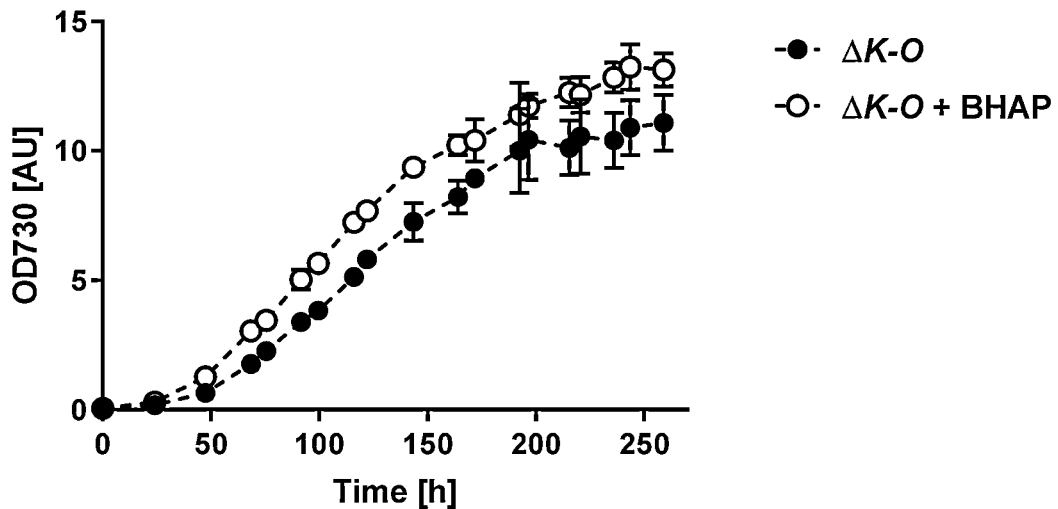
FIG. 14: shows the Growth curves of engineered cyanobacterial strains at 30° C. Three replicate cultures of each strain were grown in a light incubator in an atmosphere containing 0.5% $CO_2$. Samples were taken twice each day, and $OD_{730}$ was measured manually in a spectrophotometer after suitable dilution. The average of three replicates is shown; error bars represent standard deviations.
Figure 15:
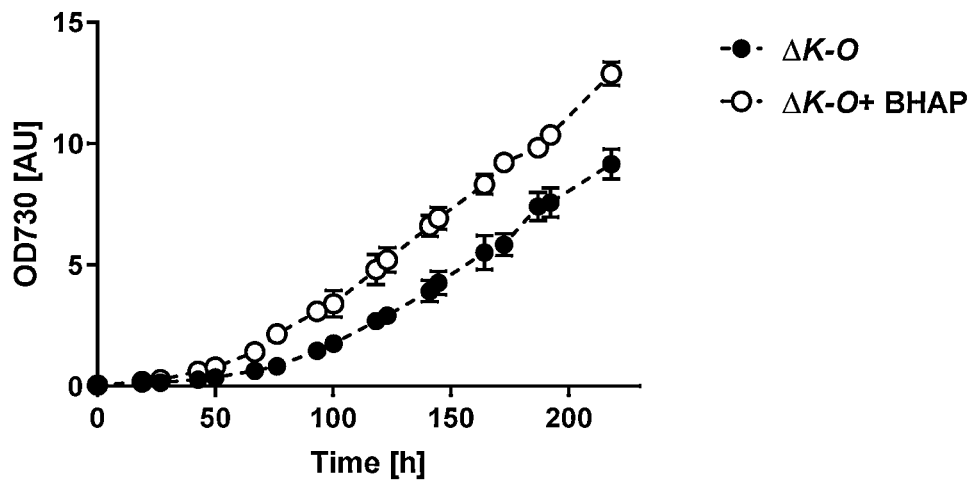
FIG. 15: shows the Growth curves of engineered cyanobacterial strains at 37° C. Three replicate cultures of each strain were grown in a light incubator in an atmosphere containing 0.5% $CO_2$. Samples were taken twice each day, and $OD_{730}$ was measured manually in a spectrophotometer after suitable dilution. The average of three replicates is shown; error bars represent standard deviations.

Next, it was tested whether the implementation of the BHAP in the ΔK-O background conferred a specific phenotype due to improved capabilities for photorespiration. To this end, three replicate cultures (50 mL in baffled shake flasks) of each strain were grown at 30° C. in a light incubator in an atmosphere containing 0.5% $CO_2$, and growth curves were recorded. This experiment was independently repeated three times; FIG. 14 shows representative growth curves from one of the three experiments. The same experiment was also conducted once at 37° C. to investigate the effect of elevated temperature on photorespiration; the results are shown in FIG. 15.

For all experiments, the slope of the growth curves during the linear growth phase was determined. As shown in Table 9, implementation of the BHAP in the ΔK-O background resulted in significantly increased slopes compared to the control strain in all cases. Taken together, these results confirm that implementation of the BHAP in the ΔK-O background permits faster growth of the engineered strain.

TABLE 9

Slopes derived from cyanobacterial growth curves. Suitable intervals of the growth curves were fitted with linear regression. The average slope ± standard deviation of three replicates is given, and it was compared whether the slopes of the two strains were significantly different in each experiment.

| Experiment | Interval for linear regression [h] | Slope ΔK-O | Slope ΔK-O + BHAP | Significant difference? |
|---|---|---|---|---|
| 30° C., I | 80-190 | 0.080 ± 0.002 | 0.096 ± 0.003 | Yes; p = 0.0004 |
| 30° C., II | 45-140 | 0.070 ± 0.002 | 0.086 ± 0.001 | Yes; p < 0.0001 |
| 30° C., III | 45-125 | 0.076 ± 0.002 | 0.092 ± 0.002 | Yes; p = 0.0002 |
| 37° C. | 90-190 | 0.062 ± 0.002 | 0.074 ± 0.001 | Yes; p < 0.0001 |

Example 13—Alternative Approaches for BHAP Implementation in Plants

An alternative to the detailed expression of the BHAP under photosynthetic promoters is the constitutive active expression using the *Agrobacterium* NOS (SEQ ID No: 924) and MAS promoter (SEQ ID No: 925), the cauliflower mosaic virus 35S promoter (SEQ ID No: 926) and the *Arabidopsis* UBIQUITIN10 promoter. This approach allows BHAP expression in photosynthetic and heterotrophic tissue as well as a time/light independent expression. It is worth mentioning that the implementation of non-native plant promoters increases potential effects of post-transcriptional gene silencing.

Example 14—Implementation of BHAP in *Nicotiana tabacum*

The enzymes of the BHAP are successfully expressed in *Nicotiana tabacum* using the above-described plant transformation methods. Enzyme activity of each BHAP enzyme is maintained in *Nicotiana tabacum*.

Example 15—Characterization of BHAC Enzymes from Other Bacterial Species 5 enzymes each are chosen from the provided list of iminosuccinate reductase sequences (SEQ ID 1-299) and aspartate-glyoxylate aminotransferase sequences (SEQ ID 300-599). These enzymes are cloned, expressed, and purified according to the protocols described in the Methods section. Subsequent enzymatic assays demonstrate that these BHAC enzymes from other bacterial species indeed have the respective activity of iminosuccinate reductases or aspartate-glyoxylate aminotransferases, as suggested. Their kinetic parameters are largely in accordance with the previously measured parameters of the enzymes from *Paracoccus denitrificans*. These results underline that the provided list of sequences indeed contains a multitude of enzymes with the proposed activities, which could be used in various combinations to engineer a functional BHAC into plant hosts.

SEQUENCE LISTING

The patent contains a lengthy sequence listing. A copy of the sequence listing is available in electronic form from the USPTO web site (https://seqdata.uspto.gov/?pageRequest=docDetail&DocID=US12378570B2). An electronic copy of the sequence listing will also be available from the USPTO upon request and payment of the fee set forth in 37 CFR 1.19(b)(3).

What is claimed is:

1. A transgenic plant comprising: (a) a heterologous nucleic acid encoding an erythro-β-hydroxyaspartate aldolase enzyme, (b) a heterologous nucleic acid encoding an erythro-β-hydroxyaspartate dehydratase enzyme, (c) a heterologous nucleic acid encoding an iminosuccinate reductase enzyme comprising an amino acid sequence selected from SEQ ID NO: 1-299, or an amino acid sequence having at least 80% sequence identity to a sequence selected from SEQ ID NO: 1-299 and (d) a heterologous nucleic acid encoding an aspartate-glyoxylate transaminase enzyme comprising an amino acid sequence selected from SEQ ID NO: 300-599, or an amino acid sequence having at least 80% sequence identity to a sequence selected from SEQ ID NO:300-599.

2. The transgenic plant of claim 1, wherein (c) iminosuccinate reductase enzyme comprises an amino acid sequence selected from SEQ ID NO: 1, 7, 22, 25, 26, 39, 47, 58, 75, 123, 135, or 160, or an amino acid sequence having at least 80% sequence identity to a sequence selected from SEQ ID NO: 1, 7, 22, 25, 26, 39, 47, 58, 75, 123, 135, or 160.

3. The transgenic plant of claim 1, wherein the (c) iminosuccinate reductase enzyme comprises an amino acid sequence as set forth in SEQ ID NO: 135, or an amino acid sequence having at least 80% sequence identity to said sequence and the aspartate-glyoxylate transaminase enzyme comprises the amino acid sequence as set forth in SEQ ID NO:433, or an amino acid sequence having at least 80% sequence identity to said sequence.

4. The transgenic plant of claim 1, wherein (a) erythro-p-hydroxyaspartate aldolase enzyme is C-terminally fused to the peroxisomal targeting signal having the amino acid sequence of SEQ ID NO: 952 and enzymes (b)-(d) are N-terminally fused to the peroxisomal targeting signal having the amino acid sequence SKL.

5. The transgenic plant of claim 1, further comprising (e) a nucleic acid encoding a glycolate dehydrogenase enzyme and (f) a nucleic acid encoding a phosphoenolpyruvate carboxykinase enzyme, wherein said enzymes (a)-(f) are localized to the chloroplast and are N-terminally fused to the *Arabidopsis* Ferredoxin-2 chloroplastic target peptide having the amino acid sequence of SEQ ID NO: 917.

6. The transgenic plant of claim 1, wherein the plant is selected from *Helianthus annuus, Brassica napus, Camelina sativa, Oryza sativa, Hordeum vulgare, Triticum* spp., *Avena sativa, Solanum lycopersicum, Solanum tuberosum, Glycine max, Beta vulgaris, Nicotiana tabacum*, and *Arabidopsis thaliana*.

7. A method for the production of a transgenic plant according to claim 1 with altered photorespiration and improved $CO_2$ fixation, comprising introducing into a cell or tissue of said plant one or more heterologous nucleic acids encoding a polypeptide having the enzymatic activity of
  (a) erythro-β-hydroxyaspartate aldolase enzyme,
  (b) erythro-β-hydroxyaspartate dehydratase enzyme,
  (c) iminosuccinate reductase enzyme, and
  (d) aspartate-glyoxylate transaminase enzyme,
wherein the introduction of said nucleic acid(s) results in a de novo expression of the polypeptide having the enzymatic activity of
  (a) erythro-β-hydroxyaspartate aldolase enzyme,
  (b) erythro-β-hydroxyaspartate dehydrataseenzyme,
  (c) iminosuccinate reductase enzyme, and
  (d) aspartate-glyoxylate transaminase enzyme,
wherein the enzymatic activity of (c) iminosuccinate reductase enzyme comprises an amino acid sequence selected from SEQ ID NO: 1-299, or an amino acid sequence having at least 80% sequence identity to a sequence selected from SEQ ID NO: 1-299; and the enzymatic activity of (d) aspartate-glyoxylate transaminase enzyme comprises an amino acid sequence selected from SEQ ID NO: 300-599, or an amino acid sequence having at least 80% sequence identity to a sequence selected from SEQ ID NO: 300-599.

8. The method of claim 7, wherein the (c) iminosuccinate reductase enzyme comprises an amino acid sequence selected from SEQ ID NO: 1, 7, 22, 25, 26, 39, 47, 58, 75, 123, 135, or 160, or an amino acid sequence having at least 80% sequence identity to a sequence selected from SEQ ID NO: 1, 7, 22, 25, 26, 39, 47, 58, 75, 123, 135, or 160.

9. The method of claim 7, wherein the (c) iminosuccinate reductase enzyme comprises an amino acid sequence as set forth in SEQ ID NO: 135, or an amino acid sequence having at least 80% sequence identity to said sequence; and the (d) aspartate-glyoxylate transaminase enzyme comprises the amino acid sequence as set forth in SEQ ID NO: 433, or an amino acid sequence having at least 80% sequence identity to said sequence.

10. The method of claim 7, wherein the (a) erythro-β-hydroxyaspartate aldolase enzyme is C-terminally fused to the peroxisomal targeting signal having the amino acid sequence of SEQ ID NO: 952 and enzymes (b)-(d) are N-terminally fused to the peroxisomal targeting signal having the amino acid sequence SKL.

11. The method of claim 7, the transgenic plant further comprises (e) a nucleic acid encoding a glycolate dehydrogenase enzyme and (f) a nucleic acid encoding a phosphoenolpyruvate carboxykinase enzyme, wherein said enzymes (a)-(f) are localized to the chloroplast and are N-terminally fused to the Arabidopsis Ferredoxin-2 chloroplastic target peptide having the amino acid sequence of SEQ ID NO: 917.

* * * * *